(12) United States Patent
O'Malley et al.

(10) Patent No.: US 10,676,766 B2
(45) Date of Patent: Jun. 9, 2020

(54) BIOLOGICAL PRODUCTION OF METHYL METHACRYLATE

(71) Applicants: The Regents of the University of California, Oakland, CA (US); Mitsubishi Chemical Corporation, Chiyoda-ku (JP)

(72) Inventors: Michelle O'Malley, Santa Barbara, CA (US); Kevin Solomon, West Lafayette, IN (US); Wataru Mizunashi, Tokyo (JP); Fujio Yu, Tokyo (JP)

(73) Assignees: The Regents of the University of California, Oakland, CA (US); Mitsubishi Chemical Corporation, Chiyoda-ku (JP)

( * ) Notice: Subject to any disclaimer, the term of this patent is extended or adjusted under 35 U.S.C. 154(b) by 47 days.

(21) Appl. No.: 15/958,859

(22) Filed: Apr. 20, 2018

(65) Prior Publication Data

US 2018/0346942 A1    Dec. 6, 2018

Related U.S. Application Data

(63) Continuation of application No. PCT/JP2016/081345, filed on Oct. 21, 2016.

(60) Provisional application No. 62/245,980, filed on Oct. 23, 2015.

(51) Int. Cl.

| | |
|---|---|
| C12P 7/62 | (2006.01) |
| C12N 9/00 | (2006.01) |
| C12P 7/40 | (2006.01) |
| C12P 11/00 | (2006.01) |
| C12N 15/52 | (2006.01) |
| C12N 9/02 | (2006.01) |
| C12P 7/42 | (2006.01) |
| C12N 15/81 | (2006.01) |
| C12P 19/32 | (2006.01) |
| C12N 15/09 | (2006.01) |

(52) U.S. Cl.
CPC ............... *C12P 7/62* (2013.01); *C12N 9/001* (2013.01); *C12N 15/52* (2013.01); *C12N 15/81* (2013.01); *C12P 7/40* (2013.01); *C12P 7/42* (2013.01); *C12P 11/00* (2013.01); *C12P 19/32* (2013.01); *C12Y 103/08007* (2015.07); *C12N 15/09* (2013.01); *C12Y 103/99003* (2013.01); *C12Y 203/01084* (2013.01)

(58) Field of Classification Search
CPC .................................. C12P 7/62; C12N 9/001
See application file for complete search history.

(56) References Cited

U.S. PATENT DOCUMENTS

| | | |
|---|---|---|
| 2010/0035314 A1 | 2/2010 | Mueller et al. |
| 2012/0110693 A1 | 5/2012 | Drouard et al. |
| 2015/0184207 A1 | 7/2015 | Sato et al. |
| 2015/0191756 A1 | 7/2015 | Sato et al. |
| 2016/0145665 A1 | 5/2016 | Sato et al. |

FOREIGN PATENT DOCUMENTS

| | | |
|---|---|---|
| CA | 2 688 292 A1 | 12/2008 |
| EP | 2 894 224 A1 | 7/2015 |
| JP | 2010-528597 A | 8/2010 |
| JP | 2011-519561 A | 7/2011 |
| WO | 2007/110394 A2 | 10/2007 |
| WO | 2008/145737 A1 | 12/2008 |
| WO | 2009/135074 A2 | 11/2009 |
| WO | 2011/031897 A1 | 3/2011 |
| WO | 2012/135789 A2 | 10/2012 |
| WO | WO2014/038214 A1 | 3/2014 |
| WO | WO2014/038216 A1 | 3/2014 |
| WO | WO2015/015784 A1 | 2/2015 |
| WO | WO-2015031653 A2 * | 3/2015 ............ C08F 20/10 |

OTHER PUBLICATIONS

Andresen et al. 2000; Isolated 2-methylbutyrykglycinuria caused by short/branched-chain acyl CoA dehydrogenase deficiency: Identification of a new enzyme defect, resolution of tis molecular basis, and evidence for distinct acyl-CoA dehydrogenases in isoleucine and valine metabolism. Am J.Hum.Genet. 67: 1095-1103.*

Kegg. 2019; Valine, leucine, and isoleucine degradation—Reference pathway. at www.genonne.jp/kegg-bin/show_pathway?map00280.*

Telford et al. 1999; Isolation and characterization of the cDNA encoding the precursor fora novel member of the acyl-CoA dehydrogenase gene family. Biochimica et Biophysica Acta. 1446:371-376.*

Nguyen et al. 2002; Identification of the isobutyryl-CoA dehydrogenase and its deficiency in humans. Molecular Genetics and Metabolism. 77: 68-79.*

Australian Office Action dated Jul. 5, 2019, in Patent Application No. 2016340470, 3 pages.

Extended European Search Report dated Sep. 17, 2018 in Patent Application No. 16857580.1, 12 pages.

Pyo et al.—"A new route for the synthesis of methacrylic acid from 2-methyl-1,3-propanediol by integrating biotransformation and catalytic dehydration", Green Chemistry, 2012, 14, pp. 1942-1948.

International Search Report issued in PCT/JP2016/081345 dated Jan. 10, 2017 with English translation.

Office Action dated Feb. 11, 2020, in Brazilian Patent Application No. 112018007901-4 (w/ English Translation) (6 pages).

* cited by examiner

*Primary Examiner* — Karen Cochrane Carlson
(74) *Attorney, Agent, or Firm* — Oblon, McClelland, Maier & Neustadt, L.L.P.

(57) ABSTRACT

The invention relates to an engineered eukaryotic microorganism into which a gene encoding an acyl-CoA dehydrogenase is introduced and a method for producing methacrylic acid esters such as MMA and MMA-CoA and precursors thereof using the microorganism.

9 Claims, 5 Drawing Sheets

Specification includes a Sequence Listing.

BCKAD/ *Pseudomonas aeruginosa* PA01
Complex: BKDA1 (E1α) / BKDA2 (E1β) / BKDB (E2) / LPDV (E3)
E1: dehydrogenase
E2: dihydrolipoamide transacylase
E3: dihydrolipoamide dehydrogenase

BIOLOGICAL PRODUCTION OF METHYL METHACRYLATE

RELATED APPLICATION

The present application claims priority based on U.S. Provisional Application No. 62/245,980 (filed on Oct. 23, 2015), and the content thereof is incorporated herein by reference.

TECHNICAL FIELD

The invention relates to an engineered eukaryotic microorganism wherein genes encoding an acyl-CoA dehydrogenase are introduced into the microorganism and a method for producing methacrylic acid esters and precursors thereof using the microorganism.

BACKGROUND ART

Methyl methacrylate (MMA) is a critical raw material in the production of acrylic polymers. MMA is traditionally produced from non-sustainable, hazardous raw materials, such as acetone and hydrogen cyanide. Accordingly, there is a need in the art for MMA production methods that are sustainable and rely on non-toxic production methods.

As such a production method, methods are proposed wherein 2-hydroxyisobutyric acid and 3-hydroxyisobutyric acid to be precursors of methacrylic acids are produced from natural products such as saccharides using naturally occurring microorganisms (see Patent Literatures 1 and 2 and Non Patent Literature 1). However, these methods still rely on chemical techniques in the step for producing a methacrylic acid by dehydrating the precursor.

Additionally, there are methods proposed wherein a methacrylic acid is produced from glucose using a not naturally occurring engineered microorganism into which a plurality of enzyme genes are introduced, but these are the combination of a known enzyme reaction and a hypothetical enzyme reaction analogized therefrom and not verified (see Patent Literatures 3 to 5). Particularly, Patent Literature 5 presents examples of a wide variety of biocatalysts (hydrolase, wax ester synthase, alcohol acetyltransferase) which have typical ester-producing activity but fails to state that those biocatalysts have the synthesis activity of methacrylic acid esters.

The inventors have reported a production method of a methacrylic acid ester from methacrylyl-CoA by biocatalysts (Patent Literature 6) and a production method of a methacrylic acid ester from biomass in the presence of an alcohol by adding the action of AAT to a microorganism which has a methacrylic acid producing ability (Patent Literature 7). Additionally, the inventors have reported a method for synthesizing methacrylyl-CoA from 3-hydroxyisobutyryl-CoA using *E. coli* into which a dehydratase gene is introduced (Patent Literature 8).

CITATION LIST

Patent Literature

Patent Literature 1: WO2007/110394
Patent Literature 2: WO2008/145737
Patent Literature 3: WO2009/135074
Patent Literature 4: WO2011/031897
Patent Literature 5: WO2012/135789
Patent Literature 6: WO2014/038214
Patent Literature 7: WO2014/038216
Patent Literature 8: WO2015/015784

Non Patent Literature

Non Patent Literature 1: Green Chemistry, 2012, 14, 1942-1948

SUMMARY OF INVENTION

Technical Problem

It is an object of the invention to provide a novel biological production method of methacrylic acid esters such as MMA.

Solution to Problem

Hosts for industrial use such as *E. coli* do not produce MAA-CoA even when exogenous genes related to the biosynthesis of methacrylyl-CoA (MAA-CoA) are introduced thereinto. This is presumed due to the absence of the electron acceptor for acyl-CoA dehydrogenase, which is one of the enzymes related to the biosynthesis of MAA-CoA, in *E. coli*. The inventors succeeded in the biological production of MAA-CoA by introducing an exogenous acyl-CoA dehydrogenase gene into a yeast cell.

More specifically, the invention relates to the following (1) to (10).
(1) A eukaryotic microorganism into which a gene encoding an acyl-CoA dehydrogenase (isobutyryl-CoA dehydrogenase) is introduced.
(2) The eukaryotic microorganism according to (1), wherein the gene encoding an acyl-CoA dehydrogenase is derived from at least one selected from genus *Pseudomonas*, genus *Bacillus*, genus *Sphingobacterium*, genus *Comamonas*, genus *Brevundimonas*, genus *Sphingomonas*, genus *Ochrobactrum*, genus *Pedobacter*, genus *Paenibacillus*, genus *Achromobacter*, genus *Acinetobacter*, genus *Shewanella*, genus *Listonella*, genus *Agrobacterium*, genus *Mesorhizobium*, genus *Rhizobium*, genus *Paracoccus*, genus *Xanthobacter*, genus *Streptomyces*, genus *Geobacillus*, genus *Rhodococcus*, genus *Saccharomyces*, genus *Candida* and genus *Aspergillus*.
(3) The eukaryotic microorganism according to (1) or (2), wherein a signal sequence-added acyl-CoA dehydrogenase gene is introduced in such a way that the acyl-CoA dehydrogenase expresses a function in a mitochondrion.
(4) The eukaryotic microorganism according to (3), wherein the signal sequence comprises the sequence as set forth in SEQ ID NO: 1.
(5) The eukaryotic microorganism according to any one of (1) to (4), wherein the eukaryotic microorganism is a yeast.
(6) The eukaryotic microorganism according to any one of (1) to (4), further comprising at least one exogenous gene selected from genes encoding branched-chain keto acid dehydrogenase, genes encoding enoyl-CoA hydratase, genes encoding hydroxyacyl-CoA hydrolase, genes encoding thioesterase, and genes encoding alcohol acyl transferase.
(7) A method for producing methacrylyl-CoA from valine using the eukaryotic microorganism according to (6).
(8) A method for producing 3-hydroxyisobutyryl-CoA from valine using the eukaryotic microorganism according to (6).
(9) A method for producing 3-hydroxyisobutyric acid from valine using the eukaryotic microorganism according to (6).
(10) A method for producing a methacrylic acid ester from valine using the eukaryotic microorganism according to (6).

Provided herein are novel methods for the biological production of MMA and MMA precursors in engineered microorganisms, wherein one or more enzymes which enable MMA or MMA precursor production is introduced into the microorganism. Herein, one or more enzyme genes including an acyl-CoA dehydrogenase gene, which enables the production of MMA or an MMA. Optionally, the one or more enzymes is targeted to the mitochondria. Mitochondrial targeting of enzymes enables the biosynthetic processes which produce MMA or MMA precursors to take advantage of the favorable energetic, enzymatic, and other characteristics of the mitochondrial niche, which greatly enhances yield. In one implementation of the invention, various enzymes involved in valine biosynthesis and degradation are engineered into a host eukaryotic microorganism wherein, through a series of reactions, they produce MMA precursors or MMA from valine, the one or more enzymes being optionally targeted to the mitochondria. The scope of the invention encompasses novel gene vectors for the transformation of hosts, novel microorganism strains expressing enzymes which enable the synthesis of MMA precursors or MMA, and MMA precursors and MMA produced by the engineered microorganisms of the invention.

Advantageous Effects of Invention

According to the invention, the biological production of methacrylic acid ester precursors such as methacrylyl-CoA (MAA-CoA) is provided. The MAA precursor is biologically converted to methacrylic acid esters such as MAA to begin with, thereby enabling the bio-integrated production of methacrylic acid esters. The method of the invention is a biological production which uses an organic raw material such as biomass and thus can produce methacrylic acid esters non-toxically without destroying environments. Additionally, methacrylic acid esters to be obtained are water-insoluble, thereby being collected and purified easily from a fermented product, whereby low-cost production of methacrylic acid esters is enabled.

DESCRIPTION OF EMBODIMENTS

Figure 1:
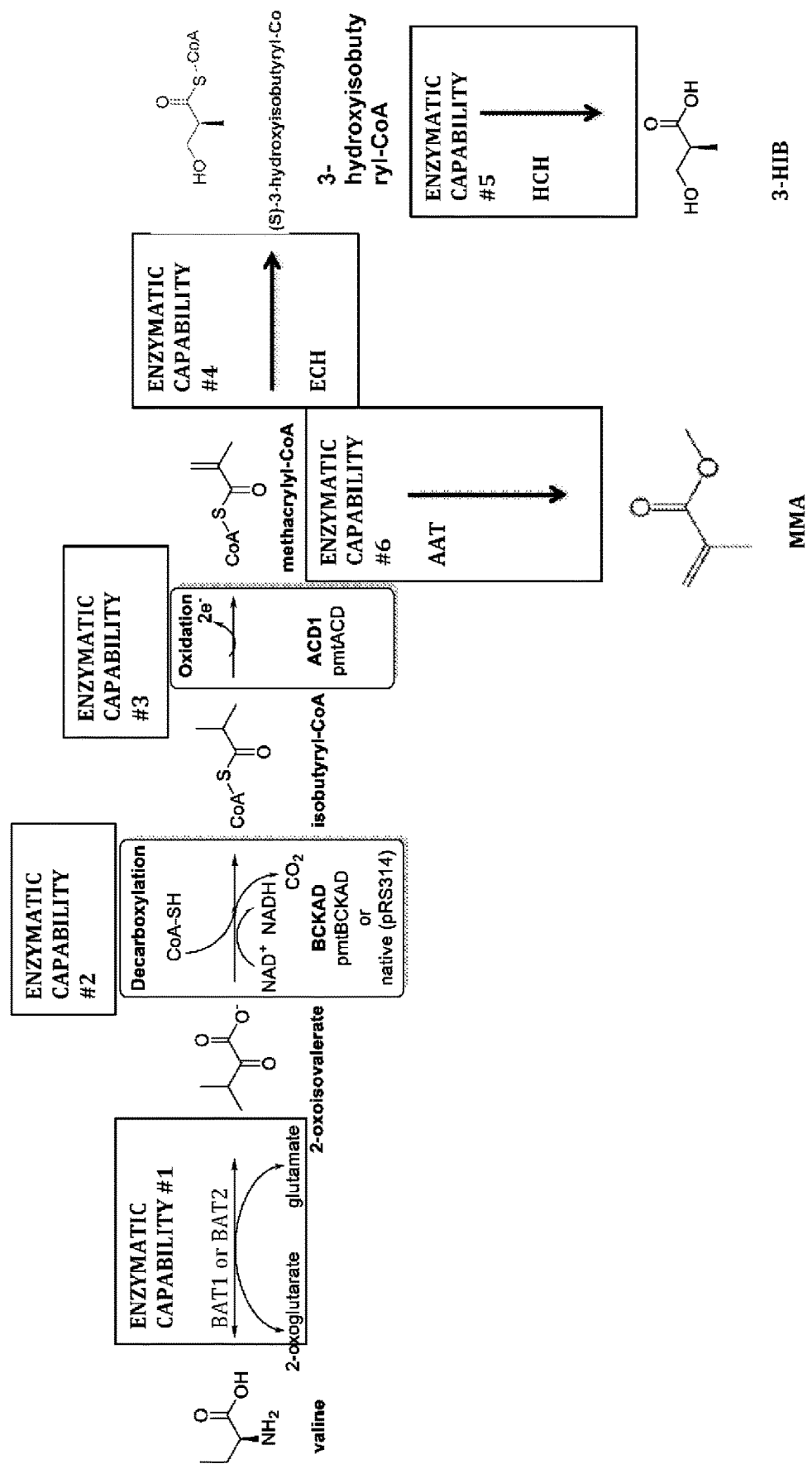
FIG. 1 is an overview of the synthetic pathways for the production of MMA precursors and MMA from valine.

Part 1: Microorganisms Capable of Producing MMA and MMA Precursors

The invention encompasses an engineered microorganism which produces methacrylic acid esters such as methyl methacrylate (MMA) or precursors thereof such as methacrylyl-CoA (MAA-CoA) and 3-hydroxyisobutyric acid (3-HIB) by the various biosynthesis pathways. Collectively, methacrylic acid esters and precursors thereof (for example, MMA and ester thereof) will be referred to herein as "MMA end-products." The above biosynthesis pathways comprise a number of enzymatic steps that are accomplished in microorganisms engineered to possess the appropriate set of enzymatic capabilities, as described below.

In the invention, the "methacrylic acid" (IUPAC name: 2-methyl-2-propenoic acid) includes any salts or ionized forms thereof. Examples of the salt of methacrylic acid include sodium salts, potassium salts, calcium salts and magnesium salts.

The "methacrylic acid ester" is a compound represented by formula 1. In the formula 1, R represents a linear or branched hydrocarbon group having 1 to 20 carbon atoms. The hydrocarbon group may be saturated or unsaturated, acyclic or cyclic. Linear or branched-chain unsubstituted alkyl groups, aralkyl groups or aryl groups having 1 to 10 carbon atoms are preferable. Particularly preferable are alkyl groups, benzyl groups or phenyl groups having 1 to 8 carbon atoms of methyl group, ethyl group, n-propyl group, iso-propyl group, n-butyl group, isobutyl group, sec-butyl group, tert-butyl group, n-pentyl group, isopentyl group, tert-pentyl group, n-hexyl group, isohexyl group, 2-hexyl group, dimethyl butyl group, ethyl butyl group, heptyl group, octyl group and 2-ethylhexyl group.

$$CH_2=C(CH_3)COO-R \qquad \text{(Formula 1)}$$

Examples of the "methacrylic acid ester precursor" include methacrylyl-CoA, 3-hydroxyisobutyryl-CoA, 3-hydroxyisobutyric acid and isobutyryl-CoA.

Engineered Microorganisms

The invention encompasses various engineered eukaryotic microorganisms which produce methacrylic acid esters and precursors thereof as end-products. Alternatively, the engineered eukaryotic microorganisms of the invention may comprise eukaryotic microorganisms which produce methacrylic acid esters.

Microorganisms (Host Cells)

The engineered eukaryotic microorganism of the invention comprises cells which will be referred to as "hosts" or "host cells," as they serve as hosts for the various Enzymatic Capabilities described below. A host cell can be of any species. Exemplary classes of hosts include yeasts, filamentous fungi and algae. Examples of the species which may be provided as the host include *Saccharomyces cerevisiae*, *Pichia pastoris* and *Aspergillus niger*.

Preferable microorganism (host cell) is yeasts. Exemplary species which may serve as hosts include microorganisms belonging to genus *Saccharomyces* such as *Saccharomyces cerevisiae*, microorganisms belonging to genus *Schizosaccharomyces*, microorganisms belonging to genus *Pichia* such as *Pichia pastoris*, microorganisms belonging to genus *Candida* such as *Candida tropicalis, Candida lipolytica, Candida utilis* and *Candida sake*, microorganisms belonging to genus *Kluyveromyces*, microorganisms belonging to genus *Williopsis*, microorganisms belonging to genus *Debaryomyces*, microorganisms belonging to genus *Galactomyces*, microorganisms belonging to genus *Torulaspora*, microorganisms belonging to genus *Rhodotorula*, microorganisms belonging to genus *Yarrowia*, and microorganisms belonging to genus *Zygosaccharomyces*. Of these, microorganisms belonging to genus *Saccharomyces* are preferable, and *Saccharomyces cerevisiae* is more preferable.

Preferred host species are those which are amenable to cell culture or which are otherwise suitable for bioproduction, wherein end-products can be synthesized in large scale production and can be inexpensively harvested and separated from the cells in which they are produced.

Transformation Methods

The host cell of the invention may be transformed to express any number of different enzymatic proteins, regulatory sequences, and other genes and gene products. Transformation may be accomplished by any means known in the art which is amenable to the selected host microorganism. In yeast, for example, alkaline cationic transformation protocols, such as lithium acetate in combination with single-stranded carrier DNA and polyethylene glycol may be used. Examples of other transformation techniques adaptable for the host cell transformation include chemical transformation methods known in the art (e.g., DEAE-dextran, polyethyleneimine, dendrimer, polybrene, calcium phosphate, lipofectin, DOTOP, Lipofectamine or CTAB/DOPE, and DOTMA); and physical transformation methods (e.g., injections, gene shock or laser-guided transduction, fine needles, and gene guns). The engineered microorganism of the invention may be transiently transformed or stably transformed.

Gene Constructs

The enzymatic gene and/or accompanying regulatory sequence introduced into the host microorganism can be configured in various ways. It will be understood that heterologous expression of a foreign gene in a host microorganism may require that codon optimizations and other sequence modifications be made in order that the gene be properly transcribed and translated in the host, as known in the art. It will also be understood that localization signals, promoters, and other elements which may be combined with the enzymatic gene sequence must be selected or altered so as to be effective in the host microorganisms, as known in the art.

Enzymatic gene introduced into the host microorganism will typically be operably linked to the downstream of a promoter sequence. In some embodiments, a constitutive promoter is utilized with the enzymatic gene to ensure constant and high level expression. Exemplary constitutive promoters include the TEF1, and GDS promoters. The genes coding for the enzyme may alternatively be placed under the control of an inducible promoter. For example, in some embodiments, one or more enzymatic capabilities of the engineered microorganism may be placed under the control of the inducible promoter known in the art and compatible with the host microorganism in order to allow for timed staging of enzymatic steps in the production of MMA end-products. For example, the GAL 10 and GAL 1 galactose inducible promoters may be used in yeast.

Localization Signals

Further, the enzymatic gene introduced into host microorganisms may also comprise a trafficking signal that directs the localization of the expression product to a specific cellular compartment. For example, a signal which localizes enzymes to the mitochondrial compartments, the cell membrane, or the chloroplast (in plant cells) may be operably linked to gene sequences coding for enzymatic proteins. The scope of the invention encompasses an engineered host wherein one or more of the enzymes introduced into the host are targeted to the mitochondria, for example, the matrix of the mitochondria. Further, the enzyme gene introduced into the host microorganism may comprise a trafficking signal which commands the localization to a specific cell compartment. For example, the matrix of the mitochondria. Examples of the signal sequence which can achieve such a targeting in a yeast include the presequence of subunit 9 of the yeast mitochondrial ATPase (Su9)(SEQ ID NO: 1) or the presequence of subunit IV of the yeast cytochrome C oxidase (Cox1) (Literature [Avalos et al., Compartmentalization of metabolic pathways in yeast mitochondria improves the production of branched-chain alcohols. Nature Biotechnol. 2013, pr; 31 (4):335-41. 2013, pr; 31(4):335-41]. Additionally, exemplary mitochondrial targeting sequences also include the presequence (residues 19-40) of the human NAOH dehydrogenase (ubiquinone) flavoprotein 2 (NOUFV2); the presequence (residues 1-20) of influenza virus protein (PB2), the presequence of yeast tryptophanyl tRNA-synthase (MSW), and the sequences described in Literature [Omura, "Mitochondria-Targeting Sequence, a Multi-Role Sorting Sequence Recognized at All Steps of Protein Import into Mitochondria," Journal of Biochemistry. 1998, Vol. 123 Issue 6, p 1010-1016. 7p]. In some embodiments, the enzymatic gene is intended to operate in the cytosol and no trafficking moieties are utilized. In another embodiment, one or more of the expressed enzymatic proteins is designed to be secreted from the cell and gene sequences coding for such proteins are operably linked to secretion signals with direct the translated protein out of the cells.

In some embodiments, a termination sequence is utilized. For example, in yeast, CYCT transcription termination sequence may be operably linked to the enzymatic protein coding sequences to enhance proper expression in yeast cells. Other exemplary regulatory elements that can be used include the rrnB (T1) element from *E. coli*, the AdhT element from yeast, and the TEF1 element from yeast.

It will be understood that the enzymatic capabilities described below may be introduced by the transformation of the host microorganism with various nucleic acid constructs. Exemplary nucleic acid constructs of the invention comprise plasmids and linear nucleic acid constructs, which may comprise cloning vectors, expression cassettes, and other DNA constructs known in the art.

For a given host microorganism being transformed to express two or more enzymatic genes, such two or more enzymatic genes may be introduced into the microorganism as a single nucleic acid construct, or may be introduced in separate nucleic acid constructs. When two or more separate nucleic acid constructs are utilized, the transformation of the microorganism may occur as a single transformation event employing multiple nucleic acid constructs, or as a series of sequential transformation events to introduce the two or more genes in stages.

It will be understood that genes introduced into the host microorganism may be under the control of different promoters. For example, where the relative ratios of enzymes need to be tuned, some may be under the control of a weak promoter and some may be under the control of a stronger promoter, in order to create the desired balance of enzymatic activity in the cell. Likewise, enzymatic activity can be balanced by varying the copy number of the various enzymatic genes introduced into the host microorganism. For example a gene may be introduced as a single copy or as two, three, four or more copies, for example as end-to-end copies on a single nucleic acid construct.

Gene Equivalents

Reference to various enzymatic genes, proteins, and other genetic/protein elements is made herein. It will be understood by one of skill in the art that equivalents may be used in place of the gene and protein sequences enumerated or referenced herein. For example, variants of cited sequences may be used, including nucleic acid sequence variants and peptide sequence variants.

For example, the listed sequences may have nucleotides and/or amino acids comprising 1 or several, for example, 1 to 10, 1 to 6, 1 to 4, 1 to 3, 1 or 2 substitutions, additions, insertions or deletions, introduced thereinto.

Alternatively, genes and proteins having nucleic acid sequences or amino acid sequences having a sequence identity of 60% or more, preferably 70% or more, more preferably 80% or more, further preferably 90% or more, to the sequences mentioned are included.

Such alterations of the original sequences may be neutral or may alter (e.g. enhance) the desired enzymatic activity of the target gene. It will also be understood that gene equivalents include orthologs, paralogs, and homologs of the enumerated sequence from other species. In one embodiment, the equivalent genes of the invention comprise genes having at least 90 percent sequence identity or similarity between the wild type sequence and the variant. Further, it will be understood that functional equivalents of enumerated gene sequences may be used, such functional equivalents performing identical enzymatic functions to the enzymes or regulatory signals, while not necessarily having sequence similarity, identity or homology.

Enzymatic Capabilities

According to the present application, the engineered microorganism of the invention comprises specific "enzymatic capabilities." Having specific enzymatic capabilities means that the microorganism has an ability to produce a specific product from a specific reactant and such an ability may be enabled by the expression of one or more enzymes which are commanded to convert the reactant to the product.

In some embodiments, one or more enzymatic capabilities possessed by the microorganism are the results of the microorganism having been transformed to express the requisite protein or multiple proteins (e.g. as in the multimeric BCKAD enzyme comprising Enzymatic Capability 2, as describe below) for such enzymatic capability. In some embodiments, all of the enzymatic capabilities possessed by an engineered microorganism of the invention are imparted by introduction of the requisite proteins by genetic transformation. In some embodiments, one or more of the enzymatic capabilities possessed by the engineered microorganism of the invention comprises a native enzymatic capability, i.e. the host microorganism's native enzymes are capable of imparting the activity without supplementation by introduced genes. For example, in some microorganisms, Enzymatic Capability 2 is possessed by the microorganism through the action of native BCKAD genes.

In one embodiment, one or more proteins introduced by the transformation are targeted to a cell compartment or organelle. In an embodiment, one or more or all proteins introduced into the microorganism by the transformation are targeted to mitochondria. In one embodiment, the mitochondrial-targeted proteins are targeted to the mitochondrial matrix. In one embodiment, the host cell is a yeast cell and the mitochondrial-targeted protein comprises a targeting moiety comprising the Su9 or Cox1 mitochondrial-targeted sequence.

The pathways for forming the MMA end-products are largely overlapping, as depicted in FIG. 1.

For example, three enzymatic steps convert valine to MAA-CoA, which can be harvested and further processed ex-vivo to create MMA. Alternatively, an MAA-CoA producing microorganism may comprise additional enzymatic capabilities that allow the MAA-CoA to be converted to 3-HIB or MMA directly. 3-HIB formed by the microorganism can be harvested and processed ex-vivo to form MMA.

While the efficient formation of MMA end-products is not found in natural microorganisms, the pathways which allow the engineered microorganism to form such products are based on valine synthetic and catabolic pathways that are common across a wide range of microorganisms. Accordingly, there is a diverse set of enzymes available to the skilled practitioner for imparting the desired enzymatic capabilities. The specific enzymatic capabilities which allow formation of MAACoA, 3-HIB, and MMA are described hereinafter in detail.

Enzymatic Capability 1: Production of 2-Oxoisovaleric Acid from Valine

A first enzymatic step in the conversion of valine to am MMA precursor is the formation of 2-oxoisovalerate from valine. This may be accomplished by the action of a branched chain aminotransferase enzyme (BCAT). In some cases, native BCAT activity or equivalent enzymatic activity is present and sufficient to produce adequate 2-oxoisovalerate from valine for the synthesis of an MMA precursor. Alternatively, host microorganisms may be transformed to express one or more BCAT or equivalent genes. Exemplary BCAT genes include the BAT1 and BAT2 genes of *Saccharomyces cerevisiae*. Additional BCAT genes that may be used include those listed in Table 1.

TABLE 1

BAT1 and BAT2 Genes
Uniprot Gene and Protein Codes

| Type | Gene | Protein |
|---|---|---|
| BAT1 | Q6FTS6 | Q6FTS6_CANGA |
| BAT1 | J8PN44 | J8PN44_SACAR |
| BAT1 | C8ZA09 | C8ZA09_YEAS8 |
| BAT1 | E7KPP0 | E7KPP0_YEASL |
| BAT1 | E7QFU8 | E7QFU8_YEASZ |
| BAT1 | E7NIT4 | E7NIT4_YEASO |
| BAT1 | E7Q4X8 | E7Q4X8_YEASB |
| BAT1 | B3LSW9 | B3LSW9_YEAS1 |
| BAT1 | C7GN93 | C7GN93_YEAS2 |
| BAT1 | BCA1 | BCA1_YEAST |
| BAT1 | A6ZTB5 | A6ZTB5_YEAS7 |
| BAT1 | G2WFT2 | G2WFT2_YEASK |
| BAT1 | E7KDL7 | E7KDL7_YEASA |
| BAT1 | C7GN93 | C7GN93_YEAS2 |
| BAT1 | BCA1 | BCA1_YEAST |
| BAT1 | A6ZTB5 | A6ZTB5_YEAS7 |
| BAT1 | G2WFT2 | G2WFT2_YEASK |
| BAT1 | L0PE74 | L0PE74_PNEJ8 |
| BAT1 | B6K620 | B6K620_SCHJY |
| BAT1 | BCA1 | BCA1_SCHPO |
| BAT1 | Q6CAN4 | Q6CAN4_YARLI |
| BAT1 | K0KC83 | K0KC83_WICCF |
| BAT1 | K0KHQ6 | K0KHQ6_WICCF |
| BAT1 | I2GXJ8 | I2GXJ8_TETBL |
| BAT1 | I2H598 | I2H598_TETBL |
| BAT1 | G8BQ96 | G8BQ96_TETPH |
| BAT1 | G8BQZ4 | G8BQZ4_TETPH |
| BAT1 | A7TPV1 | A7TPV1_VANPO |
| BAT1 | A7TT81 | A7TT81_VANPO |
| BAT1 | J7RVX9 | J7RVX9_KAZNA |
| BAT1 | J7S3X0 | J7S3X0_KAZNA |
| BAT1 | H2ARK1 | H2ARK1_KAZAF |
| BAT1 | H2AW48 | H2AW48_KAZAF |
| BAT1 | H2AYK9 | H2AYK9_KAZAF |
| BAT1 | G0VL14 | G0VL14_NAUCC |

TABLE 1-continued

BAT1 and BAT2 Genes
Uniprot Gene and Protein Codes

| Type | Gene | Protein |
|---|---|---|
| BAT1 | G0WA50 | G0WA50_NAUDC |
| BAT1 | G0WHB0 | G0WHB0_NAUDC |
| BAT1 | Q6FK92 | Q6FK92_CANGA |
| BAT1 | Q6FTS6 | Q6FTS6_CANGA |
| BAT1 | J8PN44 | J8PN44_SACAR |
| BAT1 | J8Q0H7 | J8Q0H7_SACAR |
| BAT1 | J8TXF1 | J8TXF1_SACK1 |
| BAT1 | C8ZA09 | C8ZA09_YEAS8 |
| BAT1 | C8ZBU8 | C8ZBU8_YEAS8 |
| BAT1 | E7KPP0 | E7KPP0_YEASL |
| BAT1 | E7KQQ1 | E7KQQ1_YEASL |
| BAT1 | E7QFU8 | E7QFU8_YEASZ |
| BAT1 | E7QGZ0 | E7QGZ0_YEASZ |
| BAT1 | E7NIT4 | E7NIT4_YEASO |
| BAT1 | E7NJL2 | E7NJL2_YEASO |
| BAT1 | E7Q4X8 | E7Q4X8_YEASB |
| BAT1 | E7Q5U8 | E7Q5U8_YEASB |
| BAT1 | B3LQM7 | B3LQM7_YEAS1 |
| BAT1 | B3LSW9 | B3LSW9_YEAS1 |
| BAT1 | C7GN93 | C7GN93_YEAS2 |
| BAT1 | C7GPU1 | C7GPU1_YEAS2 |
| BAT1 | BCA1 | BCA1_YEAST |
| BAT1 | BCA2 | BCA2_YEAST |
| BAT1 | A6ZQA4 | A6ZQA4_YEAS7 |
| BAT1 | A6ZTB5 | A6ZTB5_YEAS7 |
| BAT1 | G2WFT2 | G2WFT2_YEASK |
| BAT1 | G2WHF0 | G2WHF0-YEASK |
| BAT1 | B5VKD7 | B5VKD7_YEAS6 |
| BAT1 | B5VLT5 | B5VLT5_YEAS6 |
| BAT1 | E7KDL7 | E7KDL7_YEASA |
| BAT1 | E7KEL9 | E7KEL9_YEASA |
| BAT1 | G8ZSL8 | G8ZSL8_TORDC |
| BAT1 | C5E1Q1 | C5E1Q1_ZYGRC |
| BAT1 | C5DFQ6 | C5DFQ6_LACTC |
| BAT1 | Q6CX88 | Q6CX88_KLULA |
| BAT1 | G8JWT0 | G8JWT0_ERECY |
| BAT1 | Q75BE8 | Q75BE8_ASHGO |
| BAT1 | C4WX3 | C4WX3_CLAL4 |
| BAT1 | G3B9K0 | G3B9K0_CANTC |
| BAT1 | A5DGQ7 | A5DGQ7_PICGU |
| BAT1 | Q6BSQ6 | Q6BSQ6_DEBHA |
| BAT1 | G8YUX2 | G8YUX2_PICSO |
| BAT1 | A3LNY1 | A3LNY1_PICST |
| BAT1 | A3LVU4 | A3LVU4_PICST |
| BAT1 | G3ALC5 | G3ALC5_SPAPN |
| BAT1 | G3AR71 | G3AR71_SPAPN |
| BAT1 | A5DUJ5 | A5DUJ5_LODEL |
| BAT1 | A5DY11 | A5DY11_LODEL |
| BAT1 | H8WXC3 | H8WXC3_CANO9 |
| BAT1 | H8X5S6 | H8X5S6_CANO9 |
| BAT1 | G8BDW7 | G8BDW7_CANPC |
| BAT1 | G8BGY0 | G8BGY0_CANPC |
| BAT1 | C5M6U4 | C5M6U4_CANTT |
| BAT1 | C5MJG1 | C5MJG1_CANTT |
| BAT1 | B9WB98 | B9WB98_CANDC |
| BAT1 | B9WEE3 | B9WEE3_CANDC |
| BAT1 | Q59YS9 | Q59YS9_CANAL |
| BAT1 | Q5AHX4 | Q5AHX4_CANAL |
| BAT1 | Q5AHX5 | Q5AHX5_CANAL |
| BAT1 | C4YIA7 | C4YIA7_CANAW |
| BAT1 | C4YNT6 | C4YNT6_CANAW |
| BAT1 | E7RA63 | E7RA63_PICAD |
| BAT1 | F2QZT3 | F2QZT3_PICP7 |
| BAT1 | C4R7A4 | C4R7A4_PICPG |
| BAT2 | | |
| BAT2 | L0PE74 | L0PE74_PNEJ8 |
| BAT2 | B6K620 | B6K620_SCHJY |
| BAT2 | BCA1 | BCA1_SCHPO |
| BAT2 | Q6CAN4 | Q6CAN4_YARLI |
| BAT2 | K0KC83 | K0KC83_WICCF |
| BAT2 | K0KHQ6 | K0KHQ6_WICCF |
| BAT2 | I2GXJ8 | I2GXJ8_TETBL |
| BAT2 | I2H598 | I2H598_TETBL |
| BAT2 | G8BQ96 | G8BQ96_TETPH |
| BAT2 | G8BQZ4 | G8BQZ4_TETPH |
| BAT2 | A7TPV1 | A7TPV1_VANPO |
| BAT2 | A7TT81 | A7TT81_VANPO |
| BAT2 | J7RVX9 | J7RVX9_KAZNA |
| BAT2 | J7S3X0 | J7S3X0_KAZNA |
| BAT2 | H2ARK1 | H2ARK1_KAZAF |
| BAT2 | H2AW48 | H2AW48_KAZAF |
| BAT2 | H2AYK9 | H2AYK9_KAZAF |
| BAT2 | G0VL14 | G0VL14_NAUCC |
| BAT2 | G0WA50 | G0WA50_NAUDC |
| BAT2 | G0WHB0 | G0WHB0_NAUDC |
| BAT2 | Q6FK92 | Q6FK92_CANGA |
| BAT2 | Q6FTS6 | Q6FTS6_CANGA |
| BAT2 | J8PN44 | J8PN44_SACAR |
| BAT2 | J8Q0H7 | J8Q0H7_SACAR |
| BAT2 | J8TXF1 | J8TXF1_SACK1 |
| BAT2 | C8ZA09 | C8ZA09_YEAS8 |
| BAT2 | C8ZBU8 | C8ZBU8_YEAS8 |
| BAT2 | E7KPP0 | E7KPP0_YEASL |
| BAT2 | E7KQQ1 | E7KQQ1_YEASL |
| BAT2 | E7QFU8 | E7QFU8_YEASZ |
| BAT2 | E7QGZ0 | E7QGZ0_YEASZ |
| BAT2 | E7NIT4 | E7NIT4_YEASO |
| BAT2 | E7NJL2 | E7NJL2_YEASO |
| BAT2 | E7Q4X8 | E7Q4X8_YEASB |
| BAT2 | E7Q5U8 | E7Q5U8_YEASB |
| BAT2 | B3LQM7 | B3LQM7_YEAS1 |
| BAT2 | B3LSW9 | B3LSW9_YEAS1 |
| BAT2 | C7GN93 | C7GN93_YEAS2 |
| BAT2 | C7GPU1 | C7GPU1_YEAS2 |
| BAT2 | BCA1 | BCA1_YEAST |
| BAT2 | BCA2 | BCA2_YEAST |
| BAT2 | A6ZQA4 | A6ZQA4_YEAS7 |
| BAT2 | A6ZTB5 | A6ZTB5_YEAS7 |
| BAT2 | G2WFT2 | G2WFT2_YEASK |
| BAT2 | G2WHF0 | G2WHF0_YEASK |
| BAT2 | B5VKD7 | B5VKD7_YEAS6 |
| BAT2 | B5VLT5 | B5VLT5_YEAS6 |
| BAT2 | E7KDL7 | E7KDL7_YEASA |
| BAT2 | E7KEL9 | E7KEL9_YEASA |
| BAT2 | G8ZSL8 | G8ZSL8_TORDC |
| BAT2 | C5E1Q1 | C5E1Q1_ZYGRC |
| BAT2 | C5DFQ6 | C5DFQ6_LACTC |
| BAT2 | Q6CX88 | Q6CX88_KLULA |
| BAT2 | G8JWT0 | G8JWT0_ERECY |
| BAT2 | Q75BE8 | Q75BE8_ASHGO |
| BAT2 | C4WX3 | C4WX3_CLAL4 |
| BAT2 | G3B9K0 | G3B9K0_CANTC |
| BAT2 | A5DGQ7 | A5DGQ7_PICGU |
| BAT2 | Q6BSQ6 | Q6BSQ6_DEBHA |
| BAT2 | G8YUX2 | G8YUX2_PICSO |
| BAT2 | A3LNY1 | A3LNY1_PICST |
| BAT2 | A3LVU4 | A3LVU4_PICST |
| BAT2 | G3ALC5 | G3ALC5_SPAPN |
| BAT2 | G3AR71 | G3AR71_SPAPN |
| BAT2 | A5DUJ5 | A5DUJ5_LODEL |
| BAT2 | A5DY11 | A5DY11_LODEL |
| BAT2 | H8WXC3 | H8WXC3_CANO9 |
| BAT2 | H8X5S6 | H8X5S6_CANO9 |
| BAT2 | G8BDW7 | G8BDW7_CANPC |
| BAT2 | G8BGY0 | G8BGY0_CANPC |
| BAT2 | C5M6U4 | C5M6U4_CANTT |
| BAT2 | C5MJG1 | C5MJG1_CANTT |
| BAT2 | B9WB98 | B9WB98_CANDC |
| BAT2 | B9WEE3 | B9WEE3_CANDC |
| BAT2 | Q59YS9 | Q59YS9_CANAL |
| BAT2 | Q5AHX4 | Q5AHX4_CANAL |
| BAT2 | Q5AHX5 | Q5AHX5_CANAL |
| BAT2 | C4YIA7 | C4YIA7_CANAW |
| BAT2 | C4YNT6 | C4YNT6_CANAW |
| BAT2 | E7RA63 | E7RA63_PICAD |
| BAT2 | F2QZT3 | F2QZT3_PICP7 |
| BAT2 | C4R7A4 | C4R7A4_PICPG |
| BAT2 | G1XAC5 | G1XAC5_ARTOA |
| BAT2 | G3JGP7 | G3JGP7_CORMM |

TABLE 1-continued

BAT1 and BAT2 Genes
Uniprot Gene and Protein Codes

| Type | Gene | Protein |
|---|---|---|
| BAT2 | C9STB5 | C9STB5_VERA1 |
| BAT2 | G2WSU1 | G2WSU1_VERDV |
| BAT2 | L2G6Q7 | L2G6Q7_COLGN |
| BAT2 | E3QRQ7 | E3QRQ7_COLGM |
| BAT2 | H1VX68 | H1VX68_COLHI |
| BAT2 | F7VW13 | F7VW13_SORMK |
| BAT2 | Q7S699 | Q7S699_NEUCR |
| BAT2 | F8MW76 | F8MW76_NEUT8 |
| BAT2 | G4V0L6 | G4V0L6_NEUT9 |
| BAT2 | G0SAN1 | G0SAN1_CHATD |
| BAT2 | G2QRV4 | G2QRV4_THITE |
| BAT2 | Q2GSR0 | Q2GSR0_CHAGB |
| BAT2 | G2QEV2 | G2QEV2_THIHA |
| BAT2 | F0XML2 | F0XML2_GROCL |
| BAT2 | J3NH78 | J3NH78_GAGT3 |
| BAT2 | G4MK83 | G4MK83_MAGO7 |
| BAT2 | L8FLF5 | L8FLF5_GEOD2 |
| BAT2 | K1WSP9 | K1WSP9_MARBU |
| BAT2 | H0EE28 | H0EE28_GLAL7 |
| BAT2 | A7ENI6 | A7ENI6_SCLS1 |
| BAT2 | G2YC57 | G2YC57_BOTF4 |
| BAT2 | F9X0G1 | F9X0G1_MYCGM |
| BAT2 | K2SB17 | K2SB17_MACPH |
| BAT2 | K2ST37 | K2ST37_MACPH |
| BAT2 | Q0UN77 | Q0UN77_PHANO |
| BAT2 | E4ZLK4 | E4ZLK4_LEPMJ |
| BAT2 | B2VTC9 | B2VTC9_PYRTR |
| BAT2 | E3RLT7 | E3RLT7_PYRTT |
| BAT2 | H6BV59 | H6BV59_EXODN |
| BAT2 | C1H0V7 | C1H0V7_PARBA |
| BAT2 | C1GC48 | C1GC48_PARBD |
| BAT2 | C0S9L5 | C0S9L5_PARBP |
| BAT2 | F2TPG3 | F2TPG3_AJEDA |
| BAT2 | C5JPW9 | C5JPW9_AJEDS |
| BAT2 | C5G9D5 | C5G9D5_AJEDR |
| BAT2 | A6RH28 | A6RH28_AJECN |
| BAT2 | C0NIH3 | C0NIH3_AJECG |
| BAT2 | F0U4P3 | F0U4P3_AJEC8 |
| BAT2 | C6H7T8 | C6H7T8_AJECH |
| BAT2 | C5FF64 | C5FF64_ARTOC |
| BAT2 | E5QYK2 | E5QYK2_ARTGP |
| BAT2 | F2Q3W3 | F2Q3W3_TRIEC |
| BAT2 | F2S550 | F2S550_TRIT1 |
| BAT2 | F2SNV1 | F2SNV1_TRIRC |
| BAT2 | D4B2E4 | D4B2E4_ARTBC |
| BAT2 | D4DE82 | D4DE82_TRIVH |
| BAT2 | C4JT41 | C4JT41_UNCRE |
| BAT2 | J3KDG0 | J3KDG0_COCIM |
| BAT2 | C5P8J6 | C5P8J6_COCP7 |
| BAT2 | E9D0N0 | E9D0N0_COCPS |
| BAT2 | B6Q223 | B6Q223_PENMQ |
| BAT2 | B6QEX9 | B6QEX9_PENMQ |
| BAT2 | B8LUG0 | B8LUG0_TALSN |
| BAT2 | B8MBA9 | B8MBA9_TALSN |
| BAT2 | B6HRY8 | B6HRY8_PENCW |
| BAT2 | K9H3Y0 | K9H3Y0_PEND1 |
| BAT2 | K9FRA1 | K9FRA1_PEND2 |
| BAT2 | A1CCC2 | A1CCC2_ASPCL |
| BAT2 | A1CGS8 | A1CGS8_ASPCL |
| BAT2 | A1CY02 | A1CY02_NEOFI |
| BAT2 | B0Y5G1 | B0Y5G1_ASPFC |
| BAT2 | Q4WNL4 | Q4WNL4_ASPFU |
| BAT2 | C8V969 | CBV969_EMENI |
| BAT2 | Q5AV02 | Q5AV02_EMENI |
| BAT2 | G7X6X6 | G7X6X6_ASPKW |
| BAT2 | G3Y9W8 | G3Y9W8_ASPNA |
| BAT2 | A2QHM8 | A2QHM8_ASPNC |
| BAT2 | Q0CHM6 | Q0CHM6_ASPTN |
| BAT2 | B8NA84 | B8NA84_ASPFN |
| BAT2 | I8I126 | I8I126_ASPO3 |
| BAT2 | Q2UG50 | Q2UG50_ASPOR |
| BAT2 | F4P9T3 | F4P9T3_BATDJ |
| BAT2 | I1BVM3 | I1BVM3_RHIO9 |
| BAT2 | I1C2I9 | I1C2I9_RHIO9 |
| BAT2 | I1CJX9 | I1CJX9_RHIO9 |
| BAT2 | F4SC44 | F4SC44_MELLP |
| BAT2 | J3PTD9 | J3PTD9_PUCT1 |
| BAT2 | E3KPV1 | E3KPV1_PUCGT |
| BAT2 | G7DX97 | G7DX97_MIXOS |
| BAT2 | A8PZH7 | A8PZH7_MALGO |
| BAT2 | I2FTT8 | I2FTT8_USTH4 |
| BAT2 | I2G3T8 | I2G3T8_USTH4 |
| BAT2 | E6ZJK3 | E6ZJK3_SPORE |
| BAT2 | E6ZRU0 | E6ZRU0_SPORE |
| BAT2 | Q4P2X7 | Q4P2X7_USTMA |
| BAT2 | Q4PIE8 | Q4PIE8_USTMA |
| BAT2 | I4YAT5 | I4YAT5_WALSC |
| BAT2 | J5SV95 | J5SV95_TRIAS |
| BAT2 | K1WJA5 | K1WJA5_TRIAC |
| BAT2 | E6RFZ8 | E6RFZ8_CRYGW |
| BAT2 | J9VWH6 | J9VWH6_CRYNH |
| BAT2 | Q55HM3 | Q55HM3_CRYNB |
| BAT2 | Q5K761 | Q5K761_CRYNJ |
| BAT2 | G4TBC5 | G4TBC5_PIRID |
| BAT2 | G4TKH5 | G4TKH5_PIRID |
| BAT2 | D8PN41 | D8PN41_SCHCM |
| BAT2 | D8QEG6 | D8QEG6_SCHCM |
| BAT2 | D8QKG1 | D8QKG1_SCHCM |
| BAT2 | D8QKG3 | D8QKG3_SCHCM |
| BAT2 | F8PKS8 | F8PKS8_SERL3 |
| BAT2 | F8QC65 | F8QC65_SERL3 |
| BAT2 | F8NJB4 | F8NJB4_SERL9 |
| BAT2 | F8PBH0 | F8PBH0_SERL9 |
| BAT2 | K5WMI9 | K5WMI9_PHACS |
| BAT2 | K5XD27 | K5XD27_PHACS |
| BAT2 | J4G859 | J4G859_FIBRA |
| BAT2 | J4GSH9 | J4GSH9_FIBRA |
| BAT2 | J4IC35 | J4IC35_FIBRA |
| BAT2 | B8P088 | B8P088_POSPM |
| BAT2 | B8P1C9 | B8P1C9_POSPM |
| BAT2 | B8P391 | B8P391_POSPM |
| BAT2 | B8P3C2 | B8P3C2_POSPM |
| BAT2 | B8P3T6 | B8P3T6_POSPM |
| BAT2 | B8P502 | B8P502_POSPM |
| BAT2 | B8P6B4 | B8P6B4_POSPM |
| BAT2 | B8P6B6 | B8P6B6_POSPM |
| BAT2 | B8P6C8 | B8P6C8_POSPM |
| BAT2 | B8P6D3 | B8P6D3_POSPM |
| BAT2 | B8P6D7 | B8P6D7_POSPM |
| BAT2 | B8P6D8 | B8P6D8_POSPM |
| BAT2 | B8P6E0 | B8P6E0_POSPM |
| BAT2 | B8P6E3 | B8P6E3_POSPM |
| BAT2 | B8PB39 | B8PB39_POSPM |
| BAT2 | B8PB40 | B8PB40_POSPM |
| BAT2 | B8PB41 | B8PB41_POSPM |
| BAT2 | B8PB50 | B8PB50_POSPM |
| BAT2 | B8PB51 | B8PB51_POSPM |
| BAT2 | B8PBJ2 | B8PBJ2_POSPM |
| BAT2 | B8PBJ3 | B8PBJ3_POSPM |
| BAT2 | B8PBJ9 | B8PBJ9_POSPM |
| BAT2 | B8PCD3 | B8PCD3_POSPM |
| BAT2 | B8PDE3 | B8PDE3_POSPM |
| BAT2 | B8PDE8 | B8PDE8_POSPM |
| BAT2 | B8PK93 | B8PK93_POSPM |
| BAT2 | B8PK94 | B8PK94_POSPM |
| BAT2 | B8PK98 | B8PK98_POSPM |
| BAT2 | B8PLQ0 | B8PLQ0_POSPM |
| BAT2 | B8PNG6 | B8PNG6_POSPM |
| BAT2 | E2LGP7 | E2LGP7_MONPE |
| BAT2 | E2LXF2 | E2LXF2_MONPE |
| BAT2 | E2M281 | E2M281_MONPE |
| BAT2 | A8N0B4 | A8N0B4_COPC7 |
| BAT2 | A8N0V2 | A8N0V2_COPC7 |
| BAT2 | B0CPH7 | B0CPH7_LACBS |
| BAT2 | B0DKQ1 | B0DKQ1_LACBS |
| BAT2 | K5WWN9 | K5WWN9_AGABU |
| BAT2 | K5X684 | K5X684_AGABU |
| BAT2 | K9HUV1 | K9HUV1_AGABB |
| BAT2 | K9ICL0 | K9ICL0_AGABB |
| BAT2 | D5GAR6 | D5GAR6_TUBMM |

TABLE 1-continued

BAT1 and BAT2 Genes
Uniprot Gene and Protein Codes

| Type | Gene | Protein |
|---|---|---|
| BAT2 | D5GAR7 | D5GAR7_TUBMM |
| BAT2 | C7Z586 | C7Z586_NECH7 |
| BAT2 | J9MTH0 | J9MTH0_FUSO4 |
| BAT2 | F9FL84 | F9FL84_FUSOF |
| BAT2 | K3V6P5 | K3V6P5_FUSPC |
| BAT2 | I1RYQ4 | I1RYQ4_GIBZE |
| BAT2 | G9NGT1 | G9NGT1_HYPAI |
| BAT2 | G0RC37 | G0RC37_HYPJQ |
| BAT2 | G9N619 | G9N619_HYPVG |
| BAT2 | E9DYK8 | E9DYK8_METAQ |
| BAT2 | E9EQ54 | E9EQ54_METAR |
| BAT2 | J5JG13 | J5JG13_BEAB2 |

Enzymatic Capability 2: Decarboxylation of 2-Oxoisovaleric Acid to Isobutyryl-CoA The second step in the bioproduction of MAA precursors from valine is the decarboxylation of 2-oxoisovalerate to isobutyryl-CoA. This step may be accomplished by the branched-chain α-keto acid dehydrogenase (BCKAD) complex. The BCKAD complex comprises four subunits, the E1 subunit, the E2 subunit, the E3 subunit, and a dihydrolipoamide dehydrogenase.

In some cases, sufficient BCKAD or equivalent activity is present in the host microorganism to efficiently convert 2-oxoisovalerate to isobutyryl-CoA. For example, as described in Example 1, engineered yeast cells produced ample MMA precursors without the introduction of BCKAD genes, demonstrating that sufficient native activity may be present in the host.

Alternatively, the host may be transformed to express one or more enzymes that perform the decarboxylation of 2-oxoisovalerate to isobutyryl-CoA. For example, the host microorganism may be engineered to express the four constituents of the BCKAD complex. For example, the four genes encoding the *Pseudomonas aeruginosa*-BCKAD complex may be introduced into the host to impart or augment native BCKAD activity. These genes include: the bkdA1 gene, encoding E1 (Genbank Accession No. NP250937), bkdA2 gene, encoding E3 (Genbank Accession No. NP_250938), bkdB gene, encoding E2 (Genbank Accession No. NP250939) and IpdV gene, encoding dihydrolipoamide dehydrogenase (Genbank Accession No. NP250940). Alternatively, the host may be transformed to express a bkdA1 gene selected from Table 2, a bkdA2 gene selected from Table 3, a bkdB gene selected from Table 4, and an IpdV gene selected from Table 5.

TABLE 2 bkdA1 Genes

| Genome | Gene ID# | Locus Tag |
|---|---|---|
| *Stigmatella aurantiaca* DW4/3-1 | 310822118 | STAUR_4871 |
| *Glaciecola nitratireducens* FR1064 | 348029317 | GNIT_901 |
| *Corallococcus coralloides* DSM 2259 | 383456734 | COCOR_04759 |
| *Sinorhizobium fredii* HH103 | 378827583 | SFHH103_02998 |
| *Alteromonas macleodi* ATCC 27126 | 406596861 | MASE_09530 |
| *Pseudomonas fluorescens* F113 | 378950264 | PSF113_2346 |
| *Sinorhizobium meliloti* SM11 | 384537524 | SM11_chr3104 |
| *Brucella suis* VBI22 | 376278492 | BSVBI22_B0518 |
| *Shewanella baltica* BA175 | 386324712 | Sbal175_2270 |
| *Brucella melitensis* M5-90 | 384213034 | BM590_B0496 |
| *Alteromonas macleodi* str. 'English Channel 673' | 407683852 | AMEC673_09775 |
| *Marinobacter hydrocarbonoclasticus* ATCC 49840 | 387814424 | MARHY2809 |
| *Pseudomonas aeruginosa* NCGM2.S1 | 386066185 | NCGM2_3256 |
| *Pseudomonas fluorescens* A506 | 387894499 | PflA506_3337 |
| *Alteromonas macleodi* str. 'Balearic Sea AD45' | 407687775 | AMBAS45_09980 |
| *Sinorhizobium meliloti* BL225C | 384530814 | SinmeB_2782 |
| *Thermus thermophilus* JL-18 | 386359631 | TtJL18_0174 |
| *Shewanella baltica* OS117 | 386341194 | Sbal117_2345 |
| *Brucella melitensis* NI | 384446660 | BMNI_II0489 |
| *Brucella canis* HSK A52141 | 376276775 | BCA52141_II0445 |
| *Pseudomonas aeruginosa* M18 | 386058856 | PAM18_2793 |
| *Pseudomonas pulida* S16 | 339488698 | PPS_3805 |
| *Shewanella baltica* OS678 | 378708518 | Sbal678_2203 |
| *Alteromonas macleodi* str. 'Black Sea 11' | 407700100 | AMBLS11_09275 |
| *Marinobacter adhaerens* HP15 | 385329802 | HP15_61 |
| *Burkholderia cepacia* GG4 | 402556979 | GEM_2217 |
| *Brucella melitensis* M28 | 384410135 | BM28_B0497 |
| *Sphingobium* sp. SYK-6 | 347527350 | SLG_09650 |
| *Pseudomonas pulida* DOT-T1E | 397697834 | T1E_5099 |
| *Burkholderia pseudomallei* 1026b | 386856107 | BP1026B_II2449 |
| *Oceanimonas* sp. GK1 | 374335112 | GU3_06465 |
| *Shewanella putrefaciens* 200 | 386313862 | Sput200_2106 |
| *Brucella pinnipedialis* B2/94 | 340792252 | BPI_II505 |
|  | 384223054 | BS1330_II0519 |
| *Pelaglbacterium halotolerans* B2 | 357384137 | KKY_1077 |
| *Sinorhizobium fredii* USDA 257 | 398385221 | USDA257_c54050 |
| *Shewanella woodyi* ATCC 51908 | 170726629 | Swoo_2278 |
| *Shewanella denitrificans* OS217 | 91793142 | Sden_1786 |
| *Shewanella oneidensis* MR-1 | 24373885 | SO_2339 |

TABLE 2-continued bkdA1 Genes

| Genome | Gene ID# | Locus Tag |
|---|---|---|
| *Shewanella halifaxensis* HAW-EB4 | 167624158 | Shal_2234 |
| *Anaeromyxobacter dehalogenans* 2CP-C | 86158863 | Adeh_2441 |
| *Parachlamydia acanthamoebae* UV7 | 338174253 | PUV_02590 |
| *Agrobacterium tumefaciens* str. C58 | 159185754 | Atu3473 |
| *Pseudoalteromonas atlantica* T6c | 109898353 | Patl_2036 |
| *Pseudomonas fluorescens* SBW25 | 229591396 | PFLU3964 |
| *Sorangium cellulosum* 'So ce 56' | 162449842 | sce1571 |
| *Pseudomonas fluorescens* Pf-5 | 70729902 | PFL_2534 |
| *Oceanithermus profundus* DSM 14977 | 313680637 | Ocepr_1750 |
| *Bradyrhizobium japonicum* USDA 110 | 27381442 | blr6331 |
| *Brucella melitensis* ATCC 23457 | 225686316 | BMEA_B0497 |
| *Deinococcus deserti* VCD115 | 226357394 | Deide_23440 |
| *Pseudomonas putida* KT2440 | 26991090 | PP_4401 |
| *Shewanelle loihica* PV-4 | 127512853 | Shew_1925 |
| *Shewanelle baltica* OS185 | 153000673 | Shew185_2149 |
| *Thermus thermophilus* HB8 | 55980198 | TTHA0229 |
| *Brucella suis* 1330 | 23500271 | BRA0524 |
| *Burkholderia pseudomallei* 1106a | 126456753 | BURPS1106A_A3067 |
| *Mesorhizobium ciceri* biovar biserrulae WSM1271 | 319780620 | Mesci_0881 |
| *Polaromonas* sp. JS666 | 91786184 | Bpro_0273 |
| *Burkholderia glumae* BGR1 | 238023732 | bglu_2g02640 |
| *Alicycliphilus denitrificans* BC | 319761347 | Alide_0628 |
| *Brucella abortus* A13334 | 376271257 | BAA13334_II01347 |
| *Alicycliphilus denitrificans* K601 | 330823222 | Alide2_0593 |
| *Burkholderia pseudomallei* 668 | 126444383 | BURPS668_A3193 |
| *Burkholderia gladioli* BSR3 | 330819430 | bgla_2g03040 |
| *Sphingomonas wittichii* RW1 | 148555060 | Swit_2145 |
| *Pseudoalteromonas* sp. SM9913 | 315126681 | PSM_A1605 |
| *Brucella suis* ATCC 23445 | 163844682 | BSUIS_B0519 |
| *Myxococcus xanthus* DK 1622 | 108760073 | MXAN_4564 |
| *Shewanella sediminis* HAW-EB3 | 157375466 | Ssed_2329 |
| *Pseudomonas putida* F1 | 148546693 | Pput_1453 |
| *Brucella abortus* bv. 1 str. 9-941 | 62317615 | BruAb2_0700 |
| *Burkholderia mallei* SAVP1 | 121597380 | BMASAVP1_1036 |
| *Pseudomonas aeruginosa* DK2 | 392984204 | PADK2_14040 |
| *Brevundimonas subvibrioides* ATCC 15264 | 302384438 | Bresu_3332 |
| *Sphingobium chlorophenolicum* L-1 | 334344849 | Sphch_1205 |
| *Shewanella* sp. MR-7 | 114047443 | Shewmr7_1947 |
| *Hahella chejuensis* KCTC 2396 | 83646416 | HCH_03687 |
| *Shewanella violacea* DSS12 | 294140813 | SVI_2042 |
| *Novosphingobium aromaticivorans* DSM 12444 | 87199993 | Saro_1976 |
| *Pseudomonas putida* ND6 | 395447960 | YSA_07994 |
| *Thermus thermophilus* HB27 | 46200059 | TTC1757 |
| *Burkholderia ambifaria* MC40-6 | 172060189 | BamMC406_1134 |
| *Burkholderia pseudomallei* 1710b | 76819484 | BURPS1710b_A1411 |
| *Shewanella frigidimarina* NCIMB 400 | 114563106 | Sfri_1935 |
| *Hirschia baltica* ATCC 49814 | 254293976 | Hbal_1614 |
| *Thermoplasma acidophilum* DSM 1728 | 16082407 | Ta1438 |
| *Mesorhizobium opportunistum* WSM2075 | 337265440 | Mesop_0911 |
| *Sinorhizobium meliloti* 1021 | 15966685 | SMc03201 |
| *Burkholderia mallei* NCTC 10247 | 126447708 | BMA10247_A2302 |
| *Bdellovibrio bacteriovorus* HD100 | 42522535 | Bd0972 |
| *Shewanella baltica* OS155 | 126174438 | Sbal_2222 |
| *Bordetella petrii* DSM 12804 | 163857824 | Bpet3511 |
| *Brucella canis* ATCC 23365 | 161620586 | BCAN_B0522 |
| *Brucella ovis* ATCC 25840 | 148557918 | BOV_A0455 |
| *Colwellia psychrerythraea* 234H | 71281526 | CPS_1582 |
| *Mesorhizobium loti* MAFF303099 | 13473769 | mll4473 |
| *Pseudomonas putida* BIRD-1 | 386011042 | PPUBIRD1_1441 |
| *Stigmatella aurantiaca* DW4/3-1 | 310822118 | STAUR_4871 |
| *Pseudomonas aeruginosa* PA7 | 152985298 | PSPA7_2994 |
| *Anaeromyxobacter* sp. K | 197121831 | AnaeK_1422 |
| *Maricaulis maris* MCS10 | 114569255 | Mmar10_0704 |
| *Anaeromyxobacter dehalogenans* 2CP-1 | 220916623 | A2cp1_1517 |
| *Burkholderia cenocepacia* J2315 | 206559589 | BCAL1212 |
| *Pseudomonas brassicacearum* subsp. *brassicacearum* NFM421 | 330810242 | PSEBR_a3378 |
| *Brucella melitensis* bv. 1 str. 16M | 17989093 | BMEII0748 |
| *Shewanella baltica* OS195 | 160875312 | Sbal195_2199 |
| *Burkholderia* sp. 383 | 78065831 | Bcep18194_A4360 |
| *Haliangium ochraceum* DSM 14365 | 262196423 | Hoch_3237 |
| *Variovorax paradoxus* S110 | 239814017 | Vapar_1010 |

TABLE 2-continued bkdA1 Genes

| Genome | Gene ID# | Locus Tag |
|---|---|---|
| *Achromobacter xylosoxidans* A8 | 311105811 | AXYL_02629 |
| *Ruegeria* sp. TM1040 | 99082618 | TM1040_2778 |
| *Pseudoalteromonas haloplanktis* TAC125 | 77360573 | PSHAa1632 |
| *Pseudomonas fluorescens* Pf0-1 | 77459685 | Pfl01_3463 |
| *Sphingobium japonicum* UT26S | 294011285 | SJA_C1-12990 |
| *Shewanella* sp. W3-18-1 | 120598931 | Sputw3181_2123 |
| *Waddlia chondrophila* WSU 86-1044 | 297620705 | wcw_0464 |
| *Shewanella baltica* OS223 | 217973406 | Sbal223_2235 |
| *Rubrobacter xylanophilus* DSM 9941 | 108805282 | Rxyl_2480 |
| *Idiomarina loihiensis* L2TR | 56460781 | IL1680 |
| *Caulobacter* sp. K31 | 167645834 | Caul_1870 |
| *Shewanella pealeana* ATCC 700345 | 157962067 | Spea_2246 |
| *Agrobacterium* sp. H13-3 | 332716274 | AGROH133_11609 |
| *Shewanella amazonensis* SB2B | 119774845 | Sama_1709 |
| *Brucella abortus* S19 | 189022867 | BAbS19_II06670 |
| *Novosphingobium* sp. PP1Y | 334142274 | PP1Y_AT28841 |
| *Burkholderia mallei* NCTC 10229 | 124381521 | BMA10229_1322 |
| *Burkholderia thailandensis* E264 | 83717236 | BTH_II2304 |
| *Halomonas elongata* DSM 2581 | 307544960 | HELO_2370 |
| *Pseudomonas aeruginosa* LESB58 | 218891779 | PLES_30571 |
| *Sinorhizobium fredii* NGR234 | 227823512 | NGR_c29890 |
| *Alteromonas macleodii* str. 'Deep ecotype' | 332141378 | MADE_1009900 |
| *Brucella microti* CCM 4915 | 256015303 | BMI_II518 |
| *Sphingopyxis alaskensis* RB2256 | 103486817 | Sala_1331 |
| *Shewanella* sp. ANA-3 | 117920575 | Shewana3_2131 |
| *Shewanella putrefaciens* CN-32 | 146292983 | Sputcn32_1885 |
| *Burkholderia pseudomallei* K96243 | 53723291 | BPSS2273 |
| *Burkholderia mallei* ATCC 23344 | 53716061 | BMAA2013 |
| *Burkholderia cenocepacia* AU 1054 | 107022318 | Bcen_0762 |
| *Pseudomonas aeruginosa* UCBPP-PA14 | 116050194 | PA14_35530 |
| *Thermoplasma volcanium* GSS1 | 13540933 | TVN0102 |
| *Pseudomonas entomophila* L48 | 104782857 | PSEEN3853 |
| *Burkholderia cenocepacia* MC0-3 | 170732566 | Bcenmc03_1216 |
| *Burkholderia cenocepacia* HI2424 | 116689265 | Bcen2424_1243 |
| *Alteromonas* sp. SN2 | 333893048 | ambt_07965 |
| *Shewanella* sp. MR-4 | 113970365 | Shewmr4_2028 |
| *Brucella melitensis* biovar Abortus 2308 | 83269598 | BAB2_0715 |
| *Ramlibacter tataouinensis* TTB310 | 337278681 | Rta_10480 |
| *Ochrobactrum anthropi* ATCC 49188 | 153010872 | Oant_3551 |
| *Erythrobacter litoralis* HTCC2594 | 85373858 | ELI_05155 |
| *Pseudomonas putida* GB-1 | 167034957 | PputGB1_3962 |
| *Burkholderia ambifaria* AMMD | 115351176 | Bamb_1123 |
| *Sinorhizobium medicae* WSM419 | 150398024 | Smed_2826 |
| *Anaeromyxobacter* sp. Fw109-5 | 153004855 | Anae109_1993 |
| *Pusillimonas* sp.T7-7 | 332284089 | PT7_0836 |
| *Shewanella piezotolerans* WP3 | 212635405 | swp_2606 |
| *Rhodoferax ferrireducens* T118 | 89902318 | Rfer_3554 |
| *Glaciecola* sp. 4H-3-7 + YE-5 | 332306594 | Glaag_2232 |
| *Marinobacter aquaeolei* VT8 | 120554306 | Maqu_1382 |
| *Ferrimonas balearica* DSM 9799 | 308050068 | Fbal_2358 |
| *Sinorhizobium meliloti* AK83 | 334317690 | Sinme_2988 |
| *Pseudomonas putida* W619 | 170722905 | PputW619_3742 |

TABLE 3 bkdA2 genes

| Genome | Gene ID# | Locus Tag |
|---|---|---|
| *Arthrobacter* sp. FB24 | 116669943 | Arth_1382 |
| *Stigmatella aurantiaca* DW4/3-1 | 310822117 | STAUR_4870 |
| *Chlamydia trachomatis* G/9301 | 385242630 | CTG9301_01750 |
| *Glaciecola nitratireducens* FR1064 | 348029316 | GNIT_1900 |
| *Chlamydia psittaci* NJ1 | 406593263 | B712_0357 |
| *Listeria monocytogenes* SLCC2479 | 405758053 | LMOSLCC2479_1066 |
| *Pseudonocardia dioxanivorans* CB1190 | 331700311 | Psed_6609 |

TABLE 3-continued

| bkdA2 genes | | |
|---|---|---|
| Genome | Gene ID# | Locus Tag |
| *Belliella baltica* DSM 15883 | 390941876 | Belba_0214 |
| *Staphylococcus aureus* subsp. *aureus* T0131 | 384870059 | SAT0131_01610 |
| *Mycoplasma bovis* HB0801 | 392429694 | Mbov_0103 |
| *Listeria ivanovii* subsp. *ivanovii* PAM 55 | 347548454 | LIV_0998 |
| *Muricauda ruestringensls* DSM 13258 | 344204449 | Murru_3149 |
| *Lactococcus garvieae* ATCC 49156 | 347520637 | LCGT_0031 |
| *Salinibacter ruber* M8 | 294506482 | SRM_00667 |
| *Chlamydia trachomatis* F/SW5 | 389859784 | FSW5_3451 |
| *Listeria monocytogenes* M7 | 386026370 | LMM7_1083 |
| *Bacillus subtilis* subsp. *subtilis* str. RO-NN-1 | 384176023 | I33_2482 |
| *Listeria monocytogenes* SLCC7179 | 404413140 | LMOSLCC7179_1034 |
| *Sinorhizobium fredii* HH103 | 378827584 | SFHH103_02999 |
| *Alteromonas macleodii* ATCC 27126 | 406596862 | MASE_09535 |
| *Staphylococcus aureus* subsp. *aureus* M013 | 379021299 | M013TW_1532 |
| *Bacteroides fragilis* 638R | 375357937 | BF638R_1637 |
| *Mycobacterium chubuense* NBB4 | 392417338 | Mycch_3528 |
| *Enterococcus hirae* ATCC 9790 | 392989735 | EHR_12860 |
| *Streptomyces bingchenggensis* BCW-1 | 374988200 | SBI_05444 |
| *Pseudomonas fluorescens* F113 | 378950263 | PSF113_2345 |
| *Staphylococcus aureus* subsp. *aureus* 11819-97 | 385781802 | MS7_1534 |
| *Staphylococcus aureus* subsp. *aureus* LGA251 | 387780609 | SARLGA251_14230 |
| *Staphylococcus aureus* subsp. *aureus* VC40 | 379014725 | SAVC_06830 |
| *Streptomyces* sp. SirexAA-E | 345000792 | SACTE_3240 |
| *Staphylococcus aureus* subsp. *aureus* FD133 | 384547750 | SAOV_1517 |
| *Mycoplasma bovis* Hubel-1 | 339320624 | MMB_0097 |
| *Sinorhizobium meliloti* SM11 | 384537525 | SM11_chr3105 |
| *Granulicella mallensis* MP5ACTX8 | 374310265 | AciX8_1322 |
| *Lactococcus garvieae* Lg2 | 385832000 | LCGL_0031 |
| *Chlamydia trachomatis* Sweden2 | 386262693 | SW2_3451 |
| *Paenibacillus polymyxa* M1 | 386041287 | PPM_2597 |
| *Bacillus amyloliquefaciens* LL3 | 384164972 | LL3_02590 |
| *Chlamydia psittaci* CP3 | 406592170 | B711_0381 |
| *Listeria monocytogenes* J0161 | 386046715 | LMOG_00667 |
| *Lactobacillus casei* BD-II | 385823210 | LCBD_1514 |
| *Listeria monocytogenes* SLCC5850 | 404410298 | LMOSLCC5850_1059 |
| *Melissococcus plutonius* DAT561 | 379727537 | MPD5_0997 |
| *Pyrobaculum oguniense* TE7 | 379004029 | Pogu_1067 |
| *Chlamydia trachomatis* E/SW3 | 389858908 | ESW3_3451 |
| *Nocardiopsis alba* ATCC BAA-2165 | 403509181 | B005_1702 |
| *Chlamydia trachomatis* F/SW4 | 389858032 | FSW4_3451 |
| *Listeria monocytogenes* SLCC2540 | 405755132 | LMOSLCC2540_1053 |
| *Staphylococcus aureus* subsp. *aureus* 71193 | 386729217 | ST398NM01_1582 |
| *Brucella suis* VBI22 | 376278493 | BSVBI22_B0519 |
| *Synechocystis* sp. PCC 6803 substr. PCC-N | 383490833 | SYNPCCN_0870 |
| *Mycobacterium massiliense* str. GO 06 | 397680860 | MYCMA_2661 |
| *Listeria monocytogenes* L99 | 386007777 | lmo4a_1062 |
| *Exiguobacterium antarcticum* B7 | 407477698 | Eab7_1859 |
| *Listeria monocytogenes* SLCC2376 | 404407509 | LMOSLCC2376_1026 |
| *Ignavibacterium album* JCM 16511 | 385810230 | IALB_1650 |
| *Staphylococcus lugdunensis* N920143 | 385784340 | SLUG_13960 |
| *Bacillus amyloliquefaciens* subsp. *plantarum* YAU B9601-Y2 | 384266014 | BANAU_2384 |

TABLE 3-continued bkdA2 genes

| Genome | Gene ID# | Locus Tag |
|---|---|---|
| *Chlamydia trachomatis* G/11074 | 385246240 | G11074_01750 |
| *Corynebacterium variabile* DSM 44702 | 340793900 | CVAR_0937 |
| *Niastella koreensis* GR20-10 | 375149638 | Niako_6452 |
| *Bacteriovorax marinus* SJ | 374289801 | BMS_3178 |
| *Mycoplasma pneumoniae* FH | 385326972 | MPNE_0454 |
| *Lactobacillus rhamnosus* GG NC_017482 | 385827987 | LRHM_1267 |
| *Shewanelle baltica* BA175 | 386324711 | Sbal175_2269 |
| *Acidithiobacillus caldus* SM-1 | 340782068 | Atc_1326 |
| *Streptomyces cattleya* NRRL 8057 = DSM 46488 NC_017586 | 386356697 | SCATT_30500 |
| *Brucella melitensis* M5-90 | 384213035 | BM590_B0497 |
| *Chlamydia trachomatis* D-EC | 385243547 | CTDEC_0340 |
| *Staphylococcus pseudintermedius* ED99 | 386319228 | SPSE_1284 |
| *Lactobacillus casei* LC2W | 385820009 | LC2W_1479 |
| *Bacillus amyloliquefaciens* subsp. *plantarum* CAU B946 | 375362935 | BACAU_2245 |
| *Alteromonas macleodii* str. 'English Channel 673' | 407683853 | AMEC673_09780 |
| *Staphylococcus aureus* subsp. *aureus* ECT-R 2 | 384864739 | ECTR2_1368 |
| *Mycoplasma genitalium* M2288 | 402552594 | CM5_01605 |
| *Aequorivita sublithincola* DSM 14238 | 390955426 | Aeqsu_2718 |
| *Streptomyces hygroscopicus* subsp. *jingnangensis* 5008 | 386841339 | SHJG_5256 |
| *Actinoplanes missouriensis* 431 | 383775247 | AMIS_770 |
| *Chlamydia trachomatis* A2497 NC_016798 | 376282346 | CTR_3381 |
| *Thermus* sp. CCB_US3_UF1 | 384439515 | TCCBUS3UF1_11210 |
| *Listeria monocytogenes* serotype 7 str. SLCC2482 | 404286467 | LMOSLCC2482_1100 |
| *Staphylococcus aureus* subsp. *aureus* TCH60 | 384867510 | HMPREF0772_11624 |
| *Lactobacillus rhamnosus* ATCC 8530 | 385835175 | LRHK_1311 |
| *Marinobacter hydrocarbonoclasticus* ATCC 49840 | 387814425 | MARHY2010 |
| *Pseudomonas aeruginosa* NCGM2.S1 | 386066186 | NCGM2_3257 |
| *Bacillus amyloliquefaciens* TA208 | 384160048 | BAMTA208_12325 |
| *Pseudomonas fluorescens* A506 | 387894500 | PflA506_3338 |
| *Alteromonas macleodii* str. 'Balearic Sea AD45' | 407687776 | AMBAS45_09985 |
| *Sinorhizobium meliloti* BL225C | 384530815 | SinmeB_2763 |
| *Mycoplasma hyopneumoniae* 168 | 385334342 | MHP168_185 |
| *Thermus thermophilus* JL-18 | 386359630 | T1JL18_0173 |
| *Listeria monocytogenes* SLCC2378 | 405752275 | LMOSLCC2378_1071 |
| *Listeria monocytogenes* Finland 1998 | 386053324 | LMLG_2335 |
| *Leuconostoc* sp. C2 | 339490188 | LGMK_00030 |
| *Shewanella baltica* OS117 | 386341193 | Sbal117_2344 |
| *Brucella melitensis* NI | 384446661 | BMNI_II0490 |
| *Lactobacillus buchneri* CD034 | 406026601 | LBUCD034_0782 |
| *Brucella canis* HSK A52141 | 376276774 | BCA52141_II0442 |
| *Bacillus amyloliquefaciens* XH7 | 384169111 | BAXH7_02513 |
| *Pseudomonas aeruginosa* M18 | 386058855 | PAM18_2792 |
| *Enterococcus faecium* Aus0004 | 383328412 | EFAU004_01093 |
| *Tetragenococcus halophilus* NBRC 12172 | 352517702 | TEH_15280 |
| *Terriglobus roseus* DSM 18391 | 390958199 | Terro_2360 |
| *Terriglobus roseus* DSM 18391 | 390957858 | Terro_1994 |
| *Deinococcus gobiensis* I-0 | 386855294 | DGo_CA0086 |
| *Mycoplasma genitalium* M6320 | 402552088 | CM1_01650 |
| *Staphylococcus aureus* 04-02981 | 387150660 | SA2981_1475 |
| *Saprospira grandis* str. Lewin | 379730055 | SGRA_1936 |
| *Chlamydia trachomatis* A2497 NC_017437 | 385270024 | CTO_0369 |
| *Staphylococcus aureus* subsp. *aureus* HO 5096 0412 | 386831127 | SAEMRSA15_14370 |
| *Paenibacillus mucilaginosus* 3016 | 379723636 | PM3016_5961 |
| *Pseudomonas putida* S16 | 339488699 | PPS_3806 |

TABLE 3-continued bkdA2 genes

| Genome | Gene ID# | Locus Tag |
|---|---|---|
| *Shewanella baltica* OS678 | 378708519 | Sbal678_2204 |
| *Chlamydia trachomatis* E/150 | 385245317 | E150_01785 |
| *Mycoplasma genitallum* M6282 | 402551583 | CM3_01735 |
| *Alteromonas macleodii* str. 'Black Sea 11' | 407700101 | AMBLS11_09280 |
| *Arthrobacter* sp. Rue61a | 403526503 | ARUE_c14360 |
| *Chlamydia trachomatis* G/9768 | 385239854 | G9768_01750 |
| *Lactobacillus salivarius* CECT 5713 | 385839942 | HN6_00131 |
| *Thermus thermophilus* SG0.5JP17-16 | 384430364 | Ththe16_0161 |
| *Chlamydla trachomatis* G/11222 | 385240777 | G11222_01755 |
| *Marinobacter adhaerens* HP15 | 385329804 | HP15_63 |
| *Burkholderia cepacia* GG4 | 402566978 | GEM_2216 |
| *Synechocystis* sp. PCC 6803 substr. PCC-P | 383324949 | SYNPCCP_0870 |
| *Streptomyces flavogriseus* ATCC 33331 | 357412428 | Sfla_3226 |
| *Actinoplanes* sp. SE50/110 | 386845148 | ACPL_194 |
| *Synechocystis* sp. PCC 6803 substr. GT-I | 383321780 | SYNGTI_0871 |
| *Brucella melitensis* M28 | 384410136 | BM28_B0498 |
| *Listeria monocytogenes* 10403S | 386043379 | LMRG_00515 |
| *Sphingobium* sp. SYK-6 | 347527351 | SLG_09660 |
| *Enterococcus faecium* DO | 389868409 | HMPREF0351_11226 |
| *Paenibacillus mucilaginosus* K02 | 386726385 | B2K_30300 |
| *Enterococcus faecalis* 62 | 384518455 | EF62_1805 |
| *Listeria monocytogenes* ATCC 19117 | 405749410 | LMOATCC19117_1075 |
| *Listeria monocytogenes* FSL R2-561 | 386049981 | LMKG_01869 |
| *Streptomyces violaceusniger* Tu 4113 | 345008026 | Strvi_0312 |
| *Pseudomonas putida* DOT-T1E | 397697835 | T1E_5100 |
| *Burkholderia pseudomallei* 1026b | 386866106 | BP1026B_II2447 |
| *Staphylococcus aureus* subsp. *aureus* str. JKD6008 | 384862119 | SAA6008_01486 |
| *Listeria monocytogenes* 07PF0776 | 386731808 | MUO_05540 |
| *Paenibacillus terrae* HPL-003 | 374323888 | HPL003_20280 |
| *Mycoplasma pneumoniae* 309 | 377822707 | MPNA3920 |
| *Staphylococcus aureus* subsp. *aureus* S0385 | 387602857 | SAPIG1582 |
| *Staphylococcus aureus* subsp. *aureus* TW20 | 387143124 | SATW20_15130 |
| *Oceanimonas* sp. GK1 | 374335113 | GU3_06470 |
| *Shewanella putrefaciens* 200 | 386313861 | Sput200_2105 |
| *Brucella pinnipedialis* B2/94 | 340792253 | BPI_II506 |
| | 384223055 | BS1330_II0520 |
| *Chlamydia trachomatls* D-LC | 385244427 | CTDLC_0340 |
| *Kitasatospora setae* KM-6054 | 357390777 | KSE_38660 |
| *Pelagibacterium halotolerans* B2 | 357384138 | KKY_1078 |
| *Sinorhizobium fredii* USDA257 | 398355222 | USDA257_c54060 |
| *Enterococcus faecalis* D32 | 397699743 | EFD32_1166 |
| *Bacillus amyloliquefaciens* Y2 | 387899033 | MUS_2694 |
| *Chlamydia trachomatis* L2c | 339626009 | CTL2C_951 |
| *Leuconostoc mesenteroides* subsp. *mesenteroides* J18 | 381336327 | MI1_03380 |
| *Chlamydia trachomatis* E/11023 | 385241710 | E11023_01775 |
| *Melioribacter roseus* P3M | 397691247 | MROS_2258 |
| *Mycoplasma genitalium* M2321 | 402551095 | CM9_01625 |
| *Akkermansia muciniphila* ATCC BAA-835 | 187735388 | Amuc_0886 |
| *Mycoplasma crocodyli* MP145 | 294155659 | MCRO_0411 |
| *Acidobacterium* sp. MP5ACTX9 | 322435297 | Aclx9_1679 |
| *Shewanella woodyi* ATCC 51908 | 170726629 | Swoo_2279 |
| *Shewanella denitrificans* OS217 | 91793143 | Sden_1787 |
| *Nitratifractor salsuginis* DSM 16511 | 319956742 | Nitsa_0997 |
| *Prochlorococcus marinus* subsp. *marinus* str. CCMP1375 | 33240216 | Pro0766 |
| *Shewanella oneidensis* MR-1 | 24373887 | SO_2340 |
| *Lactobacillus sakei* subsp. *sakei* 23K | 81428694 | LSA1084 |
| Aster yellows witches'-broom phytoplasma AYWB | 85057417 | AYWB_137 |

TABLE 3-continued bkdA2 genes

| Genome | Gene ID# | Locus Tag |
|---|---|---|
| *Shewanella halifaxensis* HAW-EB4 | 167624157 | Shal_2233 |
| *Anaeromyxobacter dehalogenans* 2CP-C | 86158250 | Adeh_1826 |
| *Parachlamydia acanthamoebae* UV7 | 338174252 | PUV_02580 |
| *Rhodococcus erythropolis* PR4 | 226307480 | RER_39930 |
| *Paenibacillus* sp. JDR-2 | 251796660 | Pjdr2_2651 |
| *Listeria seeligeri* serovar 1/2b str. SLCC3954 | 289434314 | lse_0947 |
| *Agrobacterium tumefaciens* str. C58 | 15891465 | Atu_3472 |
| *Pseudoalteromonas atlantica* T6c | 109898354 | Patl_2037 |
| *Chlamydia muridarum* Nigg | 15835233 | TC0618 |
| *Pseudomonas fluorescens* SBW25 | 229591397 | PFLU3965 |
| *Sorangium cellulosum* 'So ce 56' | 162449841 | sce1570 |
| *Melissococcus plutonius* ATCC 35311 | 332686440 | MPTP_0946 |
| *Pseudomonas fluorescens* Pf-5 | 70729901 | PFL_2533 |
| *Bacillus subtilis* subsp. *spizizenii* str. W23 | 305675052 | BSUW23_11885 |
| *Oceanithermus profundus* DSM 14977 | 313680638 | Ocepr_1751 |
| *Bradyrhizoblum Japonicum* USDA 110 | 27381443 | blr6332 |
| *Lactobacillus salivarius* UCC118 | 90961136 | LSL_0154 |
| *Paenibacillus mucilaginosus* KNP414 | 337750577 | KNP414_06348 |
| *Croceibacter atlanticus* HTCC2559 | 298208751 | CA2559_10943 |
| *Brucella melitensis* ATCC 23457 | 225686317 | BMEA_B0498 |
| *Gramella forsetii* KT0803 | 120435970 | GFO_1616 |
| *Arthrobacter arilaitensis* Re117 | 308176762 | AARI_09800 |
| *Candidatus Koribacter versatilis* Ellin345 | 94968813 | Acid345_1786 |
| *Deinococcus deserti* VCD115 | 226357395 | Deide_23450 |
| *Chloroflexus* sp. Y-400-fl | 222525095 | Chy400_1833 |
| *Stackebrandtia nassauensis* DSM 44728 | 291303508 | Snas_6069 |
| *Pseudomonas putida* KT2440 | 26991091 | PP_4402 |
| *Synechococcus* sp. JA-2-3B'a(2-13) | 86609223 | CYB_1765 |
| *Shewanella loihica* PV-4 | 127512854 | Shew_1926 |
| *Synechococcus* sp. JA-3-3Ab | 86606954 | CYA_2326 |
| *Shewanella baltica* OS185 | 153000674 | Shew185_2150 |
| *Enterococcus faecalis* V583 | 29375921 | EF1354 |
| *Staphylococcus epidermidis* RP62A | 57866997 | SERP1077 |
| *Staphylococcus aureus* subsp. *aureus* JH9 | 148268001 | SaurJH9_1575 |
| *Mycoplasma pneumoniae* M129 | 13508131 | MPN392 |
| *Staphylococcus aureus* subsp. *aureus* COL | 57650473 | SACOL1561 |
| *Staphylococcus epidermidis* ATCC 12228 | 27468115 | SE1197 |
| *Thermus thermophilus* HB8 | 55980199 | TTHA0230 |
| *Brucella suis* 1330 | 23500272 | BRA0525 |
| *Aeropyrum pernix* K1 | 14601550 | APE_1674 |
| *Microbacterium testaceum* StLB037 | 323360061 | MTES_3613 |
| Onion yellows phytoplasma OY-M | 39939087 | PAM_601 |
| *Marinomonas* sp. MWYL1 | 152997133 | Mmwyl1_3123 |
| *Renibacterium salmoninarum* ATCC 33209 | 163839305 | RSal33209_0547 |
| *Beutenbergia cavernae* DSM 12333 | 229822443 | Bcav_3966 |
| *Burkholderia pseudomallei* 1106a | 126455889 | BURPS1106A_A3066 |
| *Mesorhizobium ciceri* biovar biserrulae WSM1271 | 319780621 | Mesci_0882 |
| *Arthrobacter phenanthrenivorans* Sphe3 | 325962775 | Asphe3_13730 |
| *Streptomyces scabiei* 87.22 | 290958943 | SCAB_45171 |
| *Exiguobacterium* sp. AT1b | 229916237 | EAT1b_0506 |
| *Deinococcus proteolyticus* MRP | 325284178 | Deipr_1971 |
| *Polaromonas* sp. JS666 | 91786185 | Bpro_0274 |

TABLE 3-continued

| bkdA2 genes | | |
|---|---|---|
| Genome | Gene ID# | Locus Tag |
| *Streptomyces cattleya* NRRL 8057 = DSM 46488 NC_016111 | 357400644 | SCAT_3060 |
| *Mycoplasma conjunctivae* HRC/581 | 240047197 | MCJ_000680 |
| *Burkholderia glumae* BGR1 | 238023733 | bglu_2g02650 |
| *Alicycliphilus denitrificans* BC | 319761348 | Alide_0629 |
| *Staphylococcus aureus* subsp. *aureus* USA300_TCH1516 | 161509745 | USA300HOU_1518 |
| *Brucella abortus* A13334 | 376271256 | BAA13334_II01344 |
| *Alicycliphilus denitrificans* K601 | 330823223 | Alide2_0594 |
| *Chlamydia trachomatis* 434/Bu | 166154552 | CTL0594 |
| *Burkholderia pseudomallei* 668 | 126444265 | BURPS668_A3192 |
| *Burkholderia gladioli* BSR3 | 330819431 | bgla_2g03050 |
| *Staphylococcus aureus* subsp. *aureus* MSSA476 | 49486353 | SAS1455 |
| *Sphingomonas wittichii* RW1 | 148555059 | Swit_2144 |
| *Staphylococcus lugdunensis* HKU09-01 | 289550713 | SLGD_01399 |
| *Pseudoalteromonas* sp. SM9913 | 315126680 | PSM_A1604 |
| *Brucella suis* ATCC 23445 | 163844683 | BSUIS_B0520 |
| *Truepera radiovictrix* DSM 17093 | 297622991 | Trad_0747 |
| *Mycoplasma pulmonis* UAB CTIP | 15829234 | MYPU_7630 |
| *Micromonospora aurantiaca* ATCC 27029 | 302864656 | Micau_0148 |
| *Prochlorococcus marinus* str. MIT 9303 | 124023323 | P9303_16211 |
| *Shewanella sediminis* HAW-EB3 | 157375465 | Ssed_2328 |
| *Listeria innocua* Clip11262 | 16800114 | lin1045 |
| *Chitinophaga pinensis* DSM 2588 | 256419854 | Cpin_0808 |
| *Mycoplasma hyopneumoniae* 7448 | 72080456 | MHP7448_0116 |
| *Pseudomonas putida* F1 | 148546692 | Pput_1452 |
| *Brucella abortus* bv. 1 str. 9-941 | 62317614 | BruAb2_0699 |
| *Burkholderia mallei* SAVP1 | 121597989 | BMASAVP1_1035 |
| *Pseudomonas aeruginosa* DK2 | 392984203 | PADK2_14035 |
| *Frankia alni* ACN14a | 111219575 | FRAAL0070 |
| *Brevundimonas subvibrioides* ATCC 15264 | 302384436 | Bresu_3330 |
| *Sphingobium chlorophenolicum* L-1 | 334344848 | Sphch_1204 |
| *Shewanella* sp. MR-7 | 114047444 | Shewmr7_1948 |
| *Hahella chejuensis* KCTC 2396 | 83646415 | HCH_03686 |
| *Shewanella violacea* DSS12 | 294140814 | SVI_2043 |
| *Staphylococcus carnosus* subsp. *carnosus* TM300 | 224476625 | Sca_1138 |
| *Bacteroides fragilis* NCTC 9343 | 60681130 | BF1636 |
| *Novosphingobium aromaticivorans* DSM 12444 | 87199992 | Saro_1975 |
| *Deinococcus geothermalis* DSM 11300 | 94986436 | Dgeo_2339 |
| *Cyanothece* sp. ATCC 51142 | 172039560 | cce_4647 |
| *Pseudomonas putida* ND6 | 395447959 | YSA_07992 |
| *Leuconostoc gasicomitatum* LMG 18811 | 300173681 | LEGAS_1380 |
| *Intrasporangium calvum* DSM 43043 | 317123421 | Intca_0249 |
| *Thermus thermophilus* HB27 | 46200058 | TTC1756 |
| *Burkholderia ambifaria* MC40-6 | 172060190 | BamMC406_1135 |
| *Chloroflexus aggregans* DSM 9485 | 219848986 | Cagg_2096 |
| *Burkholderia pseudomallei* 1710b | 76818778 | BURPS1710b_A1410 |
| *Mycoplasma agalactiae* | 291320032 | MAGa1010 |
| | 404489824 | BLi02581 |
| *Shewanella frigidimarina* NCIMB 400 | 114563107 | Sfri_1936 |
| *Staphylococcus aureus* subsp. *aureus* MSHR1132 | 379795877 | SAMSHR1132_13570 |
| *Staphylococcus aureus* subsp. *aureus* ED98 | 269203146 | SAAV_1509 |
| *Hirschia baltica* ATCC 49814 | 254293977 | Hbal_1615 |
| *Thermoplasma acidophilum* DSM 1728 | 16082406 | Ta1437 |
| *Mesorhizobium opportunistum* WSM2075 | 337265441 | Mesop_0912 |
| *Sinorhizobium meliloti* 1021 | 15966686 | SMc03202 |
| *Salinispora tropica* CNB-440 | 145592674 | Strop_0108 |
| *Burkholderia mallei* NCTC 10247 | 126446124 | BMA10247_A2301 |

TABLE 3-continued

| bkdA2 genes | | |
|---|---|---|
| Genome | Gene ID# | Locus Tag |
| *Bdellovibrio bacteriovorus* HD100 | 42522536 | Bd0974 |
| *Shewanella baltica* OS155 | 126174437 | Sbal_2221 |
| *Candidatus Phytoplasma mali* | 194246556 | ATP_00155 |
| Frankia symbiont of *Datisca glomerata* | 336180266 | FsymDg_4471 |
| *Candidatus Phytoplasma australiense* | 197294721 | PAa_0687 |
| *Staphylococcus pseudintermedius* HKU10-03 | 319892499 | SPSINT_1210 |
| *Bordetella petrii* DSM 12804 | 163857823 | Bpet3510 |
| *Deinococcus maricopensis* DSM 21211 | 320333704 | Deima_1097 |
| *Listeria monocytogenes* L312 | 406703829 | LMOL312_1054 |
| *Verrucosispora maris* AB-18-032 | 330464990 | VAB18032_05035 |
| *Brucella canis* ATCC 23365 | 161620587 | BCAN_B0523 |
| *Brucella ovis* ATCC 25840 | 148558303 | BOV_A0456 |
| *Colwellia psychrerythraea* 34H | 71277818 | CPS_1583 |
| *Mesorhizobium loti* MAFF303099 | 13473768 | mll4472 |
| *Cellulomonas fimi* ATCC 484 | 332671066 | Celf_2562 |
| *Pseudomonas putida* BIRD-1 | 386011041 | PPUBIRD1_1440 |
| *Maribacter* sp. HTCC2170 | 305666956 | FB2170_11881 |
| *Pyrobaculum calidifontis* JCM 11548 | 126460012 | Pcal_1404 |
| *Stigmatella aurantiaca* DW4/3-1 | 310822117 | STAUR_4870 |
| *Staphylococcus aureus* subsp. *aureus* MRSA252 | 49483766 | SAR1594 |
| *Mycoplasma agalactiae* PG2 | 148377362 | MAG_0940 |
| *Pseudomonas aeruginosa* PA7 | 152988941 | PSPA7_2993 |
| *Lactobacillus buchneri* NRRL B-30929 | 331701105 | Lbuc_0737 |
| *Photorhabdus asymbiotica* | 253990152 | PAU_02673 |
| *Staphylococcus aureus* subsp. *aureus* Mu3 | 156979835 | SAHV_1504 |
| *Staphylococcus aureus* subsp. *aureus* JKD6159 | 384550344 | SAA6159_01452 |
| *Bacillus amyloliquefaciens* DSM 7 | 308174192 | BAMF_2301 |
| *Anaeromyxobacter* sp. K | 197122440 | AnaeK_2034 |
| *Maricaulis maris* MCS10 | 114569256 | Mmar10_0705 |
| *Anaeromyxobacter dehalogenans* 2CP-1 | 220917207 | A2cp1_2104 |
| *Burkholderia cenocepacia* J2315 | 206559590 | BCAL1213 |
| *Pseudomonas brassicacearum* subsp. *brassicacearum* NFM421 | 330810243 | PSEBR_a3379 |
| *Staphylococcus aureus* subsp. *aureus* Mu50 | 15924506 | SAV1516 |
| *Lactobacillus rhamnosus* Lc 705 | 258539526 | LC705_01335 |
| *Rhodococcus opacus* B4 | 226360693 | ROP_12790 |
| *Leuconostoc kimchii* IMSNU 11154 | 296110720 | LKI_02945 |
| *Brucella melitensis* bv. 1 str. 16M | 17989092 | BMEII0747 |
| *Shewanella baltica* OS195 | 160875313 | Sbal195_2200 |
| *Staphylococcus aureus* subsp. *aureus* NCTC 8325 | 88195323 | SAOUHSC_01612 |
|  | 16330037 | sll1721 |
| *Cellulophaga algicola* DSM 14237 | 319955314 | Cetal_3836 |
| *Leuconostoc citreum* KM20 | 170016783 | LCK_00425 |
| *Burkholderia* sp. 383 | 78065832 | Bcep18194_A4361 |
| *Marivirga tractuosa* DSM 4126 | 313676905 | Ftrac_2815 |
| *Haliangium ochraceum* DSM 14365 | 262196422 | Hoch_3236 |
| *Synechocystis* sp. PCC 6803 | 384436100 | SYNGTS_0871 |
| *Variovorax paradoxus* S110 | 239814018 | Vapar_1011 |
| *Achromobacter xylosoxidans* A8 | 311105812 | AXYL_02630 |
| *Ruegeria* sp. TM1040 | 99082617 | TM1040_2777 |
| *Arthrobacter chlorophenolicus* A6 | 220912170 | Achl_1400 |
| *Chloroflexus aurantiacus* J-10-fl | 163847254 | Caur_1692 |
| *Haliscomenobacter hydrossis* DSM 1100 | 332665004 | Halhy_3056 |
| *Pseudoalteromonas haloplanktis* TAC125 | 77360572 | PSHAa1631 |
| *Thermoproteus uzoniensis* 768-20 | 327310924 | TUZN_1028 |
| *Pseudomonas fluorescens* Pf0-1 | 77459686 | Pfl01_3464 |
| *Lactobacillus casei* ATCC 334 | 116494795 | LSEI_1306 |
| *Lactobacillus casei* str. Zhang | 301066361 | LCAZH_1300 |

TABLE 3-continued

| bkdA2 genes | | |
|---|---|---|
| Genome | Gene ID# | Locus Tag |
| Sphingobium japonicum UT26S | 294011286 | SJA_C1-13000 |
| Cyanothece sp. PCC 8801 | 218247666 | PCC8801_2883 |
| Shewanella sp. W3-18-1 | 120598930 | Sputw3181_2122 |
| Propionibacterium freudenreichii subsp. shermanII CIRM-BIA1 | 297625421 | PFREUD_02200 |
| Bacillus subtilis subsp. subtilis str. 168 | 16079460 | BSU24040 |
| Nocardiopsis dassonvillei subsp. dassonvillei DSM 43111 | 297564330 | Ndas_5418 |
| Waddlia chondrophila WSU 86-1044 | 297620706 | wcw_0465 |
| Shewanella baltica OS223 | 217973405 | Sbal223_2234 |
| Frankia sp. Ccl3 | 86738780 | Francci3_0057 |
| Bacillus licheniformis ATCC 14580 | 52080942 | BL01505 |
| Idiomarina loihiensis L2TR | 56460780 | IL1679 |
| Cellulomonas flavigena DSM 20109 | 296131225 | Cfla_3399 |
| Bacillus clausii KSM-K16 | 56964215 | ABC2450 |
| Caulobacter sp. K31 | 167645835 | Caul_1871 |
| Enterococcus faecalis OG1RF | 384513106 | OG1RF_11142 |
| Thermobaculum terrenum ATCC BAA-798 | 269925215 | Tter_0094 |
| Roseiflexus castenholzii DSM 13941 | 156743005 | Rcas_3062 |
| Prochlorococcus marinus str. MIT 9313 | 33862891 | PMT0618 |
| Shewanella pealeana ATCC 700345 | 157962066 | Spea_2245 |
| Agrobacterium sp. H13-3 | 332716273 | AGROH133_11608 |
| Rhodococcus equi 103S | 312139113 | REQ_16940 |
| Shewanella amazonensis SB2B | 119774846 | Sama_1710 |
| Bacillus cellulosilyticus DSM 2522 | 317129371 | Bcell_2667 |
| Brucella abortus S19 | 189022866 | BAbS19_II06660 |
| Novosphingobium sp. PP1Y | 334142273 | PP1Y_AT28832 |
| Listeria monocytogenes HCC23 | 217964854 | LMHCC_1574 |
| Leuconostoc mesenteroides subsp. mesenteroides ATCC 8293 | 116617850 | LEUM_0738 |
| Thermobifida fusca YX | 72160585 | Tfu_0181 |
| Deinococcus radiodurans R1 | 15805071 | DR_0030 |
| Burkholderia mallei NCTC 10229 | 124382700 | BMA10229_1321 |
| Burkholderia thailandensis E264 | 83716737 | BTH_II2303 |
| Pedobacter heparinus DSM 2366 | 255533705 | Phep_3824 |
| Halomonas elongata DSM 2581 | 307544961 | HELO_2371 |
| Pseudomonas aeruginosa LESB58 | 218891778 | PLES_30561 |
| Sinorhizobium fredii NGR234 | 227823513 | NGR_c29900 |
| Alteromonas macleodii str. 'Deep ecotype' | 332141379 | MADE_1009905 |
| Brucella microti CCM 4915 | 256015304 | BMI_II519 |
| Meiothermus ruber DSM 1279 | 291296694 | Mrub_2321 |
| Sphingopyxis alaskensis RB2256 | 103486816 | Sala_1330 |
| Chlamydia trachomatis B/TZ1A828/OT | 237804687 | CTB_3381 |
| Chlamydia trachomatis D/UW-3/CX | 15605063 | CT340 |
| Listeria monocytogenes serotype 4b str. F2365 | 46907285 | LMOf2365_1074 |
| Mycoplasma genitalium G37 | 12045129 | MG_273 |
| Shewanella sp. ANA-3 | 117920574 | Shewana3_2130 |
| Shewanella putrefaciens CN-32 | 146292984 | Sputcn32_1886 |
| Burkholderia pseudomallei K96243 | 53723290 | BPSS2272 |
| Synechococcus sp. PCC 7002 | 170077278 | SYNPCC7002_A0655 |
| Mycobacterium ulcerans Agy99 | 118619019 | MUL_3774 |
| Arthrobacter aurescens TC1 | 119960874 | AAur_1522 |
| Burkholderia mallei ATCC 23344 | 53716062 | BMAA2012 |
| Saccharomonospora viridis DSM 43017 | 257057824 | Svir_38870 |
| Mycobacterium sp. MCS | 108800591 | Mmcs_3625 |
| Staphylococcus aureus subsp. aureus JH1 | 150394068 | SaurJH1_1608 |
| Burkholderia cenocepacia AU 1054 | 107022319 | Bcen_0763 |

TABLE 3-continued bkdA2 genes

| Genome | Gene ID# | Locus Tag |
|---|---|---|
| *Meiothermus silvanus* DSM 9946 | 297565575 | Mesil_1135 |
| *Chlamydia trachomatis* L2b/UCH-1/proctitis | 166155427 | CTLon_0592 |
| *Parabacteroides distasonis* ATCC 8503 | 150007337 | BDI_0687 |
| *Staphylococcus haemolyticus* JCSC1435 | 70726400 | SH1399 |
| *Lactobacillus fermentum* IFO 3956 | 184155615 | LAF_1139 |
| *Bacillus amyloliquefaciens* FZB42 | 154686663 | RBAM_022320 |
| *Staphylococcus aureus* subsp. *aureus* MW2 | 21283198 | MW1469 |
| *Frankia* sp. EAN1pec | 158318985 | Franean1_7268 |
| *Pseudomonas aeruginosa* UCBPP-PA14 | 116050195 | PA14_35520 |
| *Thermoplasma volcanium* GSS1 | 13540932 | TVN0101 |
| *Paenibacillus polymyxa* E681 | 308069294 | PPE_02531 |
| *Lactobacillus casei* BL23 | 191638310 | LCABL_15370 |
| *Pseudomonas entomophila* L48 | 104782858 | PSEEN3854 |
| *Terriglobus saanensis* SP1PR4 | 320107218 | AciPR4_2010 |
| *Staphylococcus aureus* subsp. *aureus* USA300_FPR3757 | 87160136 | SAUSA300_1465 |
| *Lactobacillus rhamnosus* GG NC_013198 | 258508316 | LGG_01321 |
| *Staphylococcus aureus* RF122 | 82751121 | SAB1389c |
| *Burkholderia cenocepacia* MC0-3 | 170732567 | Bcenmc03_1217 |
| *Thermus scotoductus* SA-01 | 320449332 | TSC_c02390 |
| *Paracoccus denitrificans* PD1222 | 119384344 | Pden_1604 |
| *Thermomonospora curvata* DSM 43183 | 269124599 | Tcur_0329 |
| *Burkholderia cenocepacia* HI2424 | 116689266 | Bcen2424_1244 |
| *Oenococcus oeni* PSU-1 | 116490425 | OEOE_0329 |
| *Roseiflexus* sp. RS-1 | 148656538 | RoseRS_2416 |
| *Listeria monocytogenes* 08-5578 | 284801385 | LM5578_1136 |
| *Alteromonas* sp. SN2 | 333893049 | ambt_07970 |
| *Shewanella* sp. MR-4 | 113970364 | Shewmr4_2027 |
| *Streptomyces avermitilis* MA-4680 | 29830920 | SAV_4377 |
| *Staphylococcus aureus* subsp. *aureus* N315 | 15927097 | SA1347 |
| *Bacteroides fragilis* YCH46 | 53712912 | BF1622 |
| *Thermobispora bispora* DSM 43833 | 296271282 | Tbis_3331 |
| *Paenibacillus* sp. Y412MC10 | 261406246 | GYMC10_2402 |
| *Erysipelothrix rhusiopathiae* str. Fujisawa | 336066645 | ERH_1409 |
| *Pyrobaculum arsenaticum* DSM 13514 | 145591407 | Pars_1188 |
| *Mycoplasma bovis* PG45 | 313678231 | MBOVPG45_0105 |
| *Brucella melitensis* biovar Abortus 2308 | 83269597 | BAB2_0714 |
| *Rhodococcus jostii* RHA1 | 111018576 | RHA1_ro01577 |
| *Ramlibacter tataouinensis* TTB310 | 337278682 | Rta_10490 |
| *Ochrobactrum anthropi* ATCC 49188 | 153010873 | Oant_3552 |
| *Erythrobacter litoralis* HTCC2594 | 85373859 | ELI_05160 |
| *Bacillus subtilis* BSn5 | 321311885 | BSn5_02555 |
| *Pseudomonas putida* GB-1 | 167034958 | PputGB1_3963 |
| *Actinosynnema mirum* DSM 43827 | 256379011 | Amir_5002 |
| *Cyanothece* sp. PCC 7822 | 307152588 | Cyan7822_2730 |
| *Mycobacterium* sp. KMS | 119869730 | Mkms_3698 |
| *Burkholderia ambifaria* AMMD | 115351177 | Bamb_1124 |
| *Sinorhizobium medicae* WSM419 | 150398025 | Smed_2827 |
| *Mycobacterium vanbaalenii* PYR-1 | 120405039 | Mvan_4085 |
| *Chloroherpeton thalassium* ATCC 35110 | 193214148 | Ctha_0429 |
| *Lysinibacillus sphaericus* C3-41 | 169826944 | Bsph_1364 |
| *Salinibacter ruber* DSM 13855 | 83816020 | SRU_0576 |
| *Bacteroides thetaiotaomicron* VPI-5482 | 29345722 | BT_0312 |
| *Chlamydia trachomatis* A/HAR-13 | 76789066 | CTA_0369 |
| *Anaeromyxobacter* sp. Fw109-5 | 153004856 | Anae109_1994 |
| *Chlamydia trachomatis* B/Jali20/OT | 237802765 | JALI_3381 |

TABLE 3-continued bkdA2 genes

| Genome | Gene ID# | Locus Tag |
|---|---|---|
| *Simkania negevensis* Z | 338732442 | SNE_A05470 |
| *Acidobacterium capsulatum* ATCC 51196 | 225874704 | ACP_3156 |
| *Micromonospora* sp. L5 | 315500949 | ML5_0131 |
| *Listeria monocytogenes* EGD-e | 16803093 | lmo1053 |
| *Cyanothece* sp. PCC 8802 | 257060998 | Cyan8802_3213 |
| *Prochlorococcus marinus* str. MIT 9211 | 159903256 | P9211_07151 |
| *Carnobacterium* sp. 17-4 | 328957242 | CAR_c09190 |
| *Saccharopolyspora erythraea* NRRL 2338 | 134100488 | SACE_3953 |
| *Pusillimonas* sp. T7-7 | 332284090 | PT7_0837 |
| *Synechococcus elongatus* PCC 6301 | 56751371 | syc1362_d |
| *Shewanella piezotolerans* WP3 | 212635404 | swp_2605 |
| *Streptosporangium roseum* DSM 43021 | 271970151 | Sros_8973 |
| *Paenibacillus polymyxa* SC2 | 310642336 | PPSC2_c2888 |
| 'Nostoc azollae' 0708 | 298492752 | Aazo_4540 |
| *Rhodoferax ferrireducens* T118 | 89902317 | Rfer_3553 |
| *Streptomyces griseus* subsp. *griseus* NBRC 13350 | 182437559 | SGR_3766 |
| *Pyrobaculum aerophilum* str. IM2 | 18313490 | PAE2646 |
| *Mycobacterium abscessus* ATCC 19977 | 169631990 | MAB_4917c |
| *Salinispora arenicola* CNS-205 | 159035781 | Sare_0108 |
| *Listeria monocytogenes* 08-5923 | 284994527 | LM5923_1090 |
| *Sphaerobacter thermophilus* DSM 20745 | 269929376 | Sthe_3476 |
| *Mycoplasma hyopneumoniae* 232 | 54020422 | mhp264 |
| *Marinithermus hydrothermalis* DSM 14884 | 328950234 | Marky_0709 |
| *Herpetosiphon aurantiacus* ATCC 23779 | 159899111 | Haur_2592 |
| *Listeria weishimeri* serovar 6b str. SLCC5334 | 116872447 | lwe1029 |
| *Glaciecola* sp. 4H-3-7 + YE-5 | 332306593 | Glaag_2231 |
| *Cellulophaga lytica* DSM 7489 | 325287820 | Celly_2922 |
| *Mycoplasma hyopneumoniae* J | 71893469 | MHJ_0112 |
| *Marinobacter aquaeolei* VT8 | 120554305 | Maqu_1381 |
| *Mycobacterium* sp. JLS | 126436207 | Mjls_3630 |
| *Picrophilus torridus* DSM 9790 | 48477620 | PTO0548 |
| *Staphylococcus aureus* subsp. *aureus* str. Newman | 151221634 | NWMN_1422 |
| *Ferrimonas balearica* DSM 9799 | 308050067 | Fbal_2357 |
| *Listeria monocytogenes* serotype 4b str. CLIP 80459 | 226113671 | Lm4b_01073 |
| *Sinorhizobium meliloti* AK83 | 334317691 | Sinme_2989 |
| *Pseudomonas putida* W619 | 170722906 | PputW619_3743 |

TABLE 4 bkdB genes

| Genome | Gene ID# | Locus Tag |
|---|---|---|
| *Stigmatella aurantiaca* DW4/3-1 | 310821917 | STAUR_4868 |
| *Mycoplasma putrefaciens* KS1 | 344205274 | MPUT_0557 |
| *Spirochaeta thermophila* DSM 6578 | 386347079 | Spith_1347 |
| *Glaciecola nitratireducens* FR1064 | 348029315 | GNIT_1899 |
| *Chlamydia psittaci* NJ1 | 406593425 | B712_0521 |
| *Listeria monocytogenes* SLCC2479 | 405758054 | LMOSLCC2479_1067 |
| *Bacillus coagulans* 36D1 | 347750662 | Bcoa_0221 |
| *Desulfosporosinus orientis* DSM 765 | 374996775 | Desor_4331 |
| *Streptococcus suis* D9 | 386584873 | SSUD9_1864 |
| *Lactococcus lactis* subsp. *cremoris* NZ9000 | 389853269 | LLNZ_00355 |
| *Staphylococcus aureus* subsp. *aureus* T0131 | 384869628 | SAT0131_01132 |
| *Sulfobacillus acidophilus* TPY | 339629489 | TPY_3237 |
| *Listeria ivanovii* subsp. *ivanovii* PAM 55 | 347548455 | LIV_0999 |
| *Corallococcus coralloides* DSM 2259 | 383455711 | COCOR_03727 |
| *Streptococcus suis* ST1 | 389857346 | SSUST1_1724 |
| *Mycoplasma hyorhinis* MCLD | 385858736 | SRH_03265 |
| *Listeria monocytogenes* M7 | 386026371 | LMM7_1084 |
| *Zymomonas mobilis* subsp. *mobilis* ATCC 10988 | 384411955 | Zmob_1035 |
| *Bacillus subtilis* subsp. *subtilis* str. RO-NN-1 | 384175196 | I33_1640 |

TABLE 4-continued bkdB genes

| Genome | Gene ID# | Locus Tag |
|---|---|---|
| Listeria monocytogenes SLCC7179 | 404413141 | LMOSLCC7179_1035 |
| Sinorhizobium fredii HH103 | 378827585 | SFHH103_03000 |
| Alteromonas macleodii ATCC 27126 | 406596863 | MASE_09540 |
| Sulfobacillus acidophilus DSM 10332 | 379007393 | Sulac_1676 |
| Staphylococcus aureus subsp. aureus M013 | 379020802 | M013TW_1027 |
| Mycoplasma gallisepticum str. R (high) | 385325594 | MGAH_0162 |
| Bacteroides fragilis 638R | 375357936 | BF638R_1636 |
| Chlamydophila psittaci 02DC15 | 384454502 | CPS0B_0520 |
| Haloferax mediterranei ATCC 33500 | 389848366 | HFX_2954 |
| Chlamydophila psittaci 01DC11 | 384451574 | CPS0A_0523 |
| Mycobacterium canettii CIPT 140010059 | 340627509 | MCAN_25341 |
| Mycoplasma hyorhinis GDL-1 | 378835985 | MYM_0544 |
| Mycoplasma leachii 99/014/6 | 392388985 | MLEA_004800 |
| Streptomyces bingchenggensis BCW-1 | 374988188 | SBI_05432 |
| Mycobacterium tuberculosis UT205 | 392387133 | UDA_2495c |
| Pseudomonas fluorescens F113 | 378950262 | PSF113_2344 |
| Staphylococcus aureus subsp. aureus 11819-97 | 385781323 | MS7_1052 |
| Staphylococcus aureus subsp. aureus LGA251 | 387780208 | SARLGA251_10080 |
| Staphylococcus aureus subsp. aureus VC40 | 379014288 | SAVC_04635 |
| Streptomyces sp. SirexAA-E | 345000808 | SACTE_3256 |
| Staphylococcus aureus subsp. aureus ED133 | 384547281 | SAOV_1039 |
| Cardinium endosymbiont cPer1 of Encarsia pergandiella | 406024948 | CAHE_0047 |
| Flavobacterium branchiophilum FL-15 | 347536377 | FBFL15_1500 |
| Methanocella conradii HZ254 | 383320309 | Mtc_1892 |
| Sinorhizobium meliloti SM11 | 384537526 | SM11_chr3106 |
| Pyrobaculum sp. 1860 | 374327309 | P186_1853 |
| Acetobacter pasteurianus IFO 3283-12 | 384042231 | APA12_12160 |
| Paenibacillus polymyxa M1 | 386041286 | PPM_2596 |
| Bacillus amyloliquefaciens LL3 | 384163956 | LL3_01566 |
| Chlamydia psittaci CP3 | 406592339 | B711_0552 |
| Mycobacterium tuberculosis CTRI-2 | 385999275 | MTCTRI2_2541 |
| Listeria monocytogenes J0161 | 386046716 | LMOG_00666 |
| Bacillus megaterium WSH-002 | 384048055 | BMWSH_3882 |
| Lactobacillus casei BD-II | 385823211 | LCBD_1515 |
| Acetobacter pasteurianus IFO 3283-26 | 384059731 | APA26_12160 |
| Listeria monocytogenes SLCC5850 | 404410299 | LMOSLCC5850_1060 |
| Pyrobaculum oguniense TE7 | 379004030 | Pogu_1068 |
| Amycolatopsis mediterranei S699 NC_017186 | 384152886 | RAM_38890 |
| Thermococcus sp. 4557 | 341582347 | GQS_06320 |
| Streptococcus macedonicus ACA-DC 198 | 374337769 | SMA_0798 |
| Nocardiopsis alba ATCC BAA-2165 | 403509526 | B005_2061 |
| Bacillus cereus NC7401 | 375285965 | BCN_3871 |
| Listeria monocytogenes SLCC2540 | 405755133 | LMOSLCC2540_1054 |
| Staphylococcus aureus subsp. aureus 71193 | 386728775 | ST398NM01_1092 |
| Brucella suis VBI22 | 376278494 | BSVBI22_B0520 |
| Mycobacterium tuberculosis RGTB327 | 383308271 | MRGA327_15390 |
| Mycobacterium massiliense str. GO 06 | 397678695 | MYCMA_0457 |
| Listeria monocytogenes L99 | 386000778 | lmo4a_1063 |
| Exiguobacterium antarcticum B7 | 407477697 | Eab7_1858 |
| Rhodothermus marinus SG0.5JP17-172 | 345303310 | Rhom172_1451 |
| Listeria monocytogenes SLCC2376 | 404407510 | LMOSLCC2376_1027 |
| Leptospira interrogans serovar Lai str. IPAV | 386074087 | LIF_A1623 |
| Acetobacter pasteurianus IFO 3283-22 | 384057090 | APA22_12160 |
| Mycobacterium tuberculosis RGTB423 | 386005399 | MRGA423_15610 |
| Staphylococcus lugdunensis N920143 | 385784712 | SLUG_17750 |
| Bacillus amyloliquefaciens subsp. plantarum YAU B9601-Y2 | 384265011 | BANAU_1381 |
| Mycobacterium tuberculosis H37Rv | 397674399 | RVBD_2495c |
| Mycoplasma pneumoniae FH | 385326971 | MPNE_0453 |
| Mycobacterium bovis BCG str. Mexico | 378772231 | BCGMEX_2507c |
| Lactobacillus rhamnosus GG NC_017482 | 385827988 | LRHM_1268 |
| Shewanella baltica BA175 | 386324710 | Sbal175_2268 |
| Streptococcus infantarius subsp. infantarius CJ18 | 379705200 | Sinf_0850 |
| Streptomyces cattleya NRRL 8057 = DSM 46488 NC_017586 | 386356696 | SCATT_30490 |
| Streptococcus suis GZ1 | 386578648 | SSGZ1_1656 |
| Geobacillus thermoleovorans CCB_US3_UF5 | 375008018 | GTCCBUS3UF5_12370 |
| Brucella melitensis M5-90 | 384213036 | BM590_B0498 |
| Staphylococcus pseudintermedius ED99 | 386319627 | SPSE_1696 |
| Lactobacillus casei LC2W | 385820010 | LC2W_1480 |
| Bacillus amyloliquefaciens subsp. plantarum CAU B946 | 375362108 | BACAU_1418 |
| Alteromonas macleodii str. 'English Channel 673' | 407683854 | AMEC673_09785 |
| Chlamydophila psittaci C19/98 | 384453523 | CPS0C_0525 |
| Staphylococcus aureus subsp. aureus ECT-R 2 | 384864322 | ECTR2_950 |
| Streptococcus agalactiae GD201008-001 | 406709369 | A964_0883 |
| Streptococcus thermophilus ND03 | 386086666 | STND_0986 |
| Streptococcus gallolyticus subsp. gallolyticus ATCC 43143 | 386337523 | SGGB_0854 |
| Streptomyces hygroscopicus subsp. jinggangensis 5008 | 386841328 | SHJG_5245 |
| Thermus sp. CCB_US3_UF1 | 384440433 | TCCBUS3UF1_20450 |
| Listeria monocytogenes serotype 7 str. SLCC2482 | 404286468 | LMOSLCC2482_1101 |
| Streptococcus suis S735 | 403062262 | YYK_07845 |
| Staphylococcus aureus subsp. aureus TCH60 | 384868023 | HMPREF0772_12137 |
| Lactobacillus rhamnosus ATCC 8530 | 385835176 | LRHK_1312 |
| Pseudomonas aeruginosa NCGM2.S1 | 386066187 | NCGM2_3258 |

TABLE 4-continued bkdB genes

| Genome | Gene ID# | Locus Tag |
|---|---|---|
| *Bacillus anthracis* str. H9401 | 386737860 | H9401_3987 |
| *Bacillus amyloliquefaciens* TA208 | 384159556 | BAMTA208_09845 |
| *Pseudomonas fluorescens* A506 | 387894501 | PflA506_3339 |
| *Chlamydophila psittaci* 6BC | 384450574 | G5O_0512 |
| *Alteromonas macleodii* str. 'Balearic Sea AD45' | 407687777 | AMBAS45_09990 |
| *Sinorhizobium meliloti* BL225C | 384530816 | SinmeB_2764 |
| *Bacillus* sp. JS | 386758176 | MY9_1599 |
| *Mycoplasma hyopneumoniae* 168 | 385334664 | MHP168_513 |
| *Thermus thermophilus* JL-18 | 386359627 | TtJL18_0170 |
| *Listeria monocytogenes* SLCC2378 | 405752276 | LMOSLCC2378_1072 |
| *Listeria monocytogenes* Finland 1998 | 386053325 | LMLG_2963 |
| *Acetobacter pasteurianus* IFO 3283-03 | 384050748 | APA03_12160 |
| *Leuconostoc* sp. C2 | 339490189 | LGMK_00035 |
| *Shewanella baltica* OS117 | 386341192 | Sbal117_2343 |
| *Brucella melitensis* NI | 384446662 | BMNI_II0491 |
| *Oscillibacter valericigenes* Sjm18-20 | 350270533 | OBV_21370 |
| *Lactococcus lactis* subsp. *cremoris* A76 | 385837009 | llh_0200 |
| *Mycoplasma gallisepticum* str. F | 385326188 | MGF_2592 |
| *Mycobacterium africanum* GM041182 | 339632521 | MAF_25100 |
| *Alicyclobacillus acidocaldarius* subsp. *acidocaldarius* Tc-4-1 | 384134351 | TC41_0586 |
| *Lactobacillus buchneri* CD034 | 406026602 | LBUCD034_0783 |
| *Brucella canis* HSK A52141 | 376276773 | BCA52141_II0441 |
| *Bacillus amyloliquefaciens* XH7 | 384168610 | BAXH7_02008 |
| *Pseudomonas aeruginosa* M18 | 386058854 | PAM18_2791 |
| *halophilic archaeon* DL31 | 345006003 | Halar_2851 |
| *Deinococcus gobiensis* I-0 | 386855296 | DGo_CA0088 |
| *Acetobacter pasteurianus* IFO 3283-07 | 384053856 | APA07_12160 |
| *Mycoplasma genitalium* M6320 | 402552087 | CM1_01645 |
| *Staphylococcus aureus* 04-02981 | 387150237 | SA2981_1052 |
| *Mycoplasma gallisepticum* WI01_2001.043-13-2P | 401769395 | HFMG01WIA_3531 |
| *Mycoplasma gallisepticum* VA94_7994-1-7P | 401766360 | HFMG94VAA_3682 |
| *Staphylococcus aureus* subsp. *aureus* HO 5096 0412 | 386830631 | SAEMRSA15_09250 |
| *Paenibacillus mucilaginosus* 3016 | 379723635 | PM3016_5960 |
| *Pseudomonas putida* S16 | 339488700 | PPS_3807 |
| *Amycolatopsis mediterranei* S699 V2 NC_018266 | 399541273 | AMES_7457 |
| *Shewanella baltica* OS678 | 378708520 | Sbal678_2205 |
| *Streptococcus suis* A7 | 386588918 | SSUA7_1659 |
| *Micavibrio aeruginosavorus* ARL 13 | 347758064 | MICA_1302 |
| *Alteromonas macleodii* str. 'Black Sea 11' | 407700102 | AMBLS11_09285 |
| *Arthrobacter* sp. Rue61a | 403526504 | ARUE_c14370 |
| *Lactobacillus salivarius* CECT 5713 | 385839943 | HN6_00132 |
| *Thermus thermophilus* SG0.5JP17-16 | 384430361 | Ththe16_0158 |
| *Marinobacter adhaerens* HP15 | 385329805 | HP15_64 |
| *Mycoplasma gallisepticum* NC95_13295-2-2P | 401767116 | HFMG95NCA_3609 |
| *Burkholderia cepacia* GG4 | 402566977 | GEM_2215 |
| *Mycobacterium tuberculosis* KZN 605 | 392431895 | TBXG_001463 |
| *Streptomyces flavogriseus* ATCC 33331 | 357412429 | Sfla_3227 |
| *Brucella melitensis* M28 | 384410137 | BM28_B0499 |
| *Listeria monocytogenes* 10403S | 386043380 | LMRG_00516 |
| *Sphingobium* sp. SYK-6 | 347527352 | SLG_09670 |
| *Zymomonas mobilis* subsp. *mobilis* ATCC 29191 | 397676636 | ZZ6_0757 |
| *Mycoplasma gallisepticum* NC06_2006.080-5-2P | 401770149 | HFMG06NCA_3594 |
| *Bacillus thuringiensis* serovar *finitimus* YBT-020 | 384181787 | YBT020_19515 |
| *Bacillus cereus* F837/76 | 376267867 | bcf_19725 |
| *Paenibacillus mucilaginosus* K02 | 386726384 | B2K_30295 |
| *Mycobacterium tuberculosis* CCDC5079 | 385995424 | CCDC5079_2299 |
| *Listeria monocytogenes* ATCC 19117 | 405749411 | LMOATCC19117_1076 |
| *Listeria monocytogenes* FSL R2-561 | 386049982 | LMKG_01868 |
| *Natrinema* sp. J7-2 | 397771820 | NJ7G_0034 |
| *Streptomyces violaceusniger* Tu 4113 | 345008014 | Strvi_0300 |
| *Pseudomonas putida* DOT-T1E | 397697836 | T1E_5101 |
| *Burkholderia pseudomallei* 1026b | 386866105 | BP1026B_II2446 |
| *Staphylococcus aureus* subsp. *aureus* str. JKD6008 | 384861690 | SAA6008_01050 |
| *Listeria monocytogenes* 07PF0776 | 386731809 | MUO_05545 |
| *Solibacillus silvestris* StLB046 | 393201879 | SSIL_3152 |
| *Paenibacillus terrae* HPL-003 | 374323889 | HPL003_20285 |
| *Mycoplasma pneumoniae* 309 | 377822706 | MPNA3910 |
| *Streptococcus suis* D12 | 386586927 | SSUD12_1813 |
| *Streptococcus suis* JS14 | 386580721 | SSUJS14_1797 |
| *Staphylococcus aureus* subsp. *aureus* S0385 | 387602368 | SAPIG1092 |
| *Staphylococcus aureus* subsp. *aureus* TW20 | 387142707 | SATW20_10900 |
| *Oceanimonas* sp. GK1 | 374335114 | GU3_06475 |
| *Shewanella putrefaciens* 200 | 386313860 | Sput200_2104 |
| *Brucella pinnipedialis* B2/94 | 340792254 | BPI_II507 |
| | 384223056 | BS1330_II0521 |
| *Streptococcus thermophilus* JIM 8232 | 386344721 | STH8232_1236 |
| *Kitasatospora setae* KM-6054 | 357390884 | KSE_39730 |
| *Pelagibacterium halotolerans* B2 | 357384139 | KKY_1079 |
| *Mycobacterium tuberculosis* CCDC5180 | 385991805 | CCDC5180_2271 |
| *Sinorhizobium fredii* USDA 257 | 398355223 | USDA257_c54070 |
| *Enterococcus faecalis* D32 | 397699744 | EFD32_1167 |
| *Acetobacter pasteurianus* IFO 3283-01-42C | 384119099 | APA42C_12160 |
| *Bacillus amyloliquefaciens* Y2 | 387897996 | MUS_1555 |
| *Mycobacterium tuberculosis* KZN 4207 | 375295688 | TBSG_01487 |
| *Leuconostoc mesenteroides* subsp. *mesenteroides* J18 | 381336328 | MI1_03385 |
| *Solitalea canadensis* DSM 3403 | 387791039 | Solca_1867 |
| *Mycoplasma gallisepticum* NY01_2001.047-5-1P | 401768648 | HFMG01NYA_3671 |

TABLE 4-continued

| bkdB genes | | |
|---|---|---|
| Genome | Gene ID# | Locus Tag |
| *Mycoplasma genitalium* M2321 | 402551094 | CM9_01620 |
| *Caldicellulosiruptor saccharolyticus* DSM 8903 | 146295908 | Csac_0872 |
| *Mycoplasma crocodyli* MP145 | 294155660 | MCRO_0412 |
| *Shewanella woodyi* ATCC 51908 | 170726630 | Swoo_2280 |
| *Streptomyces coelicolor* A3(2) | 21222239 | SCO3829 |
| *Shewanella denitrificans* OS217 | 91793144 | Sden_1788 |
| *Prochlorococcus marinus* subsp. *marinus* str. CCMP1375 | 33239853 | Pro0401 |
| *Streptococcus suis* BM407 | 253756264 | SSUBM407_1708 |
| *Shewanella oneidensis* MR-1 | 24373888 | SO_2341 |
| *Bacillus anthracis* str. CDC 684 | 227816744 | BAMEG_4223 |
| *Lactobacillus sakei* subsp. *sakei* 23K | 81428693 | LSA1083 |
| Aster yellows witches'-broom phytoplasma AYWB | 85057418 | AYWB_138 |
| *Shewanella halifaxensis* HAW-EB4 | 167624156 | Shal_2232 |
| *Anaeromyxobacter dehalogenans* 2CP-C | 86158249 | Adeh_1825 |
| *Parachlamydia acanthamoebae* UV7 | 338174251 | PUV_02570 |
| *Rhodococcus erythropolis* PR4 | 226309469 | RER_59840 |
| *Bacillus halodurans* C-125 | 15615216 | BH2653 |
| *Paenibacillus* sp. JDR-2 | 251796661 | Pjdr2_2652 |
| *Listeria seeligeri* serovar 1/2b str. SLCC3954 | 289434315 | lse_0948 |
| *Agrobacterium tumefaciens* str. C58 | 159185753 | Atu3471 |
| *Pseudoalteromonas atlantica* T6c | 109898355 | Patl_2038 |
| *Chlamydia muridarum* Nigg | 15835136 | TC0518 |
| *Pseudomonas fluorescens* SBW25 | 229591398 | PFLU3966 |
| *Sorangium cellulosum* 'Soce 56' | 162449840 | sce1569 |
| *Halopiger xanaduensis* SH-6 | 336252525 | Halxa_1119 |
| *Melissococcus plutonius* ATCC 35311 | 332686441 | MPTP_0947 |
| *Synechococcus* sp. CC9605 | 78213526 | Syncc9605_2009 |
| *Streptococcus suis* 98HAH33 | 146321685 | SSU98_1838 |
| *Pseudomonas fluorescens* Pf-5 | 70729900 | PFL_2532 |
| *Bacillus subtilis* subsp. *spizizenii* str. W23 | 305674187 | BSUW23_07510 |
| *Rhodospirillum centenum* SW | 209963468 | RC1_0121 |
| *Bradyrhizobium japonicum* USDA 110 | 27381444 | blr6333 |
| *Lactobacillus salivarius* UCC118 | 90961137 | LSL_0155 |
| Wolbachia endosymbiont of *Culex quinquefasciatus* Pel | 190571193 | WPa_0791 |
| *Paenibacillus mucilaginosus* KNP414 | 337750576 | KNP414_06347 |
| *Haloferax volcanii* DS2 | 292657068 | HVO_2960 |
| *Brucella melitensis* ATCC 23457 | 225686318 | BMEA_B0499 |
| *Lactobacillus reuteri* DSM 20016 | 148543865 | Lreu_0633 |
| *Bacillus pumilus* SAFR-032 | 157692138 | BPUM_1357 |
| *Bacillus cereus* G9842 | 218899126 | BCG9842_B1167 |
| *Streptococcus agalactiae* NEM316 | 25010951 | gbs0897 |
| *Chloroflexus* sp. Y-400-fl | 222524728 | Chy400_1455 |
| *Pseudomonas putida* KT2440 | 26991092 | PP_4403 |
| *Synechococcus* sp. JA-2-3B'a(2-13) | 86608594 | CYB_1116 |
| *Haloterrigena turkmenica* DSM 5511 | 284166851 | Htur_3595 |
| *Shewanella lohica* PV-4 | 127512855 | Shew_1927 |
| *Mycobacterium tuberculosis* H37Ra | 148662331 | MRA_2521 |
| *Synechococcus* sp. JA-3-3Ab | 86605452 | CYA_0742 |
| *Shewanella baltica* OS185 | 153000675 | Shew185_2151 |
| *Enterococcus faecalis* V583 | 29375922 | EF1355 |
| *Staphylococcus epidermidis* RP62A | 57866608 | SERP0682 |
| *Staphylococcus aureus* subsp. *aureus* JH9 | 148267588 | SaurJH9_1155 |
| *Mycoplasma pneumoniae* M129 | 13508130 | MPN391 |
| *Staphylococcus aureus* subsp. *aureus* COL | 57651704 | SACOL1104 |
| *Staphylococcus epidermidis* ATCC 12228 | 27467711 | SE0793 |
| *Thermus thermophilus* HB8 | 55980201 | TTHA0232 |
| *Brucella suis* 1330 | 23500273 | BRA0526 |
| *Aeropyrum pernix* K1 | 14601549 | APE_1671 |
| *Microbacterium testaceum* StLB037 | 323358111 | MTES_1663 |
| *Gemmatimonas aurantiaca* T 27 | 226227399 | GAU_1993 |
| *Bacillus cereus* AH820 | 218905101 | BCAH820_3985 |
| Onion yellows phytoplasma OY-M | 39939088 | PAM_602 |
| *Thermaerobacter marianensis* DSM 12885 | 317122504 | Tmar_1671 |
|  | 332287420 | CPSIT_0516 |
| *Mycoplasma leachii* PG50 | 313665161 | MSB_A0275 |
| *Burkholderia pseudomallei* 1106a | 126456596 | BURPS1106A_A3065 |
| *Leifsonia xyli* subsp. *xyli* str. CTCB07 | 50955930 | Lxx25050 |
| *Treponema azotonutricium* ZAS-9 | 333995417 | TREAZ_3439 |
| *Geobacillus* sp. Y412MC61 | 261419258 | GYMC61_1834 |
| *Mesorhizobium ciceri* biovar biserrulae WSM1271 | 319780622 | Mesci_0883 |
| *Arthrobacter phenanthrenivorans* Sphe3 | 325964389 | Asphe3_30510 |
| *Streptomyces scabiei* 87.22 | 290958955 | SCAB_45291 |
| *Exiguobacterium* sp. AT1b | 229918500 | EAT1b_2787 |
| Wolbachia endosymbiont strain TRS of *Brugia malayi* | 58585004 | Wbm0747 |
| *Lactobacillus plantarum* subsp. *plantarum* ST-III | 308180958 | LPST_C1776 |
| *Ilyobacter polytropus* DSM 2926 | 310779675 | Ilyop_1889 |
| *Bacillus anthracis* str. Ames | 30264042 | BA_4182 |
| *Polaromonas* sp. JS666 | 91786186 | Bpro_0275 |
| *Streptomyces cattleya* NRRL 8057 = DSM 46488 NC_016111 | 357400643 | SCAT_3059 |
| *Halobacterium* sp. NRC-1 | 15791042 | VNG2219G |
| *Chlamydophila psittaci* RD1 | 392376657 | Cpsi_4681 |
| *Mycoplasma conjunctivae* HRC/581 | 240047198 | MCJ_000690 |
| *Bacillus cereus* E33L | 52141519 | BCZK3729 |
| *Coprothermobacter proteolyticus* DSM 5265 | 206896349 | COPRO5265_0853 |
| *Mycobacterium tuberculosis* KZN 1435 | 253798425 | TBMG_01476 |
| *Geobacillus thermodenitrificans* NG80-2 | 138894594 | GTNG_0924 |
| *Burkholderia glumae* BGR1 | 238023734 | bglu_2g02660 |
| *Alicycliphilus denitrificans* BC | 319761349 | Alide_0630 |
| *Staphylococcus aureus* subsp. *aureus* USA300_TCH1516 | 161509278 | USA300HOU_1038 |

TABLE 4-continued bkdB genes

| Genome | Gene ID# | Locus Tag |
|---|---|---|
| *Bacillus thuringiensis* str. Al Hakam | 118479182 | BALH_3593 |
| *Bacillus thuringiensis* serovar chinensis CT-43 | 384188034 | CT43_CH3976 |
| *Brucella abortus* A13334 | 376271255 | BAA13334_II01343 |
| *Bacillus thuringiensis* serovar konkukian str. 97-27 | 49481607 | BT9727_3713 |
| *Fluviicola taffensis* DSM 16823 | 327403295 | Fluta_1300 |
| *Alicycliphilus denitrificans* K601 | 330823224 | Alide2_0595 |
| *Geobacillus thermoglucosidasius* C56-YS93 | 336236213 | Geoth_2861 |
| *Alicyclobacillus acidocaldarius* subsp. *acidocaldarius* DSM 446 | 258510469 | Aaci_0455 |
| *Prochlorococcus marinus* str. MIT 9312 | 78778785 | PMT9312_0400 |
| *Streptococcus suis* 05ZYH33 | 146319493 | SSU05_1839 |
| *Anaerolinea thermophila* UNI-1 | 320160832 | ANT_14280 |
| *Bartonella tribocorum* CIP 105476 | 163868060 | Btr_0863 |
| *Burkholderia pseudomallei* 668 | 126445162 | BURPS668_A3191 |
| *Burkholderia gladioli* BSR3 | 330819432 | bgla_2g03060 |
| *Zymomonas mobilis* subsp. *mobilis* ZM4 | 56551406 | ZMO0510 |
| *Staphylococcus aureus* subsp. *aureus* MSSA476 | 49485933 | SAS1030 |
| *Sphingomonas wittichii* RW1 | 148553703 | Swit_0780 |
| *Staphylococcus lugdunensis* HKU09-01 | 289551093 | SLGD_01780 |
| *Chlamydophila pecorum* E58 | 330444490 | G5S_0830 |
| *Staphylococcus saprophyticus* subsp. *saprophyticus* ATCC 15305 | 73663003 | SSP1694 |
| *Natrialba magadii* ATCC 43099 | 289581338 | Nmag_1666 |
| *Pseudoalteromonas* sp. SM9913 | 315126679 | PSM_A1603 |
| *Nautilia profundicola* AmH | 224372801 | NAMH_0770 |
| *Brucella suis* ATCC 23445 | 163844684 | BSUIS_B0521 |
| *Prochlorococcus marinus* str. MIT 9301 | 126695762 | P9301_04241 |
| *Mycoplasma pulmonis* UAB CTIP | 15829233 | MYPU_7620 |
| *Micromonospora aurantiaca* ATCC 27029 | 302869527 | Micau_5080 |
| *Prochlorococcus marinus* str. MIT 9303 | 124023822 | P9303_21291 |
| *Shewanella sediminis* HAW-EB3 | 157375464 | Ssed_2327 |
| *Listeria innocua* Clip11262 | 16800115 | lin1046 |
| *Mycoplasma synoviae* 53 | 71894296 | MS53_0274 |
| *Bacillus cereus* ATCC 14579 | 30022059 | BC3971 |
| *Mycoplasma hyopneumoniae* 7448 | 72080837 | MHP7448_0506 |
| *Pseudomonas putida* F1 | 148546691 | Pput_1451 |
| *Brucella abortus* bv. 1 str. 9-941 | 62317613 | BruAb2_0698 |
| *Burkholderia mallei* SAVP1 | 121596563 | BMASAVP1_1034 |
| *Mesoplasma florum* L1 | 50364856 | Mfl041 |
| *Pseudomonas aeruginosa* DK2 | 392084202 | PADK2_14030 |
| *Mycoplasma penetrans* HF-2 | 26553962 | MYPE5100 |
| *Frankia alni* ACN14a | 111222643 | FRAAL3226 |
| *Brevundimonas subvibrioides* ATCC 15264 | 302384435 | Bresu_3329 |
| *Thermococcus sibiricus* MM 739 | 242399616 | TSIB_1641 |
| *Myxococcus fulvus* HW-1 | 338535470 | LILAB_29225 |
| *Modestobacter marinus* | 389866831 | MODMU_5238 |
| *Sphingobium chlorophenolicum* L-1 | 334342793 | Sphch_3287 |
| *Shewanella* sp. MR-7 | 114047445 | Shewmr7_1949 |
| *Hahella chejuensis* KCTC 2396 | 83646414 | HCH_03685 |
| *Shewanella violacea* DSS12 | 294140815 | SVI_2044 |
| *Mycobacterium bovis* AF2122/97 | 31793675 | Mb2523c |
| *Synechococcus* sp. CC9902 | 78184239 | Syncc9902_0662 |
| *Staphylococcus carnosus* subsp. *carnosus* TM300 | 224476210 | Sca_0721 |
| *Bacteroides fragilis* NCTC 9343 | 60681129 | BF1635 |
| *Lactobacillus fermentum* CECT 5716 | 385812453 | LC40_0741 |
| *Novosphingobium aromaticivorans* DSM 12444 | 87199991 | Saro_1974 |
| *Geobacillus* sp. WCH70 | 239826459 | GWCH70_0954 |
| *Geobacter* sp. M18 | 322421393 | GM18_3918 |
| *Deinococcus geothermalis* DSM 11300 | 94986438 | Dgeo_2341 |
| *Streptococcus suis* SC84 | 253752504 | SSUSC84_1660 |
| *Bacillus coagulans* 2-6 | 336113642 | BCO26_0964 |
| *Wolbachia* sp. wRi | 225630846 | WRi_011520 |
| *Streptococcus agalactiae* 2603V/R | 22537043 | SAG0880 |
| *Cyanothece* sp. ATCC 51142 | 172037663 | cce_2750 |
| *Desulfotalea psychrophila* LSv54 | 51245946 | DP2094 |
| *Desulfotomaculum carboxydivorans* CO 1 SRB | 333922988 | Desca_0775 |
| *Pseudomonas putida* ND6 | 395447958 | YSA_07990 |
| *Methanocella paludicola* SANAE | 282164389 | MCP_1719 |
| *Nocardia cyriacigeorgica* GUH-2 | 379707337 | NOCYR_1092 |
| *Leuconostoc gasicomitatum* LMG 18811 | 300173680 | LEGAS_1379 |
| *Intrasporangium calvum* DSM 43043 | 317123422 | Intca_0250 |
| *Streptococcus pasteurianus* ATCC 43144 | 336064058 | SGPB_0743 |
| *Thermus thermophilus* HB27 | 46200056 | TTC1754 |
| *Streptococcus thermophilus* LMD-9 | 116627818 | STER_1034 |
| *Mycoplasma mycoides* subsp. *mycoides* SC str. PG1 | 42560815 | MSC_0267 |
| *Burkholderia ambifaria* MC40-6 | 172060191 | BamMC406_1136 |
| *Burkholderia pseudomallei* 1710b | 76818033 | BURPS1710b_A1409 |
| *Mycobacterium avium* 104 | 118462619 | MAV_1677 |
|  | 404488950 | BLi01676 |
| *Shewanella frigidimarina* NCIMB 400 | 114563108 | Sfri_1937 |
| *Staphylococcus aureus* subsp. *aureus* MSHR1132 | 379795466 | SAMSHR1132_09420 |
| *Natronomonas pharaonis* DSM 2160 | 76800930 | NP0556A |
| *Staphylococcus aureus* subsp. *aureus* ED98 | 269202706 | SAAV_1060 |
| *Hirschia baltica* ATCC 49814 | 254293978 | Hbal_1616 |
| *Streptococcus thermophilus* CNRZ1066 | 55823000 | str1049 |
| *Thermoplasma acidophilum* DSM 1728 | 16082405 | Ta1436 |
| *Bacillus selenitireducens* MLS10 | 297583900 | Bsel_1604 |
| *Mesorhizobium opportunistum* WSM2075 | 337265442 | Mesop_0913 |
| *Sinorhizobium meliloti* 1021 | 15966687 | SMc03203 |
| *Salinispora tropica* CNB-440 | 145594631 | Strop_2099 |
| *Burkholderia mallei* NCTC 10247 | 126446955 | BMA10247_A2300 |

TABLE 4-continued bkdB genes

| Genome | Gene ID# | Locus Tag |
|---|---|---|
| Desulfobulbus propionicus DSM 2032 | 320353605 | Despr_1499 |
| Bdellovibrio bacteriovorus HD100 | 42522358 | Bd0779 |
| Shewanella baltica OS155 | 126174436 | Sbal_2220 |
| Candidatus Phytoplasma mali | 194246555 | ATP_00154 |
| Halobacillus halophilus DSM 2266 | 386714109 | HBHAL_2810 |
| Candidatus Phytoplasma australiense | 197294722 | PAa_0688 |
| Geobacter bemidjiensis Bem | 197116859 | Gbem_0461 |
| Staphylococcus pseudintermedius HKU10-03 | 319892093 | SPSINT_0804 |
| Mycobacterium bovis BCG str. Tokyo 172 | 224990871 | JTY_2509 |
| Bordetella petrii DSM 12804 | 163857822 | Bpet3509 |
| Listeria monocytogenes L312 | 406703830 | LMOL312_1055 |
| Verrucosispora maris AB-18-032 | 330468694 | VAB18032_23695 |
| Brucella canis ATCC 23365 | 161620588 | BCAN_B0524 |
| Brucella ovis ATCC 25840 | 148558405 | BOV_A0457 |
| Bacillus anthracis str. 'Ames Ancestor' | 47529478 | GBAA_4182 |
| Caldicellulosiruptor kronotskyensis 2002 | 312622978 | Calkro_1928 |
| Colwellia psychrerythraea 34H | 71279590 | CPS_1584 |
| Pseudovibrio sp. FO-BEG1 | 374331640 | PSE_3294 |
| Acetobacter pasteurianus IFO 3283-01 | 258542310 | APA01_12160 |
| Mesorhizobium loti MAFF303099 | 13473767 | mll4471 |
| Propionibacterium acnes 6609 | 387504442 | TIB1ST10_10615 |
| Pseudomonas putida BIRD-1 | 386011040 | PPUBIRD1_1439 |
| Cyanothece sp. PCC 7424 | 218437448 | PCC7424_0443 |
| Pyrobaculum calidifontis JCM 11548 | 126460011 | Pcal_1403 |
| Stigmatella aurantiaca DW4/3-1 | 31082197 | STAUR_4668 |
| Staphylococcus aureus subsp. aureus MRSA252 | 49483258 | SAR1069 |
| Sanguibacter keddieii DSM 10542 | 269795189 | Sked_18850 |
| Pseudomonas aeruginosa PA7 | 152984679 | PSPA7_2992 |
| Lactobacillus buchneri NRRL B-30929 | 331701106 | Lbuc_0738 |
| Aerococcus urinae ACS-120-V-Col10a | 326803934 | HMPREF9243_1601 |
| Bacillus atrophaeus 1942 | 311067976 | BATR1942_05070 |
| | 15609632 | Rv2495c |
| Staphylococcus aureus subsp. aureus Mu3 | 156979418 | SAHV_1087 |
| Staphylococcus aureus subsp. aureus JKD6159 | 384549856 | SAA6159_00951 |
| Candidatus Sulcia muelleri DMIN | 293977962 | DMIN_02500 |
| Bacillus amyloliquefaciens DSM 7 | 308173426 | BAMF_1535 |
| Anaeromyxobacter sp. K | 197122441 | AnaeK_2035 |
| Isosphaera pallida ATCC 43644 | 320101969 | Isop_0416 |
| Maricaulis maris MCS10 | 114569257 | Mmar10_0706 |
| Anaeromyxobacter dehalogenans 2CP-1 | 220917208 | A2cp1_2105 |
| Burkholderia cenocepacia J2315 | 206559591 | BCAL1214 |
| Pseudomonas brassicacearum subsp. brassicacearum NFM421 | 330810244 | PSEBR_a3380 |
| Synechococcus sp. RCC307 | 148242893 | SynRCC307_1794 |
| Staphylococcus aureus subsp. aureus Mu50 | 15924085 | SAV1095 |
| Streptococcus thermophilus LMG 18311 | 55821074 | stu1049 |
| Lactobacillus rhamnosus Lc 705 | 258539527 | LC705_01336 |
| Leuconostoc kimchii IMSNU 11154 | 296110719 | LKI_02940 |
| Mycoplasma gallisepticum str. R (low) | 31544687 | MGA_0162 |
| Spirochaeta coccoides DSM 17374 | 330837592 | Spico_1653 |
| Brucella melitensis bv. 1 str. 16M | 17989091 | BMEII0746 |
| Shewanella baltica OS195 | 160875314 | Sbal195_2201 |
| Staphylococcus aureus subsp. aureus NCTC 8325 | 88194794 | SAOUHSC_01042 |
| Nitratiruptor sp. SB155-2 | 152990678 | NIS_0932 |
| Leuconostoc citreum KM20 | 170016784 | LCK_00426 |
| Burkholderia sp. 383 | 78065833 | Bcep18194_A4362 |
| Bacillus pseudofirmus OF4 | 288553329 | BpOF4_01070 |
| Haliangium ochraceum DSM 14365 | 262196421 | Hoch_3235 |
| Variovorax paradoxus S110 | 239814019 | Vapar_1012 |
| Achromobacter xylosoxidans A8 | 311105813 | AXYL_02631 |
| Ruegeria sp. TM1040 | 99082616 | TM1040_2776 |
| Sulfurovum sp. NBC37-1 | 152992561 | SUN_0968 |
| Geobacter sulfurreducens PCA | 39997750 | GSU2656 |
| Chloroflexus aurantiacus J-10-fl | 163846906 | Caur_1333 |
| Pseudoalteromonas haloplanktis TAC125 | 77360571 | PSHAa1630 |
| Caulobacter crescentus NA1000 | 221234740 | CCNA_01803 |
| Thermoproteus uzoniensis 768-20 | 327310925 | TUZN_1029 |
| Pseudomonas fluorescens Pf0-1 | 77459687 | Pfl01_3465 |
| Lactobacillus casei ATCC 334 | 116494796 | LSEI_1307 |
| Prochlorococcus marinus str. AS9601 | 123967992 | A9601_04551 |
| Lactobacillus casei str. Zhang | 301066362 | LCAZH_1301 |
| Sphingobium japonicum UT26S | 294011287 | SJA_C1-13010 |
| Cyanothece sp. PCC 8801 | 218246082 | PCC8801_1231 |
| Rhodothermus marinus DSM 4252 | 268316954 | Rmar_1396 |
| Shewanella sp. W3-18-1 | 120598929 | Sputw3181_2121 |
| Nocardia farcinica IFM 10152 | 54022990 | nfa10230 |
| Bacillus subtilis subsp. subtilis str. 168 | 16078524 | BSU14600 |
| Nocardioides sp. JS614 | 119718672 | Noca_4453 |
| Waddlia chondrophila WSU 86-1044 | 297620707 | wcw_0466 |
| Trichodesmium erythraeum IMS101 | 113475499 | Tery_1831 |
| Bacillus tusciae DSM 2912 | 295694991 | Btus_0312 |
| Shewanella baltica OS223 | 217973404 | Sbal223_2233 |
| Frankia sp. CcI3 | 86741182 | Francci3_2486 |
| Bacillus licheniformis ATCC 14580 | 52080061 | BL01618 |
| Rubrobacter xylanophilus DSM 9941 | 108805280 | Rxyl_2478 |
| Conexibacter woesei DSM 14684 | 284045846 | Cwoe_4397 |
| Bacillus cereus B4264 | 218233546 | BCB4264_A4073 |
| Idiomarina loihiensis L2TR | 56460779 | IL1678 |
| Bacillus clausii KSM-K16 | 56964183 | ABC2418 |
| Lactococcus lactis subsp. cremoris MG1363 | 125622951 | llmg_0072 |

TABLE 4-continued bkdB genes

| Genome | Gene ID# | Locus Tag |
|---|---|---|
| Wolbachia endosymbiont of Drosophila melanogaster | 42520975 | WD1177 |
| Caulobacter sp. K31 | 167645836 | Caul_1872 |
| Bacillus megaterium QM B1551 | 294498115 | BMQ_1348 |
| Bacillus anthracis str. Sterne | 49186879 | BAS3881 |
| Lactobacillus reuteri SD2112 | 338204230 | HMPREF0538_21876 |
| Halobacterium salinarum R1 | 169236792 | OE4115F |
| Streptococcus thermophilus MN-ZLW-002 | 387909681 | Y1U_C0873 |
| Caulobacter crescentus CB15 | 16125973 | CC_1729 |
| Symbiobacterium thermophilum IAM 14863 | 51891551 | STH413 |
| Prochlorococcus marinus str. MIT 9313 | 33862493 | PMT0220 |
| Shewanella pealeana ATCC 700345 | 157962065 | Spea_2244 |
| Mycobacterium sp. JDM601 | 333990060 | JDM601_1420 |
| Bacillus cereus 03BB102 | 225865952 | BCA_4075 |
| Agrobacterium sp. H13-3 | 332716272 | AGROH133_11607 |
| Bacillus cereus ATCC 10987 | 42783066 | BCE_4019 |
| Nostoc punctiforme PCC 73102 | 186686433 | Npun_F6414 |
| Bacillus anthracis str. A0248 | 229601593 | BAA_4205 |
| Mycobacterium smegmatis str. MC2 155 NC_018289 | 399988989 | MSMEI_4593 |
| Shewanella amazonensis SB2B | 119774847 | Sama_1711 |
| Bacillus cellulosilyticus DSM 2522 | 317129370 | Bcell_2666 |
| Synechococcus sp. WH 8102 | 33865205 | SYNW0671 |
| Brucella abortus S19 | 189022865 | BAbS19_II06650 |
| Acetobacter pasteurianus IFO 3283-32 | 384063023 | APA32_12160 |
| Novosphingobium sp. PP1Y | 334142272 | PP1Y_AT28822 |
| Listeria monocytogenes HCC23 | 217964853 | LMHCC_1573 |
| Leuconostoc mesenteroides subsp. mesenteroides ATCC 8293 | 116617851 | LEUM_0739 |
| Bacillus subtilis subsp. spizizenii TU-B-10 | 350265764 | GYO_1799 |
| Halomicrobium mukohataei DSM 12286 | 257386742 | Hmuk_0676 |
| Thermobifida fusca YX | 72160586 | Tfu_0182 |
| Streptococcus gallolyticus subsp. gallolyticus ATCC BAA-2069 | 325978048 | SGGBAA2069_c08480 |
| Burkholderia mallei NCTC 10229 | 124383004 | BMA10229_1320 |
| Prochlorococcus marinus str. NATL1A | 124025169 | NATL1_04561 |
| Spirochaeta thermophila DSM 6192 | 307718514 | STHERM_c08240 |
| Streptococcus suis ST3 | 330833463 | SSUST3_1689 |
| Synechococcus sp. CC9311 | 161349989 | sync_0617 |
| Streptococcus suis SS12 | 386582791 | SSU12_1776 |
| Burkholderia thailandensis E264 | 83716049 | BTH_II2302 |
| Halomonas elongata DSM 2581 | 307544962 | HELO_2372 |
| Mycoplasma capricolum subsp. capricolum ATCC 27343 | 83319741 | MCAP_0227 |
| Pseudomonas aeruginosa LESB58 | 218891777 | PLES_30551 |
| Mycobacterium tuberculosis CDC1551 | 15842023 | MT2570 |
| Alkaliphilus metalliredigens QYMF | 150389069 | Amet_1253 |
| Sinorhizobium fredii NGR234 | 227823514 | NGR_c29910 |
| Alteromonas macleodii str. 'Deep ecotype' | 332141380 | MADE_1009910 |
| Geobacillus sp. C56-T3 | 297530773 | GC56T3_2513 |
| Leptospira borgpetersenii serovar Hardjo-bovis L550 | 116328021 | LBL_1316 |
| Brucella microti CCM 4915 | 256015305 | BMI_II520 |
| Meiothermus ruber DSM 1279 | 291296695 | Mrub_2322 |
| Sphingopyxis alaskensis RB2256 | 103486815 | Sala_1329 |
| Haloarcula marismortui ATCC 43049 | 55380239 | rrnB0198 |
| Listeria monocytogenes serotype 4b str. F2365 | 46907286 | LMOf2365_1075 |
| Thermosynechococcus elongatus BP-1 | 22298842 | tll1299 |
| Mycoplasma genitalium G37 | 12045128 | MG_272 |
| Shewanella sp. ANA-3 | 117920573 | Shewana3_2129 |
| Bacillus weihenstephanensis KBAB4 | 163941710 | BcerKBAB4_3797 |
| Shewanella putrefaciens CN-32 | 146292985 | Sputcn32_1887 |
| Lactococcus lactis subsp. cremoris SK11 | 116510883 | LACR_0049 |
| Burkholderia pseudomallei K96243 | 53723289 | BPSS2271 |
| Synechococcus sp. PCC 7002 | 170076743 | SYNPCC7002_A0110 |
| Arthrobacter aurescens TC1 | 119963490 | AAur_1523 |
| Weissella koreensis KACC 15510 | 339635177 | WKK_06345 |
| Burkholderia mallei ATCC 23344 | 53716063 | BMAA2011 |
| Macrococcus caseolyticus JCSC5402 | 222150962 | MCCL_0712 |
| Staphylococcus aureus subsp. aureus JH1 | 150393643 | SaurJH1_1177 |
| Burkholderia cenocepacia AU 1054 | 107022320 | Bcen_0764 |
| Meiothermus silvanus DSM 9946 | 297565574 | Mesil_1134 |
| Oceanobacillus iheyensis HTE831 | 23098869 | OB1414 |
| Lactobacillus plantarum WCFS1 | 380032903 | lp_2152 |
| Parabacteroides distasonis ATCC 8503 | 150007338 | BDI_0688 |
| Staphylococcus haemolyticus JCSC1435 | 70726858 | SH1857 |
| Lactobacillus fermentum IFO 3956 | 184155614 | LAF_1138 |
| Candidatus Amoebophilus asiaticus 5a2 | 189501498 | Aasi_0029 |
| Catenulispora acidiphila DSM 44928 | 256395300 | Caci_6169 |
| Bacillus amyloliquefaciens FZB42 | 154685877 | RBAM_014440 |
| Mycobacterium bovis BCG str. Pasteur 1173P2 | 121638377 | BCG_2515c |
| Staphylococcus aureus subsp. aureus MW2 | 212827071 | MW0978 |
| Frankia sp. EAN1pec | 158313432 | Franean1_1595 |
| Streptococcus equi subsp. equi 4047 | 225870728 | SEQ_1404 |
| Gloeobacter violaceus PCC 7421 | 37522138 | gll2569 |
| Pseudomonas aeruginosa UCBPP-PA14 | 116050196 | PA14_35500 |
| Prochlorococcus marinus str. MIT 9215 | 157412817 | P9215_04811 |
| Thermoplasma volcanium GSS1 | 13540931 | TVN0100 |
| Bacillus megaterium DSM 319 | 295703464 | BMD_1328 |
| Anabaena variabilis ATCC 29413 | 75909383 | Ava_3176 |
| Paenlbacillus polymyxa E681 | 308069293 | PPE_02530 |

TABLE 4-continued bkdB genes

| Genome | Gene ID# | Locus Tag |
|---|---|---|
| *Chlamydophila abortus* S26/3 | 62185091 | CAB462 |
| *Geobacter uraniireducens* Rf4 | 148264937 | Gura_2898 |
| *Lactobacillus casei* BL23 | 191638311 | LCABL_15380 |
| *Streptococcus agalactiae* A909 | 76787510 | SAK_003 |
| *Pseudomonas entomophila* L48 | 104782859 | PSEEN3855 |
| *Halorubrum lacusprofundi* ATCC 49239 | 222478580 | Hlac_0141 |
| *Geobacillus kaustophilus* HTA426 | 56419595 | GK1060 |
| *Staphylococcus aureus* subsp. *aureus* USA300_FPR3757 | 87161817 | SAUSA300_0995 |
| *Azospirillum* sp. B510 | 288958360 | AZL_015190 |
| *Chlamydophila psittaci* 08DC60 | 384452547 | CPS0D_0522 |
| *Lactobacillus rhamnosus* GG NC_013198 | 258508317 | LGG_01322 |
| *Staphylococcus aureus* RF122 | 82750705 | SAB0961 |
| cyanobacterium UCYN-A | 284928764 | UCYN_01790 |
| *Zymomonas mobilis* subsp. *pomaceae* ATCC 29192 | 338707699 | Zymop_0708 |
| *Burkholderia cenocepacia* MC0-3 | 170732568 | Bcenmc03_1218 |
| *Thermus scotoductus* SA-01 | 320449329 | TSC_c02360 |
| Candidatus *Protochlamydia amoebophila* UWE25 | 46447365 | pc1731 |
| *Bacillus cereus* biovar *anthracis* str. CI | 301055461 | BACI_c39270 |
| *Burkholderia cenocepacia* HI2424 | 116689267 | Bcen2424_1245 |
| *Oenococcus oeni* PSU-1 | 116490426 | OEOE_0330 |
| *Listeria monocytogenes* 08-5578 | 284801386 | LM5578_1137 |
| *Alteromonas* sp. SN2 | 333893050 | ambt_07975 |
| *Shewanella* sp. MR-4 | 113970363 | Shewmr4_2026 |
| *Streptomyces avermitilis* MA-4680 | 29830907 | SAV_4364 |
| *Mycoplasma hyorhinis* HUB-1 | 304373301 | MHR_0515 |
| uncultured methanogenic archaeon RC-I | 147919054 | RRC124 |
| *Staphylococcus aureus* subsp. *aureus* N315 | 15926680 | SA0945 |
| *Prochlorococcus marinus* subsp. *pastoris* str. CCMP1986 | 33860962 | PMM0405 |
| *Bacteroides fragilis* YCH46 | 53712911 | BF1621 |
| *Thermobispora bispora* DSM 43833 | 296271281 | Tbis_3330 |
| *Amycolatopsis mediterranei* U32 | 300789393 | AMED_7569 |
| *Paenibacillus* sp. Y412MC10 | 261406247 | GYMC10_2403 |
| *Erysipelothrix rhusiopathiae* str. Fujisawa | 336065680 | ERH_0440 |
| *Sulfurimonas autotrophica* DSM 16294 | 307720480 | Saut_0559 |
| *Acaryochloris marina* MBIC11017 | 158336703 | AM1_3571 |
| *Lactobacillus plantarum* JDM1 | 254556970 | JDM1_1803 |
| *Streptococcus equi* subsp. *zooepidemicus* MGCS10565 | 195978329 | Sez_1220 |
| *Bacillus thuringiensis* BMB171 | 296504464 | BMB171_C3634 |
| *Mycobacterium avium* subsp. *paratuberculosis* K-10 | 41408405 | MAP2307c |
| *Mycoplasma fermentans* JER | 308190216 | MFE_06880 |
| *Leptospira interrogans* serovar Lai str. 56601 | 24214708 | LA_2008 |
| *Brucella melitensis* biovar Abortus 2308 | 83269596 | BAB2_0713 |
| *Rhodococcus jostii* RHA1 | 111020308 | RHA1_ro03319 |
| *Ramlibacter tataouinensis* TTB310 | 337278683 | Rta_10500 |
| *Mycoplasma fermentans* M64 | 319777549 | MfeM64YM_0828 |
| *Ochrobactrum anthropi* ATCC 49188 | 153010874 | Oant_3553 |
| *Erythrobacter litoralis* HTCC2594 | 85373860 | ELI_05165 |
| *Bacillus subtilis* BSn5 | 321315219 | BSn5_19375 |
| *Pseudomonas putida* GB-1 | 167034959 | PputGB1_3964 |
| *Prochlorococcus marinus* str. MIT 9515 | 123965701 | P9515_04661 |
| *Bacillus cereus* Q1 | 222097419 | BCQ_3759 |
| *Cyanothece* sp. PCC 7822 | 307154646 | Cyan7822_4864 |
| *Anoxybacillus flavithermus* WK1 | 212639718 | Aflv_1892 |
| *Bacillus cereus* AH187 | 217961456 | BCAH187_A4089 |
| *Burkholderia ambifaria* AMMD | 115351178 | Bamb_1125 |
| *Streptococcus uberis* 0140J | 222153239 | SUB1101 |
| *Sinorhizobium medicae* WSM419 | 150398026 | Smed_2828 |
| *Halogeometricum borinquense* DSM 11551 | 313125080 | Hbor_02950 |
| *Mycobacterium vanbaalenii* PYR-1 | 120405038 | Mvan_4084 |
| *Halalkalicoccus jeotgali* B3 | 300709397 | HacjB3_00130 |
| *Lysinibacillus sphaericus* C3-41 | 169826945 | Bsph_1365 |
| *Exiguobacterium sibiricum* 255-15 | 172058018 | Exlg_2009 |
| *Mycoplasma mobile* 163K | 47459416 | MMOB5810 |
| *Streptococcus suis* P1/7 | 253754330 | SSU1635 |
| *Geobacillus* sp. Y4.1MC1 | 312111829 | GY4MC1_2839 |
| *Anaeromyxobacter* sp. Fw109-5 | 153004857 | Anae109_1995 |
| *Simkania negevensis* Z | 338732264 | SNE_A03690 |
| *Micromonospora* sp. L5 | 315504011 | ML5_3231 |
| *Listeria monocytogenes* EGD-e | 16803094 | lmo1054 |
| *Cyanothece* sp. PCC 8802 | 257059131 | Cyan8802_1261 |
| *Prochlorococcus marinus* str. MIT 9211 | 159902944 | P9211_04031 |
| *Carnobacterium* sp. 17-4 | 328957243 | CAR_c09200 |
| *Zymomonas mobilis* subsp. *mobilis* NCIMB 11163 | 260752983 | Za10_0745 |
| *Leptospira borgpetersenii* serovar Hardjo-bovis JB197 | 116331526 | LBJ_1968 |
| *Saccharopolyspora erythraea* NRRL 2338 | 134101994 | SACE_5544 |
| *Pusillimonas* sp. T7-7 | 332284091 | PT7_0838 |
| *Pediococcus pentosaceus* ATCC 25745 | 116493499 | PEPE_1771 |
| *Shewanella piezotolerans* WP3 | 212635403 | swp_2604 |
| *Streptosporangium roseum* DSM 43021 | 271970150 | Sros_8972 |
| *Lactobacillus reuteri* JCM 1112 | 184153265 | LAR_0610 |
| *Paenibacillus polymyxa* SC2 | 310642335 | PPSC2_c2887 |
| 'Nostoc azollae' 0708 | 298490612 | Aazo_1439 |
| *Rhodoferax ferrireducens* T118 | 89902316 | Rfer_3552 |
| *Streptomyces griseus* subsp. *griseus* NBRC 13350 | 182437543 | SGR_3750 |
| *Pyrobaculum aerophilum* str. IM2 | 18313491 | PAE2648 |
| *Mycobacterium smegmatis* str. MC2 155 NC_008596 | 118470681 | MSMEG_4710 |
| *Mycobacterium abscessus* ATCC 19977 | 169627974 | MAB_0895c |
| *Thermoanaerobacter tengcongensis* MB4 | 20806714 | TTE0188 |

TABLE 4-continued bkdB genes

| Genome | Gene ID# | Locus Tag |
|---|---|---|
| *Cyanothece* sp. PCC 7425 | 220910325 | Cyan7425_4977 |
| *Brevibacillus brevis* NBRC 100599 | 226312883 | BBR47_32960 |
| *Salinispora arenicola* CNS-205 | 159037838 | Sare_2240 |
| *Listeria monocytogenes* 08-5923 | 284994528 | LM5923_1091 |
| *Sphaerobacter thermophilus* DSM 20745 | 269929375 | Sthe_3475 |
| *Mycobacterium tuberculosis* F11 | 148823692 | TBFG_12517 |
| *Mycoplasma hyopneumoniae* 232 | 54020221 | mhp503 |
| *Marinithermus hydrothermalis* DSM 14884 | 328950233 | Marky_0708 |
| *Mycoplasma mycoides* subsp. *capri* LC str. 95010 | 331703290 | MLC_2700 |
| *Listeria welshimeri* serovar 6b str. SLCC5334 | 116872448 | lwe1030 |
| *Glaciecola* sp. 4H-3-7 + YE-5 | 332306592 | Glaag_2230 |
| *Geobacter metallireducens* GS-15 | 404497364 | Gmet_2511 |
| *Nostoc* sp. PCC 7120 | 17231098 | alr3606 |
| *Mycoplasma hyopneumoniae* J | 71893854 | MHJ_0503 |
| *Propionibacterium acnes* KPA171202 | 50843531 | PPA2092 |
| *Picrophilus torridus* DSM 9790 | 48477619 | PTO0547 |
| *Staphylococcus aureus* subsp. *aureus* str. Newman | 151221173 | NWMN_0961 |
| *Geobacillus* sp. Y412MC52 | 319766073 | GYMC52_0960 |
| *Ferrimonas balearica* DSM 9799 | 308050066 | Fbal_2356 |
| *Listeria monocytogenes* serotype 4b str. CLIP 80459 | 226223672 | Lm4b_01074 |
| *Sinorhizobium meliloti* AK83 | 334317692 | Sinme_2990 |
| *Prochlorococcus marinus* str. NATL2A | 72383575 | PMN2A_1739 |
| *Sphingobacterium* sp. 21 | 326799941 | Sph21_2539 |
| *Pseudomonas putida* W619 | 170722907 | PputW619_3744 |

TABLE 5

IpdV Genes

| Genome | Gene ID# | Locus Tag |
|---|---|---|
| *Arcobacter* sp. L | 384172498 | ABLL_1683 |
| *Listeria monocytogenes* SLCC2479 | 405758055 | LMOSLCC2479_1068 |
| *Bacillus coagulans* 36D1 | 3477506611 | Bcoa_0220 |
| *Lactococcus lactis* subsp. *cremoris* NZ9000 | 389853268 | LLNZ_00350 |
| *Staphylococcus aureus* subsp. *aureus* T0131 | 384869629 | SAT0131_01134 |
| *Mycoplasma bovis* HB0801 | 392429697 | Mbov_0106 |
| *Sulfobacillus acidophilus* TPY | 339629488 | TPY_3236 |
| *Listeria ivanovii* subsp. *ivanovii* PAM 55 | 347548456 | LIV_1000 |
| *Listeria monocytogenes* M7 | 386026372 | LMM7_1085 |
| *Bacillus subtilis* subsp. *subtilis* str. RO-NN-1 | 384175197 | I33_1641 |
| *Listeria monocytogenes* SLCC7179 | 404413142 | LMOSLCC7179_1036 |
| *Sinorhizobium fredii* HH103 | 378827586 | SFHH103_03001 |
| *Sulfobacillus acidophilus* DSM 10332 | 379007394 | Sulac_1677 |
| *Staphylococcus aureus* subsp. *aureus* M013 | 379020803 | M013TW_1028 |
| *Haloferax mediterranei* ATCC 33500 | 389848367 | HFX_2955 |

TABLE 5-continued

IpdV Genes

| Genome | Gene ID# | Locus Tag |
|---|---|---|
| *Enterococcus hirae* ATCC 9790 | 392989733 | EHR_12850 |
| *Pseudomonas fluorescens* F113 | 378950261 | PSF113_2343 |
| *Staphylococcus aureus* subsp. *aureus* 11819-97 | 385781324 | MS7_1053 |
| *Staphylococcus aureus* subsp. *aureus* LGA251 | 387780209 | SARLGA251_10090 |
| *Staphylococcus aureus* subsp. *aureus* VC40 | 379014289 | SAVC_04640 |
| *Haloquadratum walsbyi* C23 | 385802475 | Hqrw_1115 |
| *Staphylococcus aureus* subsp. *aureus* ED133 | 384547282 | SAOV_1040 |
| *Mycoplasma bovis* Hubei-1 | 339320627 | MMB_0100 |
| *Methanocella conradii* HZ254 | 383320310 | Mtc_1893 |
| *Sinorhizobium meliloti* SM11 | 384537527 | SM11_chr3107 |
| *Desulfosporosinus acidiphilus* SJ4 | 392426986 | Desaci_3767 |
| *Pyrobaculum* sp. 1860 | 374327310 | P186_1854 |
| *Paenibacillus polymyxa* M1 | 386041285 | PPM_2595 |
| *Bacillus amyloliquefaciens* LL3 | 384163957 | LL3_01567 |
| *Listeria monocytogenes* J0161 | 386046717 | LMOG_00665 |
| *Bacillus megaterium* WSH-002 | 384048054 | BMWSH_3881 |
| *Lactobacillus casei* BD-II | 385823212 | LCBD_1516 |
| *Listeria monocytogenes* SLCC5850 | 404410300 | LMOSLCC5850_1061 |
| *Melissococcus plutonius* DAT56 | 379727535 | MPD5_0995 |
| *Pyrobaculum oguniense* TE7 | 379004031 | Pogu_1069 |
| *Amycolatopsis mediterranei* S699 NC_017186 | 384147341 | RAM_11050 |
| *Bacillus cereus* NC7401 | 375285964 | BCN_3870 |
| *Listeria monocytogenes* SLCC2540 | 405755134 | LMOSLCC2540_1055 |
| *Staphylococcus aureus* subsp. *aureus* 71193 | 386728776 | ST398NM01_1093 |
| *Brucella suis* VBI22 | 376278495 | BSVBI22_B0521 |
| *Listeria monocytogenes* L99 | 386007779 | lmo4a_1064 |
| *Exiguobacterium antarcticum* B7 | 407477696 | Eab7_1857 |
| *Sulfolobus solfataricus* 98/2 | 384433026 | Ssol_0504 |
| *Listeria monocytogenes* SLCC2376 | 404407511 | LMOSLCC2376_1028 |
| *Ignavibacterium album* JCM 16511 | 385811557 | IALB_2982 |
| *Mycobacterium tuberculosis* RGTB423 | 386006142 | MRGA423_20730 |
| *Staphylococcus lugdunensis* N920143 | 385784711 | SLUG_17740 |
| *Bacillus amyloliquefaciens* subsp. *plantarum* YAU B9601-Y2 | 384265012 | BANAU_1382 |
| *Corynebacterium variabile* DSM 44702 | 340793902 | CVAR_0939 |
| *Anaerobaculum mobile* DSM 13181 | 392407596 | Anamo_1266 |
| *Haloarcula hispanica* ATCC 33960 | 344210514 | HAH_0213 |
| *Lactobacillus rhamnosus* GG NC_017482 | 385827989 | LRHM_1269 |
| *Geobacillus thermoleovorans* CCB_US3_UF5 | 375008019 | GTCCBUS3UF5_12380 |
| *Brucella melitensis* M5-90 | 384213037 | BM590_B0499 |
| *Staphylococcus pseudintermedius* ED99 | 386319626 | SPSE_1695 |
| *Lactobacillus casei* LC2W | 385820011 | LC2W_1481 |
| *Bacillus amyloliquefaciens* subsp. *plantarum* CAU B946 | 375362109 | BACAU_1419 |
| *Staphylococcus aureus* subsp. *aureus* ECT-R 2 | 384864323 | ECTR2_951 |
| *Listeria monocytogenes* serotype 7 str. SLCC2482 | 404286469 | LMOSLCC2482_1102 |
| *Staphylococcus aureus* subsp. *aureus* TCH60 | 384868022 | HMPREF0772_12136 |
| *Lactobacillus rhamnosus* ATCC 8530 | 385835177 | LRHK_1313 |
| *Pseudomonas aeruginosa* NCGM2.S1 | 386066188 | NCGM2_3259 |

TABLE 5-continued lpdV Genes

| Genome | Gene ID# | Locus Tag |
|---|---|---|
| *Bacillus anthracis* str. H9401 | 386737859 | H9401_3986 |
| *Bacillus amyloliquefaciens* TA208 | 384159555 | BAMTA208_09840 |
| *Pseudomonas fluorescens* A506 | 387894502 | PflA506_3340 |
| *Sinorhizobium meliloti* BL225C | 384530817 | SinmeB_2765 |
| *Bacillus* sp. JS | 386758177 | MY9_1600 |
| *Listeria monocytogenes* SLCC2378 | 405752277 | LMOSLCC2378_1073 |
| *Listeria monocytogenes* Finland 1998 | 386053326 | LMLG_2332 |
| *Arcobacter butzleri* ED-1 | 384156087 | ABED_1375 |
| *Brucella melitensis* NI | 384446663 | BMNI_II0492 |
| *Brachyspira pilosicoli* B2904 | 404476148 | B2904_orf1496 |
| *Alicyclobacillus acidocaldarius* subsp. *acidocaldarius* Tc-4-1 | 384134350 | TC41_0585 |
| *Thermoanaerobacter wiegelii* Rt8.B1 | 345016728 | Thewi_0296 |
| *Lactobacillus buchneri* CD034 | 406026603 | LBUCD034_0784 |
| *Brucella canis* HSK A52141 | 376276772 | BCA52141_II0438 |
| *Bacillus amyloliquefaciens* XH7 | 384168609 | BAXH7_02007 |
| *Pseudomonas aeruginosa* M18 | 386058853 | PAM18_2790 |
| *Enterococcus faecium* Aus0004 | 383328410 | EFAU004_01091 |
| halophilic archaeon DL31 | 345006004 | Halar_2852 |
| *Tetragenococcus halophilus* NBRC 12172 | 352517700 | TEH_15260 |
| *Staphylococcus aureus* 04-02981 | 387150238 | SA2981_1053 |
| *Thermoanaerobacterium saccharolyticum* JW/SL-YS485 | 390935443 | Tsac_2347 |
| *Staphylococcus aureus* subsp. *aureus* HO 5096 0412 | 386830632 | SAEMRSA15_09260 |
| *Paenibacillus mucilaginosus* 3016 | 379723634 | PM3016_5959 |
| *Pseudomonas putida* S16 | 339488701 | PPS_3808 |
| *Lactobacillus salivarius* CECT 5713 | 385839944 | HN6_00133 |
| *Marinobacter adhaerens* HP15 | 385329806 | HP15_65 |
| *Burkholderia cepacia* GG4 | 402566976 | GEM_2214 |
| *Brucella melitensis* M28 | 384410138 | BM28_B0500 |
| *Listeria monocytogenes* 10403S | 386043381 | LMRG_00517 |
| *Sphingobium* sp. SYK-6 | 347527353 | SLG_09680 |
| *Enterococcus faecium* DO | 389868411 | HMPREF0351_11228 |
| *Bacillus thuringiensis* serovar *finitimus* YBT-020 | 384181786 | YBT020_19510 |
| *Bacillus cereus* F837/76 | 376267866 | bcf_19720 |
| *Thermoproteus tenax* Kra 1 | 352681565 | TTX_0334 |
| *Brachyspira intermedia* PWS/A | 384208204 | Bint_0715 |
| *Paenibacillus mucilaginosus* K02 | 386726383 | B2K_30290 |
| *Enterococcus faecalis* 62 | 384518457 | EF62_1807 |
| *Listeria monocytogenes* ATCC 19117 | 405749412 | LMOATCC19117_1077 |
| *Listeria monocytogenes* FSL R2-561 | 386049983 | LMKG_01867 |
| *Natrinema* sp. J7-2 | 397771794 | NJ7G_0008 |
| *Pseudomonas putida* DOT-T1E | 397697837 | T1E-5102 |
| *Burkholderia pseudomallei* 1026b | 386866104 | BP1026B_II2445 |
| *Staphylococcus aureus* subsp. *aureus* str. JKD6008 | 384861691 | SAA6008_01051 |
| *Listeria monocytogenes* 07PF0776 | 386731810 | MUO_05550 |
| *Solibacillus silvestris* StLB046 | 393201878 | SSIL_3151 |
| *Paenibacillus terrae* HPL-003 | 374323890 | HPL003_20290 |
| *Staphylococcus aureus* subsp. *aureus* S0385 | 387602369 | SAPIG1093 |
| *Staphylococcus aureus* subsp. *aureus* TW20 | 387142708 | SATW20_10910 |
| *Brucella pinnipedialis* B2/94 | 340792255 | BPI_II508 |
| | 384223057 | BS1330_II0522 |
| *Streptococcus parasanguinis* FW213 | 387879561 | Spaf_1060 |
| *Sinorhizobium fredii* USDA 257 | 398355224 | USDA257_c54080 |
| *Enterococcus faecalis* D32 | 397699745 | EFD32_1168 |
| *Bacillus amyloliquefaciens* Y2 | 387897997 | MUS_1556 |
| *Bacillus anthracis* str. CDC 684 | 227816743 | BAMEG_4222 |
| *Lactobacillus sakei* subsp. *sakei* 23K | 81428692 | LSA1082 |
| *Bacillus halodurans* C-125 | 15615215 | BH2652 |
| *Paenibacillus* sp. JDR-2 | 251796662 | Pjdr2_2653 |
| *Listeria seeligeri* serovar 1/2b str. SLCC3954 | 289434316 | lse_0949 |
| *Pseudomonas fluorescens* SBW25 | 229591399 | PFLU3967 |
| *Halopiger xanaduensis* SH-6 | 336252524 | Halxa_1118 |
| *Pseudomonas fluorescens* Pf-5 | 70729899 | PFL_2531 |
| *Bacillus subtilis* subsp. *spizizenii* str. W23 | 305674188 | BSUW23_07515 |
| *Bradyrhizobium japonicum* USDA 110 | 27381445 | blr6334 |
| *Lactobacillus salivarius* UCC118 | 90961138 | LSL_0156 |
| *Paenibacillus mucilaginosus* KNP414 | 337750575 | KNP414_06346 |
| *Haloferax volcanii* DS2 | 292657069 | HVO_2961 |
| *Brucella melitensis* ATCC 23457 | 225686319 | BMEA_B0500 |
| *Lactobacillus reuteri* DSM 20016 | 148543866 | Lreu_0634 |
| *Bacillus pumilus* SAFR-032 | 157692139 | BPUM_1358 |
| *Bacillus cereus* G9842 | 218899125 | BCG9842_B1168 |
| *Arthrobacter arilaitensis* Re117 | 308177811 | AARI_20270 |
| *Pseudomonas putida* KT2440 | 26991093 | PP_4404 |
| *Haloterrigena turkmenica* DSM 5511 | 284166850 | Htur_3594 |
| *Rothia dentocariosa* ATCC 17931 | 311111675 | HMPREF0733_10005 |
| *Enterococcus faecalis* V583 | 29375923 | EF1356 |
| *Staphylococcus epidermidis* RP62A | 57866609 | SERP0683 |
| *Staphylococcus aureus* subsp. *aureus* JH9 | 148267589 | SaurJH9_1156 |
| *Staphylococcus aureus* subsp. *aureus* COL | 57651705 | SACOL1105 |
| *Staphylococcus epidermidis* ATCC 12228 | 27467712 | SE0794 |
| *Buchnera aphidicola* (*Cinara tujafilina*) | 336233239 | BCTU_137 |
| *Brucella suis* 1330 | 23500274 | BRA0527 |
| *Bacillus cereus* AH820 | 218905100 | BCAH820_3984 |
| *Thermaerobacter marianensis* DSM 12885 | 317122503 | Tmar_1670 |
| *Desulfovibrio magneticus* RS-1 | 239908133 | DMR_34970 |
| *Burkholderia pseudomallei* 1106a | 126455671 | BURPS1106A_A3064 |
| *Geobacillus* sp. Y412MC61 | 261419259 | GYMC61_1835 |
| *Mesorhizobium ciceri* biovar *biserrulae* WSM1271 | 319780623 | Mesci_0884 |
| *Calditerrivibrio nitroreducens* DSM 19672 | 313672838 | Calni_0875 |
| *Wigglesworthia glossinidia* endosymbiont of *Glossina brevipalpis* | 32491070 | WGLp321 |
| *Exiguobacterium* sp. AT1b | 229918501 | EAT1b_2788 |
| *Flexistipes sinusarabici* DSM 4947 | 336323720 | Flexsi_1469 |
| *Lactobacillus plantarum* subsp. *plantarum* ST-III | 308180957 | LPST_C1775 |
| *Bacillus anthracis* str. Ames | 30264041 | BA_4181 |
| *Halobacterium* sp. NRC-1 | 15791043 | VNG2220G |
| *Bacillus cereus* E33L | 52141520 | BCZK3728 |
| *Geobacillus thermodenitrificans* NG80-2 | 138894595 | GTNG_0925 |
| *Burkholderia glumae* BGR1 | 238023735 | bglu_2g02670 |
| *Alicycliphilus denitrificans* BC | 319761350 | Alide_0631 |
| *Staphylococcus aureus* subsp. *aureus* USA300_TCH1516 | 161509279 | USA300HOU_1039 |
| *Bacillus thuringiensis* str. Al Hakam | 118479181 | BALH_3592 |
| *Bacillus thuringiensis* serovar *chinensis* CT-43 | 384188033 | CT43_CH3975 |

TABLE 5-continued

IpdV Genes

| Genome | Gene ID# | Locus Tag |
|---|---|---|
| *Brucella abortus* A13334 | 376271254 | BAA13334_II01340 |
| *Bacillus thuringiensis* serovar konkukian str. 97-27 | 49478876 | BT9727_3712 |
| *Alicycliphilus denitrificans* K601 | 330823225 | Alide2_0596 |
| *Baumannia cicadellinicola* str. Hc (*Homalodisca coagulata*) | 94676976 | BCI_0510 |
| *Geobacillus thermoglucosidasius* C56-YS93 | 336236212 | Geoth_2860 |
| *Alicyclobacillus acidocaldarius* subsp. *acidocaldarius* DSM 446 | 258510468 | Aaci_0454 |
| *Rothia mucilaginosa* DY-18 | 283457790 | RMDY18_07290 |
| *Burkholderia pseudomallei* 668 | 126442365 | BURPS668_A3190 |
| *Jonesia denitrificans* DSM 20603 | 256832700 | Jden_1475 |
| *Burkholderia gladioli* BSR3 | 330819433 | bgla_2g03070 |
| *Staphylococcus aureus* subsp. *aureus* MSSA476 | 49485934 | SAS1031 |
| *Sphingomonas wittichii* RW1 | 148553702 | Swit_0779 |
| *Staphylococcus lugdunensis* HKU09-01 | 289551092 | SLGD_01779 |
| *Staphylococcus saprophyticus* subsp. *saprophyticus* ATCC 15305 | 73663002 | SSP1693 |
| *Natrialba magadii* ATCC 43099 | 289581337 | Nmag_1665 |
| *Brucella suis* ATCC 23445 | 163844685 | BSUIS_B0522 |
| *Listeria innocua* Clip11262 | 16800116 | lin1047 |
| *Bacillus cereus* ATCC 14579 | 30022058 | BC3970 |
| *Pseudomonas putida* F1 | 148546690 | Pput_1450 |
| *Brucella abortus* bv. 1 str. 9-941 | 62317612 | BruAb2_0697 |
| *Burkholderia mallei* SAVP1 | 121597939 | BMASAVP1_1033 |
| *Pseudomonas aeruginosa* DK2 | 392984201 | PADK2_14025 |
| *Brevundimonas subvibrioides* ATCC 15264 | 302384433 | Bresu_3327 |
| *Sphingobium chlorophenolicum* L-1 | 334342794 | Sphch_3288 |
| *Thermoanaerobacter* sp. X513 | 307724064 | Thet_0899 |
| *Staphylococcus carnosus* subsp. *carnosus* TM300 | 224476211 | Sca_0722 |
| *Lactobacillus fermentum* CECT 5716 | 385812452 | LC40_0740 |
| *Geobacillus* sp. WCH70 | 239826460 | GWCH70_0955 |
| *Bacillus coagulans* 2-6 | 336113643 | BCO26_0965 |
| *Kocuria rhizophila* DC2201 | 184201087 | KRH_11410 |
| *Pseudomonas putida* ND6 | 395447957 | YSA_07988 |
| *Methanocella paludicola* SANAE | 282164390 | MCP_1720 |
| *Leuconostoc gasicomitatum* LMG 18811 | 300173679 | LEGAS_1378 |
| *Burkholderia ambifaria* MC40-6 | 172060192 | BamMC406_1137 |
| *Burkholderia pseudomallei* 1710b | 76818035 | BURPS1710b_A1408 |
| *Mycoplasma agalactiae* | 291320035 | MAGa1040 |
| | 404488951 | BLi01677 |
| *Staphylococcus aureus* subsp. *aureus* MSHR1132 | 379795467 | SAMSHR1132_09430 |
| *Natronomonas pharaonis* DSM 2160 | 76800707 | NP0104A |
| *Staphylococcus aureus* subsp. *aureus* ED98 | 269202707 | SAAV_1061 |
| *Hirschia baltica* ATCC 49814 | 254293979 | Hbal_6117 |
| *Thermoplasma acidophilum* DSM 1728 | 16082404 | Ta1435 |
| *Bacillus selenitireducens* MLS10 | 297583901 | Bsel_1605 |
| *Mesorhizobium opportunistum* WSM2075 | 337265443 | Mesop_0914 |
| *Sinorhizobium meliloti* 1021 | 15966688 | SMc03204 |
| *Burkholderia mallei* NCTC 10247 | 126447169 | BMA10247_A2299 |
| *Halobacillus halophilus* DSM 2266 | 386714110 | HBHAL_2811 |
| *Staphylococcus pseudintermedius* HKU10-03 | 319892094 | SPSINT_0805 |
| *Bordetella petrii* DSM 12804 | 163857821 | Bpet3508 |
| *Listeria monocytogenes* L312 | 406703831 | LMOL312_1056 |
| *Brucella canis* ATCC 23365 | 161620589 | BCAN_B0525 |
| *Brucella ovis* ATCC 25840 | 148558309 | BOV_A0459 |
| *Bacillus anthracis* str. 'Ames Ancestor' | 47529477 | GBAA_4181 |
| *Mesorhizobium loti* MAFF303099 | 13473766 | mll4470 |
| *Pseudomonas putida* BIRD-1 | 386011039 | PPUBIRD1_1438 |
| *Pyrobaculum calidifontis* JCM 11548 | 126460010 | Pcal_1402 |
| *Candidatus Blochmannia pennsylvanicus* str. BPEN | 71891939 | BPEN_156 |
| *Staphylococcus aureus* subsp. *aureus* MRSA252 | 49483259 | SAR1070 |
| *Mycoplasma agalactiae* PG2 | 148377364 | MAG_0960 |
| *Pseudomonas aeruginosa* PA7 | 152989284 | PSPA7_2991 |
| *Lactobacillus buchneri* NRRL B-30929 | 331701107 | Lbuc_0739 |
| *Aerococcus urinae* ACS-120-V-Col10a | 326803933 | HMPREF9243_1600 |
| *Bacillus atrophaeus* 1942 | 311067977 | BATR1942_05075 |
| *Thermoanaerobacter* sp. X514 | 167040661 | Teth514_2038 |
| *Staphylococcus aureus* subsp. *aureus* Mu3 | 156979419 | SAHV_1088 |
| *Staphylococcus aureus* subsp. *aureus* JKD6159 | 384549857 | SAA6159_00952 |
| *Bacillus amyloliquefaciens* DSM 7 | 308173427 | BAMF_1536 |
| *Maricaulis maris* MCS10 | 114569260 | Mmar10_0709 |
| *Thermoanaerobacter brockii* subsp. *finnii* Ako-1 | 320115619 | Thebr_0807 |
| *Burkholderia cenocepacia* J2315 | 206559592 | BCAL1215 |
| *Pseudomonas brassicacearum* subsp. *brassicacearum* NFM421 | 330810245 | PSEBR_a3381 |
| *Staphylococcus aureus* subsp. *aureus* Mu50 | 15924086 | SAV1096 |
| *Lactobacillus rhamnosus* Lc 705 | 258539528 | LC705_01337 |
| *Spirochaeta coccoides* DSM 17374 | 330837591 | Spico_1652 |
| *Brucella melitensis* bv. 1 str. 16M | 17989090 | BMEII0745 |
| *Staphylococcus aureus* subsp. *aureus* NCTC 8325 | 88194795 | SAOUHSC_01043 |
| *Leuconostoc citreum* KM20 | 170016785 | LCK_00427 |
| *Burkholderia* sp. 383 | 78065834 | Bcep18194_A4363 |
| *Prevotella melaninogenica* ATCC 25845 | 302346454 | HMPREF0659_A6708 |
| *Bacillus pseudofirmus* OF4 | 288553238 | BpOF4_01065 |
| *Achromobacter xylosoxidans* A8 | 311105814 | AXYL_02632 |
| *Ruegeria* sp. TM1040 | 99082615 | TM1040_2775 |
| *Metallosphaera sedula* DSM 5348 | 146304009 | Msed_1241 |
| *Borrelia garinii* PBi | 51598980 | BG0750 |
| *Thermoproteus uzoniensis* 768-20 | 327310926 | TUZN_1030 |
| *Pseudomonas fluorescens* Pf0-1 | 77459688 | Pfl01_3466 |
| *Lactobacillus casei* ATCC 334 | 116494797 | LSEI_1308 |
| *Lactobacillus casei* str. Zhang | 301066363 | LCAZH_1302 |
| *Bacillus subtilis* subsp. *subtilis* str. 168 | 16078525 | BSU14610 |
| *Bacillus tusciae* DSM 2912 | 295694992 | Btus_0313 |
| *Bacillus licheniformis* ATCC 14580 | 52080062 | BL01619 |
| *Borrelia turicatae* 91E135 | 119953505 | BT0728 |
| *Slackia heliotrinireducens* DSM 20476 | 257064081 | Shel_13830 |
| *Acidilobus saccharovorans* 345-15 | 302348861 | ASAC_1063 |
| *Conexibacter woesei* DSM 14684 | 284045845 | Cwoe_4396 |
| *Bacillus cereus* B4264 | 218233948 | BCB4264_A4072 |
| *Prevotella denticola* F0289 | 327314405 | HMPREF9137_2189 |
| *Bacillus clausii* KSM-K16 | 56964182 | ABC2417 |
| *Lactococcus lactis* subsp. *cremoris* MG1363 | 125622950 | llmg_0071 |
| *Dictyoglomus turgidum* DSM 6724 | 217966916 | Dtur_0515 |

TABLE 5-continued

IpdV Genes

| Genome | Gene ID# | Locus Tag |
|---|---|---|
| *Methanococcus voltae* A3 | 297619150 | Mvol_0623 |
| *Caulobacter* sp. K31 | 167645837 | Caul_1873 |
| *Enterococcus faecalis* OG1RF | 384513108 | OG1RF_11144 |
| *Bacillus megaterium* QM B1551 | 294498116 | BMQ_1349 |
| *Bacillus anthracis* str. Sterne | 49186878 | BAS3880 |
| *Bacillus cytotoxicus* NVH 391-98 | 152976383 | Bcer98_2671 |
| *Lactobacillus reuteri* SD2112 | 338204231 | HMPREF0538_21877 |
| *Halobacterium salinarum* R1 | 169236793 | OE4116F |
| *Symbiobacterium thermophilum* IAM 14863 | 51891552 | STH414 |
| *Chlorobium phaeobacteroides* BS1 | 189499997 | Cphamn1_1045 |
| *Bacillus cereus* 03BB102 | 225865951 | BCA_4074 |
| *Bacillus cereus* ATCC 10987 | 42783065 | BCE_4018 |
| *Vulcanisaeta moutnovskia* 768-28 | 325968467 | VMUT_0947 |
| *Bacillus anthracis* str. A0248 | 229602624 | BAA_4204 |
| *Bacillus cellulosilyticus* DSM 2522 | 317129369 | Bcell_2665 |
| *Brucella abortus* S19 | 189022864 | BAbS19_II06640 |
| *Mycobacterium leprae* TN | 15828281 | ML2387 |
| *Haloquadratum walsbyi* DSM 16790 | 110667061 | HQ1085A |
| *Listeria monocytogenes* HCC23 | 217964852 | LMHCC_1572 |
| *Bacillus subtilis* subsp. *spizizenii* TU-B-10 | 350265765 | GYO_1800 |
| *Halomicrobium mukohataei* DSM 12286 | 257387048 | Hmuk_0985 |
| *Burkholderia mallei* NCTC 10229 | 124381655 | BMA10229_1319 |
| *Burkholderia thailandensis* E264 | 83717960 | BTH_II2301 |
| *Pseudomonas aeruginosa* LESB58 | 218891776 | PLES_30541 |
| *Sinorhizobium fredii* NGR234 | 227823515 | NGR_c29920 |
| *Geobacllus* sp. C56-T3 | 297530772 | GC56T3_2512 |
| *Brucella microti* CCM 4915 | 256015306 | BMI_II521 |
| *Haloarcula marismortui* ATCC 43049 | 55379543 | rrnAC2953 |
| *Listeria monocytogenes* serotype 4b str. F2365 | 46907287 | LMOf2365_1076 |
| *Bacillus weihenstephanensis* KBAB4 | 163941709 | BcerKBAB4_3796 |
| *Burkholderia pseudomallei* K96243 | 53723288 | BPSS2270 |
| *Brachyspira murdochii* DSM 12563 | 296125823 | Bmur_0777 |
| *Thermoanaerobacterium thermosaccharolyticum* DSM 571 | 304317378 | Tthe_1955 |
| *Mycobacterium ulcerans* Agy99 | 118617748 | MUL_2214 |
| *Burkholderia mallei* ATCC 23344 | 53716068 | BMAA2010 |
| *Macrococcus caseolyticus* JCSC5402 | 222150963 | MCCL_0713 |
| *Desulfovibrio vulgaris* str. 'Miyazaki F' | 218886000 | DvMF_0898 |
| *Staphylococcus aureus* subsp. *aureus* JH1 | 150393644 | SaurJH1_1178 |
| *Burkholderia cenocepacia* AU 1054 | 107022321 | Bcen_0765 |
| *Mycobacterium marinum* M | 183980809 | MMAR_0785 |
| *Oceanobacillus iheyensis* HTE831 | 23098870 | OB1415 |
| *Lactobacillus plantarum* WCFS1 | 380032902 | lp_2151 |
| *Staphylococcus haemolyticus* JCSC1435 | 70726857 | SH1856 |
| *Lactobacillus fermentum* IFO 3956 | 184155613 | LAF_1137 |
| *Bacillus amyloliquefaciens* FZB42 | 154685878 | RBAM_014450 |
| *Staphylococcus aureus* subsp. *aureus* MW2 | 21282708 | MW0979 |
| *Pseudomonas aeruginosa* UCBPP-PA14 | 116050197 | PA14_35490 |
| *Thermoplasma volcanium* GSS1 | 13540930 | TVN0099 |
| *Sulfolobus solfataricus* P2 | 15899410 | SSO2689 |
| *Bacillus megaterium* DSM 319 | 295703465 | BMD_1329 |
| *Paembacillus polymyxa* E681 | 308069292 | PPE_02529 |
| *Lactobacillus casei* BL23 | 191638312 | LCABL_15390 |
| *Pseudomonas entomophila* L48 | 104782860 | PSEEN3856 |
| *Halorubrum lacusprofundi* ATCC 49239 | 222478581 | Hlac_0142 |
| *Geobacillus kaustophilus* HTA426 | 56419596 | GK1061 |
| *Staphylococcus aureus* subsp. *aureus* USA300_FPR3757 | 87161349 | SAUSA300_0996 |
| *actobacillus rhamnosus* GG NC_013198 | 258508318 | LGG_01323 |
| *Staphylococcus aureus* RF122 | 82750706 | SAB0962 |
| *Burkholderia cenocepacla* MC0-3 | 170732569 | Bcenmc03_1219 |
| *Thermoanaerobacter pseudethanolicus* ATCC 33223 | 167037200 | Teth39_0785 |
| *Bacillus cereus* biovar *anthracis* str. CI | 301055460 | BACI_c39260 |
| *Burkholderia cenocepacia* HI2424 | 116689268 | Bcen2424_1246 |
| *Oenococcus oeni* PSU-1 | 116490427 | OEOE_0331 |
| *Listeria monocytogenes* 08-5578 | 284801387 | LM5578_1138 |
| *Clostridium tetani* E88 | 28211667 | CTC02047 |
| *Thermoanaerobacterium xylanolyticum* LX-11 | 333896751 | Thexy_0914 |
| *Brachyspira pilosicoli* 95/1000 uncultured methanogenic archaeon RC-I | 300869836 147919055 | BP951000_0199 RRC122 |
| *Staphylococcus aureus* subsp. *aureus* N315 | 15926681 | SA0946 |
| *Erysipelothrix rhusiopathiae* str. Fujisawa | 336065681 | ERH_0441 |
| *Mycobacterium leprae* Br4923 | 221230758 | MLBr_02387 |
| *Lactobacillus plantarum* JDM1 | 254556969 | JDM1_1802 |
| *Pyrobaculum arsenaticum* DSM 13514 | 145591423 | Pars_1205 |
| *Mycoplasma bovis* PG45 | 313678233 | MBOVPG45_0108 |
| *Bacillus thuringiensis* BMB171 | 296504463 | BMB171_C3633 |
| *Arcobacter butzleri* RM4018 | 157737715 | Abu_1474 |
| *Mycobacterium avium* subsp. *paratuberculosis* K-10 | 41410054 | MAP3956 |
| *Brucella melitensis* biovar Abortus 2308 | 83269595 | BAB2_0712 |
| *Ramlibacter tataouinensis* TTB310 | 337278684 | Rta_10510 |
| *Ochrobactrum anthropi* ATCC 49188 | 153010875 | Oant_3554 |
| *Bacillus subtilis* BSn5 | 321315220 | BSn5_19380 |
| *Pseudomonas putida* GB-1 | 167034960 | PputGB1_3965 |
| *Bacillus cereus* Q1 | 222097418 | BCQ_3758 |
| *Arcobacter nitrofigilis* DSM 7299 | 296274130 | Arnit_2606 |
| *Anoxybacillus flavithermus* WK1 | 212639717 | Aflv_1891 |
| *Lactobacillus brevis* ATCC 367 | 116334009 | LVIS_1407 |
| *Bacillus cereus* AH187 | 217961455 | BCAH187_A4088 |
| *Burkholderia ambifaria* AMMD | 115351179 | Bamb_1126 |
| *Sinorhizobium medicae* WSM419 | 150398027 | Smed_2829 |
| *Halogeometricum borinquense* DSM 11551 | 313125079 | Hbor_02940 |
| *Halalkalicoccus jeotgali* B3 | 300709398 | HacjB3_00135 |
| *Lysinibacilius sphaericus* C3-41 | 169826946 | Bsph_1366 |
| *Exiguobacterium sibiricum* | 172061477 | Exig_2008 |
| *Geobacillus* sp. Y4.1MC1 255-15 | 312111828 | GY4MC1_2838 |
| *Anaeromyxobacter* sp. Fw109-5 | 153004860 | Anae109_1998 |
| *Listeria monocytogenes* EGD-e | 16803095 | lmo1055 |
| *Carnobacterium* sp. 17-4 | 328957244 | CAR_c09210 |

TABLE 5-continued

IpdV Genes

| Genome | Gene ID# | Locus Tag |
|---|---|---|
| Campylobacter concisus 13826 | 157164634 | CCC13826_0588 |
| Pusillimonas sp. T7-7 | 332284092 | PT7_0839 |
| Sulfolobus acidocaldarius DSM 639 | 70607437 | Saci_1708 |
| Pediococcus pentosaceus ATCC 25745 | 116493498 | PEPE_1170 |
| Lactobacillus reuteri JCM 1112 | 184153266 | LAR_0611 |
| Paenibacillus polymyxa SC2 | 310642334 | PPSC2_c2886 |
| Pyrobaculum aerophilum str. IM2 | 18313492 | PAE2649 |
| Halorhabdus utahensis DSM 12940 | 257052876 | Huta_1805 |
| Thermoanaerobacter tengcongensis MB4 | 20806617 | TTE0088 |
| Brevibacillus brevis NBRC 100599 | 226312882 | BBR47_32950 |
| Brachyspira hyodysenteriae WA1 | 225621390 | BHWA1_02490 |
| Listeria monocytogenes 08-5923 | 284994529 | LM5923_1092 |
| Listeria welshimeri serovar 6b str. SLCC5334 | 116872449 | lwe1031 |
| Picrophilus torridus DSM 9790 | 48477618 | PTO0546 |
| Staphylococcus aureus subsp. aureus str. Newman | 151221174 | NWMN_0962 |
| Geobacillus sp. Y412MC52 | 319766074 | GYMC52_0961 |
| Listeria monocytogenes serotype 4b str. CLIP 80459 | 226223673 | Lm4b_01075 |
| Sinorhizobium meliloti AK83 | 334317693 | Sinme_2991 |
| Desulfomicrobium baculatum DSM 4028 | 256828156 | Dbac_0341 |
| Pseudomonas putida W619 | 170722908 | PputW619_3745 |

Enzymatic Capability 3: Oxidation of Isobutyryl-CoA to Methacrylyl-CoA

A third step in the MMA precursor bioproduction process is the oxidation of isobutyryl-CoA to (methacrylic acid)-coA (MAA-CoA). This step may be performed by a suitable enzyme, such as an isobutryl-coA dehydrogenase enzyme.

The host microorganism may be transformed to express one or more isobutyrylcoA dehydrogenase or equivalent enzymes. For example, the host microorganism may be engineered to express the *Pseudomonas aeruginosa* ACD1 gene (Genbank Accession Number NP 249437) or an equivalent gene. Other isobutyryl-CoA dehydrogenase enzymes that may be used are listed in Table 6.

TABLE 6

ACD1 Genes

| Genome | Gene ID# | Locus Tag |
|---|---|---|
| Glaciecola nitratireducens FR1064 | 348029414 | GNIT_1998 |
| Alcanivorax dieselolei B5 | 407698116 | B5T_04301 |
| Gordonia polyisoprenivorans VH2 | 378719237 | GPOL_c37480 |
| Pseudogulbenkiania sp. NH8B | 347540610 | NH8B_2828 |
| Alteromonas macleodii ATCC 27126 | 406596805 | MASE_09250 |
| Phaeobacter gallaeciensis 2.10 | 400754588 | PGA2_c17140 |
| Xanthomonas oryzae pv. oryzicola BLS256 | 384420101 | XOC_3195 |
| Mycobacterium chubuense NBB4 | 392414871 | Mycch_0987 |

TABLE 6-continued

ACD1 Genes

| Genome | Gene ID# | Locus Tag |
|---|---|---|
| Mycobacterium canettii CIPT 140010059 | 340625771 | MCAN_07561 |
| Pseudoxanthomonas spadix BD-a59 | 357416594 | DSC_04600 |
| Mycobacterium tuberculosis UT205 | 392385470 | UDA_0752c |
| Collimonas fungivorans Ter331 | 340785743 | CFU_0549 |
| Mycobacterium tuberculosis CTRI-2 | 385997532 | MTCTRI2_0769 |
| Mycobacterium intracellulare ATCC 13950 | 379749004 | OCU_42850 |
| Xanthomonas campestris pv. raphani 756C | 384427173 | XCR_1514 |
| Bordetella pertussis CS | 384203847 | BPTD_1429 |
| Nocardiopsis alba ATCC BAA-2165 | 403509890 | B005_2435 |
| Mycobacterium tuberculosis RGTB327 | 383306654 | MRGA327_04680 |
| Mycobacterium massiliense str. GO 06 | 397678864 | MYCMA_0631 |
| Rhodospirillum rubrum F11 | 386349902 | F11_09435 |
| Rhodospirillum photometricum DSM 122 | 384262441 | RSPPHO_02032 |
| Mycobacterium tuberculosis RGTB423 | 386003783 | MRGA423_04680 |
| Mycobacterium tuberculosis H37Rv | 397672563 | RVBD_0752c |
| Mycobacterium bovis BCG str. Mexico | 378770509 | BCGMEX_0774c |
| Shewanella baltica BA175 | 386325263 | Sbal175_2834 |
| Streptomyces cattleya NRRL 8057 = DSM 46488 NC_017586 | 386359035 | SCATT_53870 |
| Bradyrhizobium japonicum USDA 6 | 384219558 | BJ6T_58810 |
| Brucella melitensis M5-90 | 384211682 | BM590_A1316 |
| Alteromonas macleodii str. 'English Channel 673' | 407683813 | AMEC673_09580 |
| Tistrella mobilis KA081020-065 | 389877230 | TMO_1372 |
| Roseobacter litoralis Och 149 | 339504104 | RLO149_c025980 |
| Streptomyces hygroscopicus subsp. jinggangensis 5008 | 386838951 | SHJG_2862 |
| Marinobacter hydrocarbonoclasticus ATCC 49840 | 387813520 | MARHY1099 |
| Pseudomonas aeruginosa NCGM2.S1 | 386064418 | NCGM2_1472 |
| Alteromonas macleodii str. 'Balearic Sea AD45' | 407687740 | AMBAS45_09805 |
| Mycobacterium intracellulare MOTT-02 | 379756320 | OCO_43080 |
| Vibrio furnissii NCTC 11218 | 375133520 | vfu_B01430 |
| Shewanella baltica OS117 | 386340494 | Sbal117_1607 |
| Mycobacterium rhodesiae NBB3 | 375137842 | MycrhN_0640 |
| Brucella melitensis NI | 384445362 | BMNI_I1275 |
| Desulfomonile tiedjei DSM 6799 | 392411422 | Desti_3103 |
| Mycobacterium africanum GM041182 | 339630821 | MAF_07630 |
| Brucella canis HSK A52141 | 376276076 | BCA52141_I3086 |
| Pseudomonas aeruginosa M18 | 386060354 | PAM18_4293 |
| Xanthomonas axonopodis pv. citrumelo F1 | 346724209 | XACM_1296 |

TABLE 6-continued

ACD1 Genes

| Genome | Gene ID# | Locus Tag |
|---|---|---|
| Gordonia sp. KTR9 | 404216431 | KTR9_3836 |
| Shewanella baltica OS678 | 378707897 | Sbal678_1564 |
| Alteromonas macleodii str. 'Black Sea 11' | 407700062 | AMBLS11_09065 |
| Legionella pneumophila subsp. pneumophila NC_018140 | 397666547 | LPV_1001 |
| Marinobacter adhaerens HP15 | 385330648 | HP15_907 |
| Mycobacterium tuberculosis KZN 605 | 392431180 | TBXG_000759 |
| Stenotrophomonas maltophilia JV3 | 344205641 | BurJV3_0221 |
| Legionella pneumophila subsp. pneumophila ATCC 43290 | 378776822 | lp12_0890 |
| Brucella melitensis M28 | 384408789 | BM28_A1325 |
| Bradyrhizobium sp. S23321 | 383772525 | S23_42840 |
| Mycobacterium tuberculosis CCDC5079 | 385993820 | CCDC5079_0695 |
| Stenotrophomonas maltophilia D457 | 386716688 | SMD_0230 |
| Legionella pneumophila subsp. pneumophila NC_018139 | 397663427 | LPO_0948 |
| Oceanimonas sp. GK1 | 374336854 | GU3_15190 |
| Shewanella putrefaciens 200 | 386313180 | Sput200_1414 |
| Brucella pinnipedialis B2/94 | 340790932 | BPI_I1367 |
| Kitasatospora setae KM-6054 | 357387288 | KSE_03230 |
| Mycobacterium tuberculosis CCDC5180 | 385990221 | CCDC5180_0687 |
| Sinorhizobium fredii USDA 257 | 398351439 | USDA257_c15560 |
| Phaeobacter gallaeciensis DSM 17395 | 399992913 | PGA1_c17340 |
| Mycobacterium tuberculosis KZN 4207 | 375294971 | TBSG_00770 |
| Legionella pneumophila str. Lens | 54293844 | lpl0900 |
| Aeromonas salmonicida subsp. salmonicida A449 | 145298895 | ASA_1914 |
| Azorhizobium caulinodans ORS 571 | 158422200 | AZC_0576 |
| Shewanella woodyi ATCC 51908 | 170727539 | Swoo_3200 |
| Shewanella denitrificans OS217 | 91793296 | Sden_1941 |
| Rhodomicrobium vannielii ATCC 17100 | 312116097 | Rvan_3412 |
| Vibrio vulnificus YJ016 | 37676701 | VVA1041 |
| Xanthobacter autotrophicus Py2 | 154246133 | Xaut_2190 |
| Vibrio sp. Ex25 | 262396842 | VEA_001547 |
| Shewanella oneidensis MR-1 | 24373247 | SO_1679 |
| Shewanella halifaxensis HAW-EB4 | 167624790 | Shal_2876 |
| Rhodococcus erythropolis PR4 | 226307441 | RER_39540 |
| Pseudoalteromonas atlantica T6c | 109897274 | Patl_0949 |
| Legionella pneumophila str. Paris | 54296890 | lpp0931 |
| Rhodospirillum centenum SW | 209964651 | RC1_1349 |
| Pseudomonas mendocina NK-01 | 330502345 | MDS_1431 |
| Laribacter hongkongensis HLHK9 | 226939151 | LHK_00217 |
| Bradyrhizobium japonicum USDA 110 | 27379066 | blr3955 |
| Rhodobacter sphaeroides ATCC 17025 | 146277380 | Rsph17025_1335 |
| Legionella longbeachae NSW150 | 289164236 | LLO_0891 |
| Brucella melitensis ATCC 23457 | 225852804 | BMEA_A1361 |
| Chelativorans sp. BNC1 | 110632946 | Meso_0589 |
| Arthrobacter arilaitensis Re117 | 308178599 | AARI_28290 |
| Vibrio vulnificus CMCP6 | 27366926 | VV2_0492 |
| Aeromonas hydrophila subsp. hydrophila ATCC 7966 | 117620593 | AHA_2080 |
| Polymorphum gilvum SL003B-26A1 | 328543528 | SL003B_1909 |
| Shewanella loihica PV-4 | 127512598 | Shew_1669 |
| Mycobacterium tuberculosis H37Ra | 148660528 | MRA_0761 |
| Shewanella baltica OS185 | 153000023 | Shew185_1491 |
| Variovorax paradoxus EPS | 319793062 | Varpa_2389 |
| Microbacterium testaceum StLB037 | 323358382 | MTES_1934 |
| Vibrio parahaemolyticus RIMD 2210633 | 28900477 | VPA0622 |
| Xanthomonas campestris pv. campestris str. 8004 | 66769286 | XC_2980 |
| Rhodopseudomonas palustris BisB18 | 90424584 | RPC_3093 |
| Rhodospirillum rubrum ATCC 11170 | 83593170 | Rru_A1835 |
| Mesorhizobium ciceri biovar biserrulae WSM1271 | 319783100 | Mesci_3403 |
| Ferroglobus placidus DSM 10642 | 288931943 | Ferp_579 |
| Streptomyces cattleya NRRL 8057 = DSM 46488 NC_016111 | 357402954 | SCAT_5388 |
| Mycobacterium tuberculosis KZN 1435 | 253797697 | TBMG_00766 |
| Alicycliphilus denitrificans BC | 319763240 | Alide_2557 |
| Brucella abortus A13334 | 376272954 | BAA13334_I01881 |
| Alicycliphilus denitrificans K601 | 330825434 | Alide2_2873 |
| Sphingomonas wittichii RW1 | 148553574 | Swit_0650 |
| Nakamurella multipartita DSM 44233 | 258654336 | Namu_4214 |
| Psychrobacter sp. PRwf-1 | 148652112 | PsycPRwf_0300 |
| Pseudoalteromonas sp. SM9913 | 315126581 | PSM_A1501 |
| Rhodobacter capsulatus SB 1003 | 294677101 | RCAP_rcc01564 |
| Shewanella sediminis HAW-EB3 | 157374614 | Ssed_1475 |
| Acidovorax avenae subsp. avenae ATCC 19860 | 326317408 | Acav_2601 |
| Rhodopseudomonas palustris CGA009 | 39936511 | RPA3448 |
| Comamonas testosteroni CNB-1 | 264678921 | CtCNB1_2786 |
| Brucella abortus bv. 1 str. 9-941 | 62290217 | BruAb1_1314 |
| Pseudomonas aeruginosa DK2 | 392985774 | PADK2_21970 |
| Brevundimonas subvibrioides ATCC 15264 | 302382986 | Bresu_1875 |
| Sphingobium chlorophenolicum L-1 | 334344716 | Sphch_1072 |

TABLE 6-continued

ACD1 Genes

| Genome | Gene ID# | Locus Tag |
|---|---|---|
| Shewanella sp. MR-7 | 114048154 | Shewmr7_2662 |
| Hahella chejuensis KCTC 2396 | 83643532 | HCH_00641 |
| Shewanella violacea DSS12 | 294141872 | SVI_3101 |
| Mycobacterium bovis AF2122/97 | 31791939 | Mb0774c |
| Novosphingobium aromaticivorans DSM 12444 | 87198880 | Saro_0858 |
| Rhodopseudomonas palustris BisA53 | 115524393 | RPE_2385 |
| Bordetella bronchiseptica RB50 | 33601607 | BB2630 |
| Nitrobacter winogradskyi Nb-255 | 75676343 | Nwi_2158 |
| Xanthomonas oryzae pv. oryzae KACC10331 | 58581466 | XOO1843 |
| Bradyrhizobium sp. BTAi1 | 148254990 | BBta_3579 |
| Nocardia cyriacigeorgica GUH-2 | 379707353 | NOCYR_1108 |
| Xanthomonas axonopodis pv. citri str. 306 | 21242066 | XAC1313 |
| Mycobacterium avium 104 | 118465062 | MAV_4418 |
| Shewanella frigidimarina NCIMB 400 | 114562518 | Sfri_1340 |
| Hirschia baltica ATCC 49814 | 254295049 | Hbal_2701 |
| Mesorhizobium opportunistum WSM2075 | 337268363 | Mesop_3886 |
| Shewanella baltica OS155 | 126173735 | Sbal_1497 |
| Stenotrophomonas maltophilia K279a | 190572339 | Smlt0265 |
| Vibrio harveyi ATCC BAA-1116 | 156976709 | VIBHAR_05484 |
| Mycobacterium bovis BCG str. Tokyo 172 | 224989147 | JTY_0773 |
| Bordetella petrii DSM 12804 | 163856823 | Bpet2511 |
| Brucella ovis ATCC 25840 | 148560349 | BOV_1275 |
| Micrococcus luteus NCTC 2665 | 239916835 | Mlut_02820 |
| Colwellia psychrerythraea 34H | 71279027 | CPS_0658 |
| Pseudovibrio sp. FO-BEG1 | 374331938 | PSE_3596 |
| Mesorhizobium loti MAFF303099 | 13471277 | mlr1201 |
| Psychrobacter cryohalolentis K5 | 93006342 | Pcryo_1516 |
| Rhodobacter sphaeroides KD131 | 221639593 | RSKD131_1494 |
| Pseudomonas aeruginosa PA7 | 152984346 | PSPA7_4774 |
| Acidianus hospitalis W1 | 332795998 | Ahos_0309 |
| Acidovorax citrulli AAC00-1 | 120611270 | Aave_2602 |
|  | 15607892 | Rv0752c |
| Isosphaera pallida ATCC 43644 | 320105221 | Isop_3707 |
| Maricaulis maris MCS10 | 114570096 | Mmar10_1546 |
| Aeromonas veronii B565 | 330829883 | B565_2183 |
| Xanthomonas campestris pv. campestris str. ATCC 33913 | 21230718 | XCC1261 |
| Methylobacterium sp. 4-46 | 170740707 | M446_2476 |
| Dinoroseobacter shibae DFL 12 | 159044299 | Dshi_1750 |
| Bordetella pertussis Tohama I | 33592543 | BP1445 |
| Rhodococcus opacus B4 | 226360658 | ROP_12440 |
| Rhodococcus opacus B4 | 226363908 | ROP_44980 |
| Brucella melitensis bv. 1 str. 16M | 17986972 | BMEI0689 |
| Shewanella baltica OS195 | 160874644 | Sbal195_1527 |
| Acidothermus cellulolyticus 11B | 117927618 | Acel_0409 |
| Xanthomonas campestris pv. vesicatoria str. 85-10 | 78046920 | XCV1364 |
| Variovorax paradoxus S110 | 239816229 | Vapar_3255 |
| Ruegeria pomeroyi DSS-3 | 56697074 | SPO2211 |
| Achromobacter xylosoxidans A8 | 311106012 | AXYL_02830 |
| Ruegeria sp. TM1040 | 99080944 | TM1040_1103 |
| Beijerinckia indica subsp. Indica ATCC 9039 | 182677610 | Bind_0617 |
| Nitrobacter hamburgensis X14 | 92118071 | Nham_2558 |
| Pseudoalteromonas haloplanktis TAC125 | 77360399 | PSHAa1456 |
| Caulobacter crescentus NA1000 | 221234349 | CCNA_01412 |
| Stenotrophomonas maltophilia R551-3 | 194363998 | Smal_0220 |
| Hyphomonas neptunium ATCC 15444 | 114800043 | HNE_0900 |
| Sphingobium japonicum UT26S | 294012056 | SJA_C1-20700 |
| Shewanella sp. W3-18-1 | 120599501 | Sputw3181_2702 |
| Nocardia farcinica IFM 10152 | 54023005 | nfa10380 |
| Nocardiopsis dassonvillei subsp. dassonvillei DSM 43111 | 297563334 | Ndas_4413 |
| Chromobacterium violaceum ATCC 12472 | 34497539 | CV_2084 |
| Nocardioides sp. JS614 | 119715626 | Noca_1390 |
| Shewanella baltica OS223 | 217974012 | Sbal223_2854 |
| Vibrio sp. EJY3 | 375263283 | VEJY3_20606 |
| Roseobacter denitrificans OCh 114 | 110679512 | RD1_2243 |
| Mycobacterium sp. MOTT36Y | 387877677 | W7S_21525 |
| Acidovorax ebreus TPSY | 222111004 | Dtpsy_1811 |
| Idiomarina loihiensis L2TR | 56459977 | IL0869 |
| Caulobacter sp. K31 | 167647017 | Caul_3055 |
| Herbaspirillum seropedicae SmR1 | 300311865 | Hsero_2550 |
| Caulobacter crescentus CB15 | 16125599 | CC_1350 |
| Shewanella pealeana ATCC 700345 | 157962602 | Spea_2781 |
| Mycobacterium sp. JDM601 | 333991932 | JDM601_3292 |
| Rhodopseudomonas palustris TIE-1 | 192292303 | Rpal_3937 |
| Syntrophus aciditrophicus SB | 85858067 | SYN_02587 |
| Rhodococcus equi 103S | 312139135 | REQ_17170 |
| Mycobacterium smegmatis str. MC2 155 NC_018289 | 399985881 | MSMEI_1461 |
| Shewanella amazonensis SB2B | 119774514 | Sama_1377 |
| Brucella abortus S19 | 189024452 | BAbS19_I12450 |
| Magnetospirillum magneticum AMB-1 | 83312685 | amb3586 |
| Novosphingobium sp. PP1Y | 334141518 | PP1Y_AT20310 |
| Xanthomonas oryzae pv. oryzae PXO99A | 188577295 | PXO_01704 |
| Thermobifida fusca YX | 72162048 | Tfu_1647 |
| Rhodopseudomonas palustris HaA2 | 86749241 | RPB_2120 |

TABLE 6-continued

ACD1 Genes

| Genome | Gene ID# | Locus Tag |
|---|---|---|
| Halomonas elongata DSM 2581 | 307545013 | HELO_2423 |
| Pseudomonas aeruginosa LESB58 | 218893310 | PLES_45971 |
| Mycobacterium tuberculosis CDC1551 | 15840166 | MT0776 |
| Bordetella avium 197N | 187478253 | BAV1758 |
| Parvibaculum lavamentivorans DS-1 | 154253338 | Plav_2898 |
| Alteromonas macleodii str. 'Deep ecotype' | 332141327 | MADE_1009645 |
| Bordetella parapertussis 12822 | 33596196 | BPP1552 |
| Brucella microti CCM 4915 | 256369734 | BMI_I1326 |
| Gordonia bronchialis DSM 43247 | 262203762 | Gbro_3901 |
| Sphingopyxis alaskensis RB2256 | 103488529 | Sala_3053 |
| Mycobacterium intracellulare MOTT-64 | 379763856 | OCQ_44200 |
| Xanthomonas oryzae pv. oryzae MAFF 311018 | 84623396 | XOO_1739 |
| Rhodopseudomonas palustris BisB5 | 91977767 | RPD_3301 |
| Mycobacterium sp. Spyr1 | 315445940 | Mspyr1_44290 |
| Caulobacter segnis ATCC 21756 | 295689060 | Cseg_1650 |
| Shewanella sp. ANA-3 | 117921210 | Shewana3_2769 |
| Shewanella putrefaciens CN-32 | 146292501 | Sputcn32_1399 |
| Rhodobacter sphaeroides ATCC 17029 | 126462554 | Rsph17029_1789 |
| Mycobacterium ulcerans Agy99 | 118616613 | MUL_0836 |
| Mycobacterium sp. MCS | 108798036 | Mmcs_1063 |
| Mycobacterium marinum M | 183981098 | MMAR_1078 |
| Catenulispora acidiphila DSM 44928 | 256393670 | Caci_4530 |
| Mycobacterium bovis BCG str. Pasteur 1173P2 | 121636675 | BCG_0803c |
| Pseudomonas aeruginosa UCBPP-PA14 | 116048661 | PA14_54630 |
| Methylobacterium radiotolerans JCM 2831 | 170750182 | Mrad2831_3784 |
| Acidovorax sp. JS42 | 121594363 | Ajs_2007 |
| Photobacterium profundum SS9 | 54302789 | PBPRB1110 |
| Phenylobacterium zucineum HLK1 | 197105143 | PHZ_c1680 |
| Paracoccus denitrificans PD1222 | 119387185 | Pden_4480 |
| Alteromonas sp. SN2 | 333893005 | ambt_07750 |
| Shewanella sp. MR-4 | 113970930 | Shewmr4_2595 |
| Streptomyces avermitilis MA-4680 | 29833461 | SAV_6919 |
| Rhodopseudomonas palustris DX-1 | 316933290 | Rpdx1_1928 |
| Verminephrobacter eiseniae EF01-2 | 121610468 | Veis_3538 |
| Vibrio vulnificus MO6-24/O | 320158804 | VVM_01997 |
| Mycobacterium avium subsp. paratuberculosis K 10 | 41410312 | MAP4214c |
| Brucella melitensis biovar Abortus 2308 | 82700138 | BAB1_1333 |
| Rhodococcus jostii RHA1 | 111024023 | RHA1_ro07073 |
| Ochrobactrum anthropi ATCC 49188 | 153009201 | Oant_1871 |
| Erythrobacter litoralis HTCC2594 | 85374832 | ELI_10025 |
| Actinosynnema mirum DSM 43827 | 256380353 | Amir_6366 |
| Mycobacterium sp. KMS | 119867131 | Mkms_1079 |
| Amycolicicoccus subflavus DQS3-9A1 | 333920326 | AS9A_2660 |
| Mycobacterium vanbaalenii PYR-1 | 120402372 | Mvan_1361 |
| Legionella pneumophila str. Corby | 148360485 | LPC_2425 |
| Legionella pneumophila subsp. pneumophila str. Philadelphia 1 | 52841104 | lpg0868 |
| Acidiphilium multivorum AIU301 | 326403394 | ACMV_12460 |
| Legionella pneumophila 2300/99 Alcoy | 296106448 | lpa_01311 |
| Mycobacterium gilvum PYR-GCK | 145225587 | Mflv_5011 |
| Acidiphilium cryptum JF-5 | 148259637 | Acry_0623 |
| Xanthomonas campestris pv. campestris str. B100 | 188992437 | xccb100_3042 |
| Delftia acidovorans SPH-1 | 160899128 | Daci_3693 |
| Bradyrhizobium sp. ORS278 | 146340123 | BRADO3138 |
| Psychrobacter arcticus 273-4 | 71065461 | Psyc_0901 |
| Methylobacterium nodulans ORS 2060 | 220922160 | Mnod_2176 |
| Rhodobacter sphaeroides 2.4.1 | 77463725 | RSP_0156 |
| Carnobacterium sp. 17-4 | 328958473 | CAR_c21860 |
| Alcanivorax borkumensis SK2 | 110832882 | ABO_0021 |
| Saccharopolyspora erythraea NRRL 2338 | 134098043 | SACE_1457 |
| Pusillimonas sp. T7-7 | 332284306 | PT7_1053 |
| Shewanella piezotolerans WP3 | 212636148 | swp_3385 |
| Tsukamurella paurometabola DSM 20162 | 296140757 | Tpau_3069 |
| Streptomyces griseus subsp. griseus NBRC 13350 | 182435009 | SGR_1216 |
| Mycobacterium smegmatis str. MC2 155 NC_008596 | 118472185 | MSMEG_1497 |
| Jannaschia sp. CCS1 | 89054400 | Jann_1909 |
| Mycobacterium abscessus ATCC 19977 | 169628281 | MAB_1188c |
| Mycobacterium tuberculosis F11 | 148821957 | TBFG_10766 |
| Glaciecola sp. 4H-3-7 + YE5 | 332307811 | Glaag_3460 |
| Marinobacter aquaeolei VT8 | 120555047 | Maqu_2132 |
| Mycobacterium sp. JLS | 126433697 | Mjls_1090 |
| Pseudomonas mendocina ymp | 146306407 | Pmen_1375 |
| Ferrimonas balearica DSM 9799 | 308048737 | Fbal_1020 |
| Sinorhizobium meliloti AK83 | 334320231 | sinme_4289 |

Enzymatic Capability 4: From 3-Hydroxyisobutyryl-CoA to MAA-CoA

In the bioproduction of 3-HIB from valine, one step is the conversion of MAA-CoA to 3-hydroxyisobutyryl-CoA. This may be accomplished by a suitable enzyme, such as an enoyl-CoA hydratase.

The host microorganism may be transformed to express one or more enoyl-coA hydratase (ECH) or equivalent enzymes. For example, the host microorganism may be engineered to express the Pseudomonas aeruginosa echA gene (Genbank Accession Number NP 249436) or an equivalent gene. Alternatively, an ECH gene selected from Table 7 may be used.

Enzymatic Capability 5: From 3-Hydroxyisobutyryl-CoA to 3-HIB

In the bioproduction of 3-HIB from valine, the final enzymatic step is the conversion of 3-hydroxyisobutyryl-CoA to 3-HIB by cleaving of the CoA from 3-hydroxyisobutyryl. This may be accomplished by a suitable enzyme, such as a thioesterase.

The host microorganism may be transformed to express one or more enzymes that creave CoA from 3-hydroxyisobutyryl-CoA. For example, the host microorganism may be transformed to express one or more thioesterase enzymes that cleave CoA from 3-hydroxyisobutyryl-CoA (HCH genes). For example, the host microorganism may be engineered to express the *Pseudomonas aeruginosa* hchA gene (Genbank Accession Number NP 249435) or an equivalent gene. Alternatively, an HCH gene selected from Table 7 may be used.

TABLE 7

| Genome | Gene ID# | Locus Tag |
| --- | --- | --- |
| *Desulfosporosinus orientis* DSM 765 | 374994422 | Desor_1769 |
| *Pseudogulbenkiania* sp. NH8B | 347540611 | NH8B_2829 |
| *Methylophaga* sp. JAM7 | 387130393 | Q7C_1447 |
| *Xanthomonas oryzae* pv. *oryzicola* BLS256 | 384420100 | XOC_3194 |
| *Pseudoxanthomonas spadix* BD-a59 | 357416595 | DSC_04605 |
| *Pseudomonas stutzeri* ATCC 17588 = LMG 11199 | 339493199 | PSTAB_1122 |
| *Pseudomonas stutzeri* DSM 4166 | 386019805 | PSTAA_1177 |
| *Pyrobaculum* sp. 1860 | 374326631 | P186_1146 |
| *Collimonas fungivorans* Ter331 | 340785744 | CFU_0550 |
| *Bacillus megaterium* WSH-002 | 384044695 | BMWSH_0519 |
| *Xanthomonas campestris* pv. *raphani* 756C | 384427174 | XCR_1515 |
| *Amycolatopsis mediterranei* S699 NC_017186 | 384149061 | RAM_19670 |
| *Leptospira interrogans* serovar Lai str. IPAV | 386073441 | LIF_A0972 |
| *Turneriella parva* DSM 21527 | 392405679 | Turpa_4152 |
| *Shewanella baltica* BA175 | 386325262 | Sbal175_2833 |
| *Ornithobacterium rhinotracheale* DSM 15997 | 392390035 | Ornrh_0644 |
| *Marinobacter hydrocarbonoclasticus* ATCC 49840 | 387813521 | MARHY1100 |
| *Pseudomonas aeruginosa* NCGM2.S1 | 386064417 | NCGM2_1471 |
| *Vibrio furnissii* NCTC 11218 | 375133521 | vfu_B01431 |
| *Burkholderia* sp. KJ006 | 387903700 | MYA_2947 |
| *Shewanella baltica* OS117 | 386340495 | Sbal117_1608 |
| *Pseudomonas aeruginosa* M18 | 386060355 | PAM18_4294 |
| *Xanthomonas axonopodis* pv. *citrumelo* F1 | 346724210 | XACM_1297 |
| *Pseudomonas stutzeri* DSM 10701 | 397686059 | PSJM300_04720 |
| *Amycolatopsis mediterranei* S699 V2 NC_018266 | 399537636 | AMES_3817 |

TABLE 7-continued

| Genome | Gene ID# | Locus Tag |
| --- | --- | --- |
| *Shewanella baltica* OS678 | 378707898 | Sbal678_1565 |
| *Flavobacterium indicum* GPTSA100-9 | 383449484 | KQS_00745 |
| *Marinobacter adhaerens* HP15 | 385330649 | HP15_908 |
| *Burkholderia cepacia* GG4 | 402568213 | GEM_3472 |
| *Stenotrophomonas maltophilia* JV3 | 344205642 | BurJV3_0222 |
| *Pseudomonas stutzeri* CCUG 29243 | 392420207 | A458_05710 |
| *Bacillus cereus* F837/76 | 376267399 | bcf_17380 |
| *Stenotrophomonas maltophilia* D457 | 386716689 | SMD_0231 |
| *Burkholderia pseudomallei* 1026b | 386864395 | BP1026B_110685 |
| *Owenweeksia hongkongensis* DSM 17368 | 375013016 | Oweho_2388 |
| *Leptospirillum ferrooxidans* C2-3 | 383785540 | LFE_2308 |
| *Oceanimonas* sp. GK1 | 374336853 | GU3_15185 |
| *Shewanella putrefaciens* 200 | 386313181 | Sput200_1415 |
| *Aeromonas salmonicida* subsp. *salmonicida* A449 | 145298896 | ASA_1915 |
| *Shewanella woodyi* ATCC 51908 | 170727538 | Swoo_3199 |
| *Shewanella denitrificans* OS217 | 91793295 | Sden_1940 |
| *Vibrio vulnificus* YJ016 | 37676700 | VVA1040 |
| *Vibrio* sp. Ex25 | 262395672 | VEA_000372 |
| *Shewanella oneidensis* MR-1 | 24373248 | SO_1680 |
| *Shewanella halifaxensis* HAW-EB4 | 167624789 | Shal_2875 |
| *Planctomyces brasiliensis* DSM 5305 | 325107014 | Plabr_0433 |
| *Sorangium cellulosum* 'So ce 56' | 162454201 | sce5924 |
| *Cupriavidus taiwanensis* LMG 19424 | 194291860 | RALTA_B1107 |
| *Pseudomonas mendocina* NK-01 | 330502344 | MDS_1430 |
| *Laribacter hongkongensis* HLHK9 | 226939152 | LHK_00218 |
| *Croceibacter atlanticus* HTCC2559 | 298207322 | CA2559_03685 |
| *Sideroxydans lithotrophicus* ES-1 | 291613755 | Slit_1288 |
| *Pedobacter saltans* DSM 12145 | 325105493 | Pedsa_2784 |
| *Vibrio vulnificus* CMCP6 | 27366925 | VV2_0491 |
| *Aeromonas hydrophila* subsp. *hydrophila* ATCC 7966 | 117621061 | AHA_2081 |
| *Thioalkalivibrio sulfidophilus* HL-EbGr7 | 220933275 | Tgr7_0083 |
| *Shewanella loihica* PV-4 | 127512599 | Shew_1670 |
| *Shewanella baltica* OS185 | 153000024 | Shew185_1492 |
| *Pseudomonas stutzeri* A1501 | 146281598 | PST_1214 |
| *Ralstonia pickettii* 12D | 241665652 | Rpic12D_4090 |
| *Vibrio parahaemolyticus* RIMD 2210633 | 28900478 | VPA0623 |
| *Xanthomonas campestris* pv. *campestris* str. 8004 | 66769285 | XC_2979 |
| *Xylella fastidiosa* Temecula1 | 28198324 | PD0407 |
| *Burkholderia pseudomallei* 1106a | 126457284 | BURPS1106A_A0830 |

TABLE 7-continued

| Genome | Gene ID# | Locus Tag |
|---|---|---|
| Leptospira interrogans serovar Copenhageni str. Fiocruz L1-130 | 45658337 | LIC12495 |
| Polaromonas sp. JS666 | 91788338 | Bpro_2473 |
| Bacillus cereus E33L | 52142006 | BCZK3237 |
| Geobacillus thermodenitrificans NG80-2 | 138895542 | GTNG_1892 |
| Burkholderia glumae BGR1 | 238024069 | bglu_2g06300 |
| Bacillus thuringiensis str. Al Hakam | 118478779 | BALH_3171 |
| Fluviicola taffensis DSM 16823 | 327403570 | Fluta_1578 |
| Pseudomonas fulva 12-X | 333901441 | Psefu_3258 |
| Burkholderia pseudomallei 668 | 126443955 | BURPS668_A0922 |
| Burkholderia gladioli BSR3 | 330820009 | bgla_2g08970 |
| Azotobacter vinelandii DJ | 226943481 | Avin_13550 |
| Psychrobacter sp. PRwf-1 | 148652111 | PsycPRwf_0299 |
| Pseudoalteromonas sp. SM9913 | 315126582 | PSM_A1502 |
| Ralstonia eutropha JMP134 | 73538090 | Reut_B4260 |
| Shewanella sediminis HAW-EB3 | 157374615 | Ssed_1476 |
| Pseudomonas aeruginosa DK2 | 392985775 | PADK2_21975 |
| Xylella fastidiosa M12 | 170729668 | Xfasm12_0460 |
| Frankla alnl ACN14a | 111219689 | FRAAL0193 |
| Burkholderia phymatum STM815 | 186473921 | Bphy_5130 |
| Shewanella sp. MR-7 | 114048153 | Shewmr7_2661 |
| Hahella chejuensis KCTC 2396 | 83643531 | HCH_00640 |
| Shewanella violacea DSS12 | 294141871 | SVI_3100 |
| Burkholderia sp. CCGE1001 | 323528140 | BC1001_3821 |
| Robiginitalea biformata HTCC2501 | 260061101 | RB2501_05870 |
| Xanthomonas oryzae pv. oryzae KACC10331 | 58581467 | XOO1844 |
| Thiobacillus denitrificans ATCC 25259 | 74318690 | Tbd_2672 |
| Xanthomonas axonopodis pv. citri str. 306 | 21242067 | XAC1314 |
| Burkholderia ambifaria MC40-6 | 172063912 | BamMC406_4900 |
| Burkholderia pseudomallei 1710b | 76818705 | BURPS1710b_A2182 |
| Shewanella frigidimarina NCIMB400 | 114562519 | Sfri_1341 |
| Shewanella baltica OS155 | 126173736 | Sbal_1498 |
| Stenotrophomonas maltophilia K279a | 190572340 | Smlt0266 |
| Vibrio harveyi ATCC BAA-1116 | 156976710 | VIBHAR_05485 |
| Ruminococcus albus 7 | 317056589 | Rumal_1928 |
| Burkholderia xenovorans LB400 | 91780315 | Bxe_C0248 |
| Burkholderia multivorans ATCC 17616 NC_010801 | 189353613 | BMULJ_04857 |
| Colwellia psychrerythraea 34H | 71277850 | CPS_0657 |
| Maribacter sp. HTCC2170 | 305665647 | FB2170_05090 |
| Psychrobacter cryohalolentis K5 | 93006341 | Pcryo_1515 |
| Ralstonia eutropha H16 | 116695134 | H16_B1189 |
| Pseudomonas aeruginosa PA7 | 152986979 | PSPA7_4775 |
| Bacillus atrophaeus 1942 | 311067529 | BATR1942_02825 |
| Aeromonas veronii B565 | 330829882 | B565_2182 |
| Xanthomonas campestris pv. campestris str. ATCC 33913 | 21230719 | XCC1262 |
| Burkholderia cenocepacia J2315 | 206564029 | BCAM2192 |
| Shewanella baltica OS195 | 160874645 | Sbal195_1528 |
| Xanthomonas campestris pv. vesicatoria str. 85-10 | 78046921 | XCV1365 |
| Burkholderia sp. 383 | 78061568 | Bcep18194_B0718 |
| Bacillus pseudofirmus OF4 | 288555720 | BpOF4_13560 |
| Burkholderia multivorans ATCC 17616 NC_010084 | 161520209 | Bmul_3660 |
| Sulfurovum sp. NBC37-1 | 152992154 | SUN_0558 |
| Polynucleobacter necessarius subsp. necessarius STIR1 | 171463376 | Pnec_0628 |
| Pseudoalteromonas haloplanktis TAC125 | 77360400 | PSHAa1457 |
| Xylella fastidiosa subsp. fastidiosa GB514 | 386084484 | XFLM_07430 |
| Stenotrophomonas maltophilia R551-3 | 194363999 | Smal_0221 |
| Shewanella sp. W3-18-1 | 120599500 | Sputw3181_2701 |
| Chromobacterium violaceum ATCC 12472 | 34497538 | CV_2083 |
| Shewanella baltica OS223 | 217974011 | Sbal223_2853 |
| Vibrio sp. EJY3 | 375262877 | VEJY3_18566 |
| Bacillus megaterium QM B1551 | 294501468 | BMQ_4732 |
| Herbaspirillum seropedicae SmR1 | 300311864 | Hsero_2549 |
| Shewanella pealeana ATCC 700345 | 157962601 | Spea_2780 |
| Bacillus cereus 03BB102 | 225865490 | BCA_3601 |
| Ralstonia pickettii 12J | 187926164 | Rpic_3977 |
| Burkholderia vietnamiensis G4 | 134292051 | Bcep1808_3333 |
| Mycobacterium smegmatis str. MC2 155 NC_018289 | 399988423 | MSMEI_4020 |
| Shewanella amazonensis SB2B | 119774515 | Sama_1378 |
| Bacillus cellulosilyticus DSM 2522 | 317129856 | Bcell_3165 |
| Xanthomonas oryzae pv. oryzae PXO99A | 188577294 | PXO_01705 |
| Burkholderia thailandensis E264 | 83717948 | BTH_II1799 |
| Pseudomonas aeruginosa LESB58 | 218893311 | PLES_45981 |
| Xanthomonas oryzae pv. oryzae MAFF 311018 | 84623397 | XOO_1740 |
| Burkholderia phytofirmans PsJN | 187920332 | Bphyt_5646 |
| Shewanella sp. ANA-3 | 117921209 | Shewana3_2768 |
| Shewanella putrefaciens CN-32 | 146292502 | Sputcn32_1400 |
| Burkholderia pseudomallei K96243 | 53721657 | BPSS0621 |
| Cupriavidus necator N-1 | 339322459 | CNE_2c11550 |
| Burkholderia cenocepacia AU 1054 | 107025765 | Bcen_3408 |

TABLE 7-continued

| Genome | Gene ID# | Locus Tag |
|---|---|---|
| Pseudomonas aeruginosa UCBPP-PA14 | 116048660 | PA14_54640 |
| Bacillus megaterium DSM 319 | 295706816 | BMD_4718 |
| Photobacterium profundum SS9 | 54302788 | PBPRB1109 |
| Burkholderia cenocepacia MC0-3 | 170737684 | Bcenmc03_5327 |
| Burkholderia sp. CCGE1003 | 307727573 | BC1003_5577 |
| Burkholderia cenocepacia HI2424 | 116693053 | Bcen2424_4959 |
| Xylella fastidiosa M23 | 182680963 | XfasM23_0401 |
| Shewanella sp. MR-4 | 113970929 | Shewmr4_2594 |
| Amycolatopsis mediterranei U32 | 300785752 | AMED_3862 |
| Vibrio vulnificus MO6-24/O | 320158803 | VVM_01994 |
| Sulfurimonas autotrophica DSM 16294 | 307721221 | Saut_1301 |
| Acaryochloris marina MBIC11017 | 158334786 | AM1_1621 |
| Leptospira interrogans serovar Lai str. 56601 | 24213898 | LA_1198 |
| Leptospira biflexa serovar Patoc strain 'Patoc 1 (Ames)' | 189910448 | LBF_0894 |
| Methylotenera sp. 301 | 297539640 | M301_2470 |
| Burkholderia ambifaria AMMD | 115359129 | Bamb_4381 |
| Lysinibacillus sphaericus C3-41 | 169828468 | Bsph_2967 |
| Burkholderia sp. CCGE1002 | 295699817 | BC1002_4206 |
| Xanthomonas campestris pv. campestris str. B100 | 188992436 | xccb100_3041 |
| Psychrobacter arcticus 273-4 | 71065462 | Psyc_0902 |
| Xylella fastidiosa 9a5c | 15837717 | XF1115 |
| Shewanella piezotolerans WP3 | 212636147 | swp_3384 |
| Mycobacterium smegmatis str. MC2 155 NC_008596 | 118468149 | MSMEG_4119 |
| Brevibacillus brevis NBRC 100599 | 226311256 | BBR47_16690 |
| Herpetosiphon aurantiacus ATCC 23779 | 159897731 | Haur_1202 |
| Leptospira biflexa serovar Patoc strain 'Patoc 1 (Paris)' | 183220331 | LEPBI_I0927 |
| Marinobacter aquaeolei VT8 | 120555046 | Maqu_2131 |
| Pseudomonas mendocina ymp | 146306406 | Pmen_1374 |
| Fenimonas balearica DSM 9799 | 308048738 | Fbal_1021 |
| Sphingobacterium sp. 21 | 326798186 | Sph21_0758 |

Enzymatic Capability 6: From MAA-CoA to MMA

Enzymatic Capability 6 comprises the ability to convert MAA-CoA to MMA by cleavage of the CoA from MAA-CoA. Such activity may be imparted by an alcohol acyl transferase (AAT) enzyme. In one embodiment, the AAT enzyme is coded by the *Malus pumila* AAT gene. In one embodiment, the host microorganism is yeast. In another embodiment, the host microorganism is yeast and the AAT gene is a *Malus pumila* AAT gene codon-optimized for expression in yeast, for example the AAT gene comprising SEQ ID No: 2. Alternatively, an AAT gene selected from Table 9 may be used.

TABLE 8

AAT Homologs and Orthologs. Gene

| Gene Descriptor (Uniprot ID number) | Gene Descriptor (Uniprot ID number) |
|---|---|
| A0A0B2SBV5 | Q64FJ6 |
| I1J859 | V9P9R1 |
| UPI0003D6F583 | UPI000498BC7F |
| UPI0003D788E3 | V9P9L8 |
| V4TGK2 | Q6QLX5 |
| A8W8Y0 | UPI000498A175 |
| W9STV1 | V9P9M2 |
| W9S561 | U5GMN1 |
| A0A068BGA5 | A0A067K2U6 |
| UPI00051082F8 | UPI0005FC091A |
| UPI000511B89C | Q8GV03 |
| UPI000498D560 | UPI0005811CF4 |
| A9YCD1 | M5W9C4 |
| U5GQY0 | M5WLR7 |
| UPI000579EB90 | UPI00046DB41D |
| UPI00051192DA | K4BYU6 |
| Q5GJ80 | UPI000523FDB9 |
| UPI00051161D8 | A0A059C378 |
| UPI0004988A4D | UPI0005205BA1 |
| UPI000511AD74 | M5WU76 |
| UPI00049877DB | UPI000498EB94 |
| UPI000498867B | UPI00057A1605 |
| Q6R311 | UPI00057A4ABE |
| V9QNV9 | B9NG88 |
| UPI000498C0D7 | UPI000499245B |
| A0A0B4VC61 | B3VP15 |
| V9P9T8 | M1C8D7 |
|  | V4W0X4 |
|  | UPI0003D7778A |
|  | UPI00046DDD34 |

Enzymatic Capabilities

In the invention, examples of the origin of the above enzymes (genes encoding enzymes) include genus *Pseudomonas*, genus *Bacillus*, genus *Sphingobacterium*, genus *Comamonas*, genus *Brevundimonas*, genus *Sphingomonas*, genus *Ochrobactrum*, genus *Pedobacter*, genus *Paenibacillus*, genus *Achromobacter*, genus *Acinetobacter*, genus *Shewanella*, genus *Listonella*, genus *Agrobacterium*, genus *Mesorhizobium*, genus *Rhizobium*, genus *Paracoccus*, genus *Xanthobacter*, genus *Streptomyces*, genus *Geobacillus*, genus *Rhodococcus*, genus *Saccharomyces*, genus *Candida* or genus *Aspergillus*. Of these, genus *Pseudomonas* and genus *Rhodococcus* microorganisms are preferable.

Examples of the microorganism classified into genus *Pseudomonas* include *Pseudomonas aeruginosa*, *Pseudomonas agarici*, *Pseudomonas alcaligenes*, *Pseudomonas amygdale*, *Pseudomonas anguiliseptica*, *Pseudomonas antimicrobica*, *Pseudomonas aspleni*, *Pseudomonas aurantiaca*, *Pseudomonas aureofaciens*, *Pseudomonas avellanae*, *Pseudomonas azotoformans*, *Pseudomonas balearica*, *Pseudomonas beijerinckii*, *Pseudomonas beteli*, *Pseudomonas boreopolis*, *Pseudomonas carboxyhydrogena*, *Pseudomonas caricapapayae*, *Pseudomonas cichorii*, *Pseudomonas cissicola*, *Pseudomonas citronellolis*, *Pseudomonas coronafaciens*, *Pseudomonas corrugate*, *Pseudomonas doudoroffii*, *Pseudomonas echinoids*, *Pseudomonas elongate*, *Pseudomonas ficuserectae*, *Pseudomonas flavescens*, *Pseudomonas flectens*, *Pseudomonas fluorescens*, *Pseudomonas fragi*, *Pseudomonas fulva*, *Pseudomonas fuscovaginae*, *Pseudomonas gelidicola*, *Pseudomonas geniculata*, *Pseudomonas glathei*, *Pseudomonas halophila*, *Pseudomonas hibiscicola*, *Pseudomonas huttiensis*, *Pseudomonas iners*, *Pseudomonas lancelota*, *Pseudomonas lemoignei*, *Pseudomonas lundensis*, *Pseudomonas luteola*, *Pseudomonas marginalis*,

*Pseudomonas meliae, Pseudomonas mendocina, Pseudomonas mucidolens, Pseudomonas monteilli, Pseudomonas nautica, Pseudomonas nitroreducens, Pseudomonas oleovorans, Pseudomonas oryzihabitans, Pseudomonas pertucinogena, Pseudomonas phenazinium, Pseudomonas pictorum, Pseudomonas pseudoalcaligenes, Pseudomonas putida, Pseudomonas pyrrocinia, Pseudomonas resinovorans, Pseudomonas rhodesiae, Pseudomonas saccharophila, Pseudomonas savastanoi, Pseudomonas spinosa, Pseudomonas stanieri, Pseudomonas straminae, Pseudomonas stutzeri, Pseudomonas synxantha, Pseudomonas syringae, Pseudomonas syzygii, Pseudomonas taetrolens, Pseudomonas tolaasii, Pseudomonas veronii, Pseudomonas viridiflava, Pseudomonas vulgaris* and *Pseudomonas wisconsinensis.*

Examples of the microorganism classified into genus *Rhodococcus* include *Rhodococcus rhodochrous, Rhodococcus erythropolis, Rhodococcus equi, Rhodococcus opacus, Rhodococcus jostii, Rhodococcus pyridinovorans, Rhodococcus rhodnii, Rhodococcus corallinus, Rhodococcus rubropertinctus, Rhodococcus coprophilus, Rhodococcus globerulus, Rhodococcus chlorophenolicus, Rhodococcus luteus, Rhodococcus aichiensis, Rhodococcus chubuensis, Rhodococcus maris* and *Rhodococcus fascians.*

For the genes encoding the enzyme, RNA is extracted from the above microorganism cell in accordance with a routine method, a primer is designed based on amino acid sequences and gene sequences of the above enzymes (the microorganism or related species thereto) disclosed in the public databases such as NCBI, and PCR can be carried out using the primer to thereby isolate and amplify the gene encoding the enzyme of interest.

Methacrylyl-CoA-Producing Microorganism

The invention encompasses an engineered microorganism capable of producing MAA-CoA from valine. Such an engineered microorganism of the invention comprises the microorganism which possesses Enzymatic Capability 1, Enzymatic Capability 2, and Enzymatic Capability 3, as described above.

The enzyme may be produced in the cytosol or may be targeted to any other cellular compartment. In one embodiment, the enzyme introduced by transformation and expressed by the MAA-CoA producing microorganism is targeted to the mitochondria. In one embodiment, the mitochondrial-targeted enzyme is targeted to the mitochondrial matrix. In one embodiment, the mitochondrial-targeted protein comprises a targeting moiety comprising the Su9 or Cox1 presequence. In one embodiment, the engineered microorganism is a yeast. In one embodiment, the yeast is *Saccharomyces cerevisiae.*

In one embodiment, the engineered microorganism has been transformed to express one or more acyl-CoA dehydrogenases (isobutyryl-CoA dehydrogenase). For example, the MAA-CoA producing microorganism is transformed to express the *Pseudomonas aeruginosa* ACD1 gene. In another embodiment, the MAA-coA producing microorganism is transformed to express one or more enzymes which catalyze the decarboxylation of 2-oxoisovalerate to isobutyryl-CoA. For example, the MAA-CoA producing microorganism is transformed to express one, some, or all of the components of the BCKAD complex. In yet another embodiment, the MAA-CoA producing microorganism of the invention is transformed to express one or more enzymes which catalyze the formation of 2-oxoisovalerate from valine, for example the BCAT1 or BCAT2 genes from yeast.

3-HIB-Producing Microorganism

The scope of the invention encompasses host microorganisms which have been engineered to produce (S)-3-hydroxyisobutyric acid (3-HIB) from valine. 3-HIB is an MMA precursor which can be readily converted to MMA utilizing various methods known in the art.

The 3-HIB-producing microorganism of the invention is a microorganism which possesses Enzymatic Capability 1, Enzymatic Capability 2, Enzymatic Capability 3, Enzymatic Capability 4, and Enzymatic Capability 5.

In one embodiment, the 3-HIB-producing microorganism of the invention is a host cell that has been transformed to express an ECH gene, for example, the echA gene from *Pseudomonas aeruginosa.* In another embodiment, the 3-HIB-producing microorganism of the invention is a host cell that has been transformed to express one or more HCH enzymes that cleave CoA from 3-hydroxyisobutyryl-CoA. For example the 3-HIB producing microorganism may comprise an microorganism which expresses the hchA gene from *Pseudomonas aeruginosa.* In one embodiment, the engineered microorganism is a yeast. In one embodiment, the yeast is *Saccharomyces cerevisiae.* In one embodiment, the enzyme introduced by transformation and expressed by MAA-CoA producing microorganism is targeted to the mitochondria. In one embodiment, the mitochondrial-targeted enzyme is targeted to the mitochondrial matrix. In one embodiment, the mitochondrial-targeted protein comprises a targeting moiety comprising the Su9 or Cox1 matrix-targeting presequence.

MMA-Producing Microorganism

In one embodiment, the engineered microorganism of the invention is capable of producing MMA. An MMA-producing microorganisms of the invention comprises an microorganism which possesses Enzymatic Capability 1, Enzymatic Capability 2, Enzymatic Capability 3, and Enzymatic Capability 6. In one embodiment, the MMA-producing microorganism of the invention has been transformed to express an alcohol acyl transferase (AAT), for example the AAT gene of *Malus pumila.* In one embodiment, the AAT gene is encoded by SEQ 1D NO: 2. In one embodiment, the MMA-producing microorganism is a yeast. In one embodiment, the yeast is *Saccharomyces cerevisiae.* In one embodiment, the mitochondrial-targeted enzyme is targeted to the mitochondrial matrix. In one embodiment, the mitochondrial-targeted protein comprises a targeting moiety comprising the Su9 presequence.

Additional Genetic Modification

In addition to the various combinations of Enzymatic Capabilities described above, the engineered microorganisms of the invention may further comprise genetic modifications to promote MMA end-product formation. For example, the starting material for bioproduction of MMA end-product is valine. Accordingly, in one embodiment, the microorganisms of the invention are engineered to express one or more enzymes which enhance valine formation over wild-type levels. Various genetic modifications are known in the art for enhancing valine formation in various microorganisms, for example as described in Literature [Wada et al., 2008, Enhanced Valine Production in *Corynebacterium glutamicum* with Defective H+-ATPase and C-Terminal Truncated Acetohydroxyacid Synthase, Bioscience, Biotechnology, and Biochemistry 72 (11):2959-65, 2008; Hasegawa et al., 2013, Engineering of *Corynebacterium glutamicum* for high-yield L-valine production under oxygen deprivation conditions, Appl Environ Microbiol, 79(4):1250-7; and Park et al., 2007, Metabolic engineering of *Escherichia coli* for the production of L-valine based on transcriptome analysis and in silico gene knockout simulation, PNAS 104 (19) 7799-7802]. The enzyme or regulatory gene inserted to a microorganism to enhance the formation of valine may be under the control of a constitutive promoter or inducible promoter.

Under some culture conditions, such as highly aerated yeast cultures, biosynthetic pathways, such as Erlich pathway reactions, compete with MMA end-product formation. In some embodiments, the engineered microorganism of the invention is further engineered to downregulate or obliterate competing biosynthetic pathway. For example, in one embodiment, the bioengineered microorganisms of the invention is engineered to express miRNA or other sequences that downregulate or otherwise target enzymes which compete with any of Enzymatic Capabilities 1 to 6. For example, in one embodiment, the microorganism of the invention is engineered with an enzymatic or a regulatory gene which reduces Erlich pathway reaction. In another embodiment, the enzymatic or regulatory gene co-introduced into the host species comprise genes which inhibit valine catabolism, for example, the reaction which forms succinyl Co-A from 3-HIB Co-A. Such gene may be placed under the control of an inducible promoter, allowing downregulation to be induced after cultures have been propagated and are being switched to bioproduction mode.

In another embodiment, the engineered microorganism of the invention is further engineered to express an enzyme or a regulatory sequence which enhances the regeneration of co-factor such as NADH or FADH. For example, in one embodiment, the engineered microorganism of the invention is transformed to express a high level of alcohol dehydrogenase, in order to promote NADH formation from NADPH, which such cofactor is necessary for the action of the BCKAD complex. Likewise, genetic modifications may be introduced that increase the rate of regeneration of FAD from FADH2, a cofactor in the action of ACD. Exemplary cofactor manipulation technologies are described in Literatures [Wang et al., "Engineering of cofactor regeneration enhances (2S,3S)-2,3-butanediol production from diacetyl," Sci Rep. 2013; 3:2643. doi: 10.1 038/srep02643; Nikel et al., "Elimination of D-lactate synthesis increases poly(3-hydroxybutyrate) and ethanol synthesis from glycerol and affects cofactor distribution in recombinant *Escherichia coli*," Appl Environ Microbiol. 2010 November; 76 (22): 7400-6; Tseng and Prather, "Controlled biosynthesis of odd-chain fuels and chemicals via engineered modular metabolic pathways," Proc Natl Acad Sci USA. 2012 Oct. 30; 109(44):17925-30; and Lopez de Felipe et al., "Cofactor Engineering: a Novel Approach to Metabolic Engineering in *Lactococcus lactis* by Controlled Expression of NADH Oxidase," J Bacteriol. 1998 August; 180(15): 3804-3808].

Methacrylic Acid Ester and Methacrylic Acid Ester Precursor Production

The scope of the invention encompasses the engineered microorganism described above, and further encompasses a method of using such an engineered microorganism to produce the end-products such as MMA.

The engineered microorganisms are cultured so as to propagate themselves and to produce the methacrylic acid esters or methacrylic acid ester precursors end-products. The engineered microorganisms may be cultured under continuous culture conditions for the sustained growth of cultures and simultaneous harvest of end-products. Alternatively, the microorganisms may be cultured in batches wherein discreet cultures (e.g. in a single vessel or bioreactor) are used to form end products, and then are processed to recover the end-products.

In some embodiments, the culture of the engineered microorganisms is staged, with a first growth and/or propagation stage followed by a bioproduction stage. The various stages may be implemented by altering culture conditions, wherein the initial growth and propagation stage is fostered by the use of media and/or culture conditions that favor rapid propagation and growth of the engineered microorganism, followed by a change in culture conditions to favor MMA end-product formation.

For example, in one embodiment, the engineered microorganism of the invention is a yeast and is first grown under culture conditions that favor rapid propagation and growth of yeast cultures, for example well aerated conditions with high levels of nutrients in the growth media. This growth stage is followed by a bioproduction stage wherein the cultures are not highly aerated or are not aerated at all and the culture medium lacks one or more nutrients (e.g. micronutrients, or carbon sources that promote growth).

Each condition such as culture temperature or culture time is suitably determined without particular limitation depending on raw materials, microorganisms to be used, and end-products of interest, but the reaction may be usually carried out at 5 to 80° C. for 1 minute to 1 week. The reaction is preferably carried out at 10 to 70° C. for 1 minute to 120 hours, with 10 minutes or more being more preferable. The conditions under which the reaction quenches are preferably selected from these conditions. The pH of the reaction solution is also not particularly limited as long as the reaction proceeds effectively and, for example, pH ranges from 4 to 10, with pH 5.5 to 8.5 being preferable.

For the purpose of effectively progressing the reaction, the culture can also be carried out in a system to which an organic solvent is added in advance. For the organic solvent, for example, linear, branched or cyclic saturated or unsaturated aliphatic hydrocarbons, or saturated or unsaturated aromatic hydrocarbons can be used singly or in combinations of two or more. Specific examples include hydrocarbon solvents (e.g., pentane, hexane, cyclohexane, benzene, toluene and xylene), halogenated hydrocarbon solvents (e.g., methylene chlorides and chloroform), ether solvents (e.g., diethyl ether, dipropyl ether, diisopropyl ether, dibutyl ether, t-butyl methyl ether and dimethoxyethane) and ester solvents (e.g., methyl formate, methyl acetate, ethyl acetate, butyl acetate and methyl propionate).

In one embodiment, following the growth and propagation stage, the cells are collected and placed in culture vessels having conditions favoring higher bioproduction. For example, yeast cells may be isolated from growth and propagation cultures by centrifugation, followed by rinsing in buffer and resuspension in new culture medium.

In microorganisms wherein one or more of the proteins comprising the Enzymatic Capabilities is under the control of an inducible promoter, the inducing agent may be introduced near or at the beginning of the bioproduction stage. Likewise, in microorganisms which have been engineered for decreased or inhibited activity of metabolic pathways that compete with or otherwise reduce MMA end-product formation, and where such introduced genes are under the control of inducible promoters. The cultured cells may be exposed to the inducing agent at the transition from the growth and propagation stage to the bioproduction stage.

In some embodiments, valine is added to the culture medium to enhance formation of MMA end-products from valine. In another embodiment, valine is added to the culture medium at the transition to a bioproduction culture stage. In another embodiment, valine precursors are included in the growth media to improve valine formation and drive increased rates of MMA end-product formation. Likewise, in microorganisms which have been engineered for increased valine formation by the introduction of genes and where such genes are under the control of inducible promoters, the inducing agent may be introduced at or near the beginning of the bioproduction stage to increase the amount of precursors for end-product formation. In some embodiments, the engineered microorganisms of the invention are co-cultured with other strains or microorganisms which produce valine, in order to increase the concentration of valine in the culture medium.

During culture, in the case of continuous production systems, or at the completion of the bioproduction stage, in the case of batch cultures, the end-products are recovered from the culture. This may be accomplished by any means. For example in one embodiment, enzymatic and/or physical treatments are applied to lyse cells and to liberate the end-products. The MMA end-products may be isolated from cell cultures by centrifugation, distillation, column separation, chromatography, and other means known in the art. For example, methodologies described in U.S. Pat. No. 8,907,121, by Johnson and Morris, entitled "Methyl methacrylate purification process," may be employed.

In the case of methacrylic acid ester precursors, the precursor recovered from cultures may be further treated to convert them to a methacrylic acid esters. 3-HIB may be treated enzymatically to convert it to MMA. For example, the dehydration of 3-HIB to MMA may be achieved, for example as described in Literature [Nagai, "New Developments in the Production of Methyl Methacrylate," Applied Catalysis A: General 221 (2001) 367-377].

The method of the invention can also be used for the production of methacrylic acid esters or precursors thereof from a biomass. A transformant having introduced thereinto the gene encoding an acyl-CoA dehydratase, as well as an enzyme gene group allowing for synthesizing methacrylic acid esters or precursors thereof of interest from a biomass can be used to directly synthesize methacrylic acids or methacrylic acid esters from the biomass in a metabolic engineering (fermentation) approach.

Figure 2:
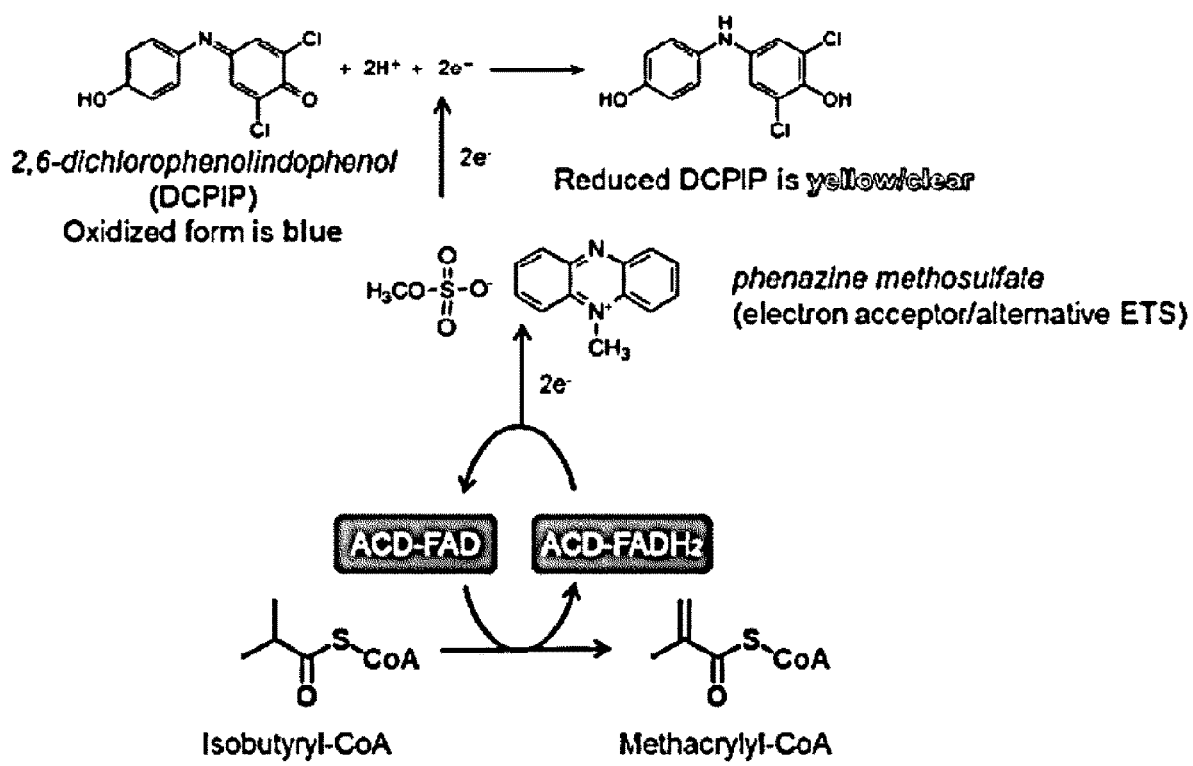
FIG. 2 depicts synthetic pathways and experimental results in the exemplary implementation of the invention described in Example 1. Colorimetric analysis of ACD activity. The reaction progress was monitored in real time in terms of the absorption reduction rate at 600 nm.
Figure 3:
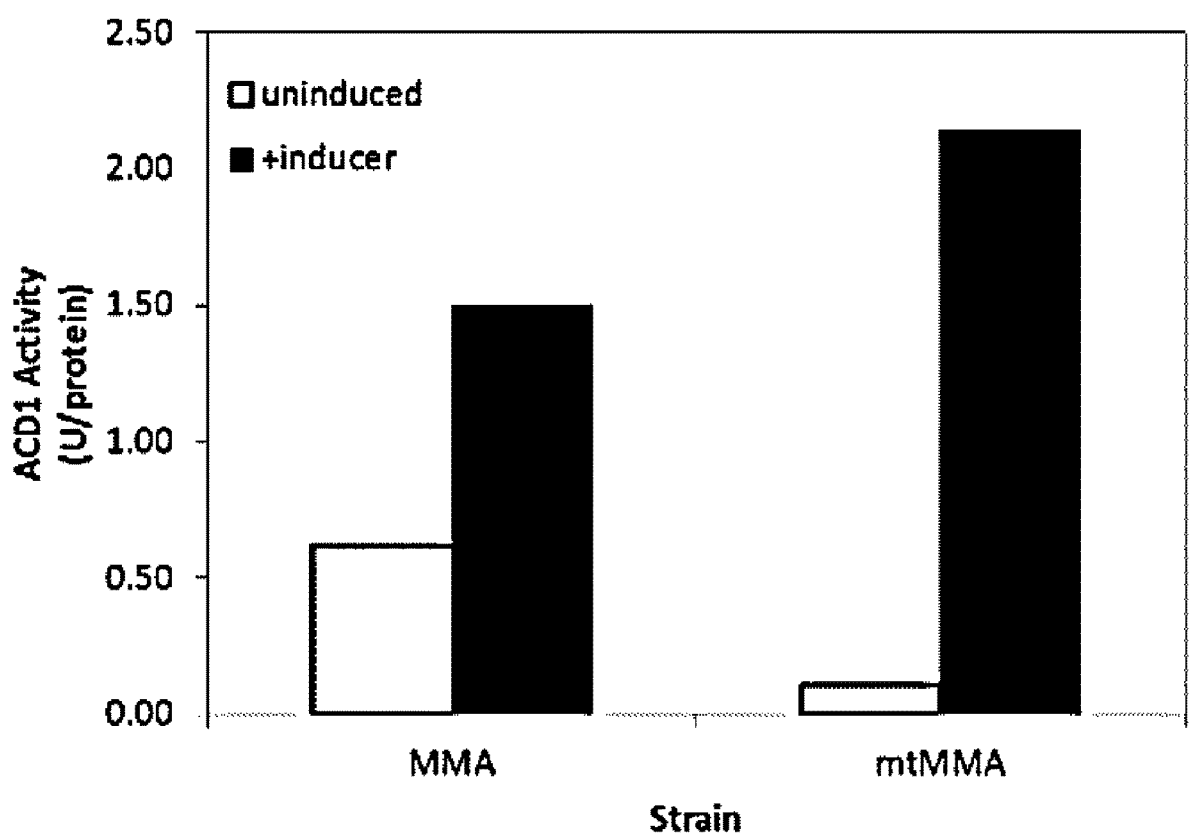
FIG. 3 depicts synthetic pathways and experimental results in the exemplary implementation of the invention described in Example 1. The vertical axis shows the activity of recombinant ACD (acd1) expressed in *S. cerevisiae* after 48-hour expression/induction in a cytoplasm (MMA) and a mitochondrion (mtMMA).
Figure 4:
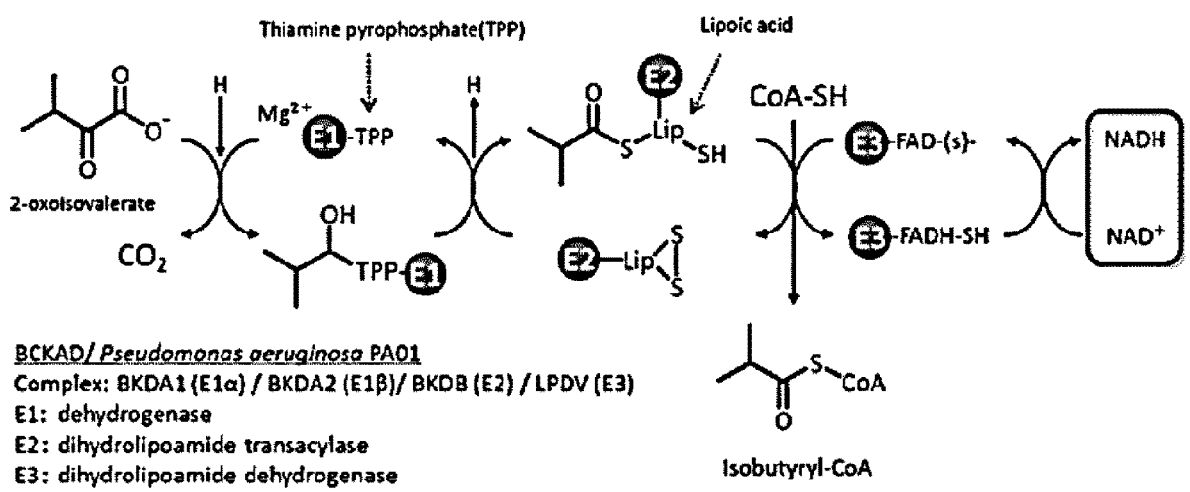
FIG. 4 depicts synthetic pathways and experimental results in the exemplary implementation of the invention described in Example 1. Spectroscopic analysis of BCKAD activity. The reaction progress was monitored in real time in terms of the absorption reduction rate at 340 nm.
Figure 5:
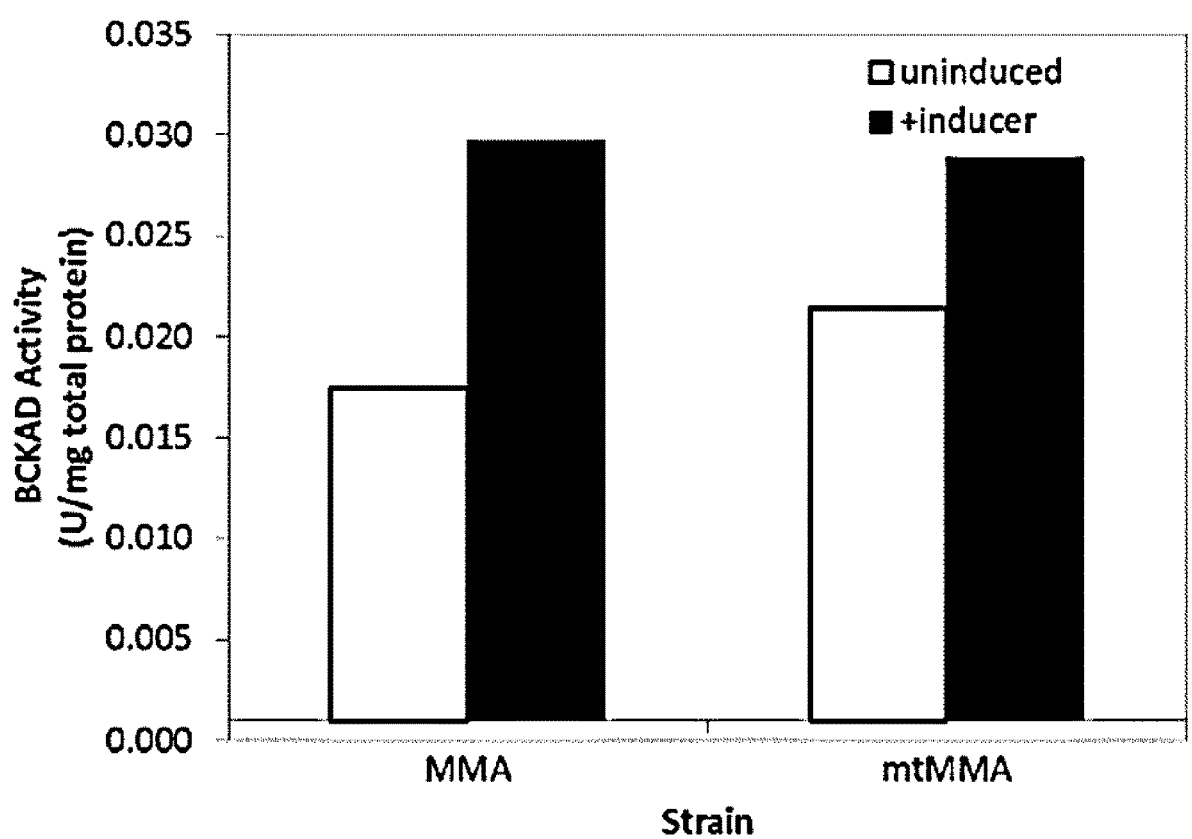
FIG. 5 depicts synthetic pathways and experimental results in the exemplary implementation of the invention described in Example 1. The vertical axis shows the activities of recombinant BCKAD (bkdA1, bkdA2, lpdV, bkdB) expressed in *S. cerevisiae* after 48-hour expression/induction in a cytoplasm (MMA) and a mitochondrion (mtMMA).

The additional details in regard to the experiment methods described in the invention and Example 1 are presented in FIGS. 2 and 5.

EXAMPLE

Mitochondrial Expression of Pathway Genes

Genes were targeted for expression to the cytoplasm by expressing the heterologous gene, or targeted to the mitochondria by appending the first 69 residues of subunit 9 of the yeast mitochondrial ATPase (Su9) to each gene as encoded by SEQ ID NO: 1.

Expression and correct targeting of these genes was then validated by constructing a C-terminal GFP fusion which was expressed from a GAL1 promoter within the plasmid pYES (leader peptide, plasmid, GAL1 promoter, CYCT terminator and GFP, all provided from the paper: Westermann, B. and Neupert, W. (2000). Yeast 16: 1421-1427). These constructs were transformed in *Saccharomyces cerevisiae* (CKY263) and grown overnight in glucose supplemented synthetic defined media lacking uracil (SD-CAA). At 24 hour, the cultures were diluted 100 fold and expression induced by growing them in galactose supplemented SO-CAA for 24 hours. The cells were harvested and stained with a red fluorescent mitochondria-selective dye (Mito-IO Red detection kit-Cat # ENZ-51007-500, Enzo Life Sciences, Ann Arbor, Mich.). Fluorescence was then detected using confocal microscopy-only cells with non-diffuse green fluorescence which overlaps with the red dye target gene expression to the mitochondria.

Recombinant Activity of Targeted MMA Pathway Genes

Activity of the first two enzymatic steps (BCKAO and ACO) were confirmed with in vitro assays of crude lysates from cells that expressed GFP-free constructs. MMA enzymes expression cassettes (BCKAO, ACO, ECH, HCH) targeted to either the mitochondria (mtMMA) or cytoplasm (MMA) were cloned from the previous experiment into the pRS series of vectors (pBCKA04-pRS315 backbone (LEU) with bkdA1, bkdA2, bkdB, JpdV; pAC01-pRS316 backbone (URA) with acd1; and pCoA2-pRS314 backbone (TRP) with echA and hchA). These plasmids were transformed into the vacuolar protease-deficient *Saccharomyces cerevisiae* strain BJ5464. After a 48-hour induction period in galactose supplemented SO-CAA lacking uracil, leucine and tryptophan, cells were harvested, physically disrupted in Tris buffer and the lysate separated by centrifugation. The lysates were then assayed with real-time enzymatic activity assays as depicted below:

ACD Assay
100 mM Potassium phosphate pH 8.0
1.0 mM N-Ethylmaleimide
0.03 mM Isobutyryl-CoA
0.4 mM Flavin adenine dinucleotide (FAD)
1.6 mM Phenazine methosulphate (PMS)
0.035 mM 2,6-Dichlorophenol-indophenol (DCPIP)
+ Sample
Room temperature incubation
Active ACD reduces DCPIP and $A_{600}$
BCKAD Assay
100 mM Potassium phosphate pH 7.0
1 mM $MgCl_2$
0.2 mM Thiamin pyrophosphate (TPP)
4 mM 2-Oxoisovaleric acid
0.2 mM CoASH/2 mM DTT
2 mM $NAD^+$
2 mM L-valine
+ Sample
Room temperature incubation
Active BCKAD reduces $NAD^+$ and increases $A_{340}$
Production of 3-Hydroxyisobutyrate Productivity from the (mt)MMA pathway was assessed using high-pressure liquid chromatography. BJ5464 cells containing mitochondrial or cytoplasmic variants of the pathway were grown overnight under non-inducing conditions. These cultures were then diluted about 100 fold in inducing SD-CAA media and grown for 48 to 72 hours. Supernatant from these cultures were then analyzed on an Agilent 1100 series HPLC with an ICsep USP L-17 using a 0.01 N $H_2SO_4$ mobile phase. 3-HIB product was detected at 210 nm with a DAD detector and quantified via a standard curve. These studies suggest production of g/L titers of 3-HIB (5.1±2.9 g/L) in 72 hours with the mitochondrial pathway variant.

All patents, patent applications, and publications cited in this specification are herein incorporated by reference in their entirety to the same extent as if each independent patent, patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

INDUSTRIAL APPLICABILITY

The invention is useful for synthesizing methacrylic acid esters such as MMA to begin with and acrylic resins, which are polymers thereof.

The invention claimed is:

1. A eukaryotic microorganism into which a gene encoding an acyl-CoA dehydrogenase is introduced, wherein the gene encoding the acyl-CoA dehydrogenase comprises a signal sequence that localizes the acyl-CoA dehydrogenase expressed by the gene to mitochondria, and wherein the signal sequence comprises the nucleotide sequence of SEQ ID NO: 1.

2. The eukaryotic microorganism according to claim 1, wherein the gene encoding an acyl-CoA dehydrogenase is derived from at least one selected from the group consisting of genus *Pseudomonas*, genus *Bacillus*, genus *Sphingobacterium*, genus *Comamonas*, genus *Brevundimonas*, genus *Sphingomonas*, genus *Ochrobactrum*, genus *Pedobacter*, genus *Paenibacillus*, genus *Achromobacter*, genus *Acinetobacter*, genus *Shewanella*, genus *Listonella*, genus *Agrobacterium*, genus *Mesorhizobium*, genus *Rhizobium*, genus *Paracoccus*, genus *Xanthobacter*, genus *Streptomyces*, genus *Geobacillus*, genus *Rhodococcus*, genus *Saccharomyces*, genus *Candida* and genus *Aspergillus*.

3. The eukaryotic microorganism according to claim 1, wherein the eukaryotic microorganism is an yeast.

4. The eukaryotic microorganism according to claim 1, further comprising at least one exogenous gene selected from the group consisting of a gene encoding branched-chain keto acid dehydrogenase, a gene encoding enoyl-CoA hydratase, a gene encoding hydroxyacyl-CoA hydrolase, a gene encoding thioesterase, and a gene encoding alcohol acyl transferase.

5. The eukaryotic microorganism according to claim 1, wherein the acyl-CoA dehydrogenase is an isobutyryl-CoA dehydrogenase.

6. A method for producing methacrylyl-CoA from valine, said method comprising culturing the eukaryotic host cell of claim 4 under conditions suitable for said host cell to synthesize the methacrylyl-CoA.

7. A method for producing 3-hydroxyisobutyryl-CoA from valine, said method comprising culturing the eukaryotic host cell of claim 4 under conditions suitable for said host cell to synthesize 3-hydroxyisobutyryl-CoA.

8. A method for producing 3-hydroxyisobutyric acid from valine, said method comprising culturing the eukaryotic host cell of claim 4 under conditions suitable for said host cell to synthesize the 3-hydroxyisobutyric acid.

9. A method for producing a methacrylic acid ester from valine, said method comprising culturing the eukaryotic host cell of claim 4 under conditions suitable for said host cell to synthesize the methacrylic acid ester.

\* \* \* \* \*

SEQUENCE LISTING

<160> NUMBER OF SEQ ID NOS: 2

<210> SEQ ID NO 1
<211> LENGTH: 207
<212> TYPE: DNA
<213> ORGANISM: Saccharomyces cerevisiae

<400> SEQUENCE: 1

| | |
|---|---|
| atggcctcca ctcgtgtcct cgcctctcgc ctggcctccc agatggctgc ttccgccaag | 60 |
| gttgcccgcc ctgctgtccg cgttgctcag gtcagcaagc gcaccatcca gactggctcc | 120 |
| cccctccaga ccctcaagcg cacccagatg acctccatcg tcaacgccac cacccgccag | 180 |
| gctttccaga agcgcgccta ctcttcc | 207 |

<210> SEQ ID NO 2
<211> LENGTH: 1368
<212> TYPE: DNA
<213> ORGANISM: Malus pumila

<400> SEQUENCE: 2

| | |
|---|---|
| atgatgagct tttctgtact ccaagtcaaa cgcctgcaac cagaactgat tacgccagcg | 60 |
| aaatcgaccc cgcaggaaac caaattcctg tctgacatcg atgaccaaga gagcttgcgt | 120 |
| gtgcagattc cgatcatcat gtgctataaa gacaacccga gcctgaataa gaatcgcaat | 180 |
| ccggttaagg ccattcgtga ggccctgtcc cgtgcgctgg tttactatta cccgctggcg | 240 |
| ggtcgtctgc gtgagggtcc gaatcgcaaa ctggtggtgg actgcaatgg tgagggtatt | 300 |
| ctgtttgttg aggcgagcgc ggacgtcacc ctggaacagc tgggcgacaa gatcctgccg | 360 |
| ccgtgtccgc tgttggaaga gtttctgtac aacttcccgg gcagcgatgg tatcatcgat | 420 |
| tgcccgctgc tgctgattca agtcacttgt ctgacgtgtg gtggctttat tctggctctg | 480 |
| cgcctgaacc acaccatgtg tgatgcagcg ggtttgttgc tgttcctgac cgccatcgca | 540 |
| gagatggccc gtggtgccca cgcaccgagc attctgccgg tgtgggaacg tgaactgctg | 600 |
| ttcgcacgtg acccgcctcg tattacttgc gcgcaccatg aatacgagga cgttatcggc | 660 |
| catagcgacg gcagctacgc gagcagcaac caaagcaata tggtgcagcg tagcttttac | 720 |
| ttcggcgcga agaaatgcg tgttctgcgc aagcagatcc cgcctcacct gatcagcacg | 780 |
| tgcagcacct tgatttgat taccgcatgc ctgtggaagt gccgtacgct ggcgctgaac | 840 |
| atcaacccga agaagccgt ccgtgtgagc tgtatcgtta cgcgcgtgg taaacacaac | 900 |
| aatgttcgcc tgccgctggg ctattacggc aatgcgttcg cattcccggc tgctatctct | 960 |
| aaggcagagc cgctgtgtaa gaaccctctg ggttacgccc tggagttggt gaagaaggcg | 1020 |
| aaagcgacca tgaatgaaga gtatctgcgc agcgtggcgg atctgctggt tttgcgcggt | 1080 |
| cgtccgcaat actccagcac gggttcctat ctgattgtga gcgacaatac ccgcgtgggt | 1140 |
| tttggtgatg tcaacttcgg ttggggccag ccagtctttg ctggcccggt caaagcattg | 1200 |
| gacctgatta gcttctatgt tcaacataag aacaacacgg aagatggtat cttggttccg | 1260 |
| atgtgcctgc cgtcctcggc gatggagcgt ttccaacagg agctgagcg cattacccag | 1320 |
| gaaccgaaag aggatatttg caacaatctg cgtagcacca gccagtaa | 1368 |